United States Patent
Harada et al.

(10) Patent No.: US 9,889,108 B2
(45) Date of Patent: Feb. 13, 2018

(54) COMPOSITIONS AND METHODS FOR TREATING NON-ALCOHOLIC STEATOHEPATITIS

(71) Applicant: MOCHIDA PHARMACEUTICAL CO., LTD., Tokyo (JP)

(72) Inventors: Tsuyoshi Harada, Tokyo (JP); Hideo Kanehiro, Tokyo (JP); Kiyoshi Mizuguchi, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/775,452

(22) PCT Filed: Mar. 14, 2014

(86) PCT No.: PCT/JP2014/058145
§ 371 (c)(1),
(2) Date: Sep. 11, 2015

(87) PCT Pub. No.: WO2014/142364
PCT Pub. Date: Sep. 18, 2014

(65) Prior Publication Data
US 2016/0030378 A1 Feb. 4, 2016

Related U.S. Application Data

(60) Provisional application No. 61/791,533, filed on Mar. 15, 2013, provisional application No. 61/793,309, filed on Mar. 15, 2013, provisional application No. 61/817,796, filed on Apr. 30, 2013.

(51) Int. Cl.
| | | |
|---|---|---|
| A61K 31/232 | (2006.01) | |
| A61K 47/24 | (2006.01) | |
| A61K 47/10 | (2017.01) | |
| A61K 31/202 | (2006.01) | |

(52) U.S. Cl.
CPC .......... *A61K 31/232* (2013.01); *A61K 31/202* (2013.01); *A61K 47/10* (2013.01); *A61K 47/24* (2013.01)

(58) Field of Classification Search
CPC ....... A61K 31/232; A61K 47/10; A61K 47/24
See application file for complete search history.

(56) References Cited

U.S. PATENT DOCUMENTS

| | | |
|---|---|---|
| 3,692,895 A | 9/1972 | Nelson et al. |
| 4,379,785 A | 4/1983 | Weyer et al. |
| 4,572,912 A | 2/1986 | Yoshioka et al. |
| 4,579,730 A | 4/1986 | Kidron et al. |
| 4,639,436 A | 1/1987 | Junge et al. |
| 4,849,405 A | 7/1989 | Ecanow |
| 4,904,769 A | 2/1990 | Rauenbusch |
| 4,963,526 A | 10/1990 | Ecanow |
| 5,019,508 A | 5/1991 | Johnson et al. |
| 5,594,016 A | 1/1997 | Ueno et al. |
| 5,614,492 A | 3/1997 | Habener |
| 5,642,868 A | 7/1997 | Talmy et al. |
| 5,703,188 A | 12/1997 | Mandeville et al. |
| 5,763,396 A | 6/1998 | Weiner et al. |
| 5,824,638 A | 10/1998 | Burnside et al. |
| 5,843,866 A | 12/1998 | Parket et al. |
| 6,153,632 A | 11/2000 | Rieveley |
| 6,191,105 B1 | 2/2001 | Ekwuribe et al. |
| 6,296,850 B1 | 10/2001 | Bjorklund et al. |
| 6,706,488 B2 | 3/2004 | Bjorklund et al. |
| 6,716,968 B2 | 4/2004 | Bjorklund et al. |
| 7,883,904 B2 | 2/2011 | Feldstein et al. |
| 7,897,591 B2 | 3/2011 | Puder et al. |
| 8,853,256 B2 | 10/2014 | Yokoyama et al. |
| 9,060,981 B2 | 6/2015 | Sato et al. |
| 9,486,433 B2 | 11/2016 | Mizuguchi et al. |
| 2007/0218579 A1 | 9/2007 | Urdea et al. |
| 2008/0311593 A1 | 12/2008 | Younossi et al. |
| 2009/0297546 A1 | 12/2009 | Yamada et al. |
| 2011/0082119 A1 | 4/2011 | Yano |
| 2011/0092592 A1 | 4/2011 | Yano |
| 2011/0105510 A1 | 5/2011 | Ishikawa |
| 2012/0065264 A1 | 3/2012 | Fujii et al. |
| 2012/0231471 A1 | 9/2012 | Sato et al. |
| 2012/0264824 A1 | 10/2012 | Mizuguchi et al. |
| 2014/0057981 A1 | 2/2014 | Fujii et al. |
| 2015/0051143 A1 | 2/2015 | Harada et al. |
| 2015/0247869 A1 | 9/2015 | Sato et al. |
| 2015/0258054 A1 | 9/2015 | Mizuguchi et al. |
| 2016/0213639 A1 | 7/2016 | Suzuki et al. |
| 2017/0007566 A1 | 1/2017 | Mizuguchi et al. |

FOREIGN PATENT DOCUMENTS

| | | |
|---|---|---|
| EP | 1582873 A1 | 10/2005 |
| EP | 1782807 A1 | 5/2007 |
| EP | 2308493 A1 | 4/2011 |
| EP | 2433630 A1 | 3/2012 |
| EP | 2490026 A1 | 8/2012 |

(Continued)

OTHER PUBLICATIONS

Nemoto et al. (In Vivo 23;685-690(2009).*
And as evidenced by Farrell et al. (Gut and Liver ; 6(2)2012; 149-171).*
Notarnicola et al. Lipids in Health and Disease 2012, 11:145 (2012).*

(Continued)

*Primary Examiner* — Shirley V Gembeh
(74) *Attorney, Agent, or Firm* — Wilson Sonsini Goodrich & Rosati, P.C.

(57) ABSTRACT

The disclosure provides for a method for treating a fatty liver disease or disorder in a subject in need thereof, comprising selecting a subject having or suspected of having a fatty liver disease or disorder, wherein the subject is non diabetic, pre-diabetic, mildly diabetic; has normal or substantially normal biliary tract function; or has non or early stage hepatocyte apoptosis; and administering a therapeutically effective amount of a pharmaceutical composition comprising EPAs.

29 Claims, 30 Drawing Sheets

(56) References Cited

FOREIGN PATENT DOCUMENTS

| | | |
|---|---|---|
| EP | 2719382 A1 | 4/2014 |
| JP | 2000-102399 A | 4/2000 |
| JP | 2002-114768 A | 4/2002 |
| JP | 2007-236253 A | 9/2007 |
| JP | 2007-315752 A | 12/2007 |
| JP | 2009-120607 A | 6/2009 |
| JP | 2009-534317 A | 9/2009 |
| JP | 2011-006380 A | 1/2011 |
| JP | 2011-519846 A | 7/2011 |
| JP | 2012-180337 A | 9/2012 |
| WO | WO 85/05029 A1 | 11/1985 |
| WO | WO 97/11345 A1 | 3/1997 |
| WO | WO 98/05331 A2 | 2/1998 |
| WO | WO 98/57652 A1 | 12/1998 |
| WO | WO 99/58518 A2 | 11/1999 |
| WO | WO 99/58521 A1 | 11/1999 |
| WO | WO 99/58522 A1 | 11/1999 |
| WO | WO 99/61435 A1 | 12/1999 |
| WO | WO 02/26707 A1 | 4/2002 |
| WO | WO 02/26743 A1 | 4/2002 |
| WO | WO 03/032916 A2 | 4/2003 |
| WO | WO 03/032982 A1 | 4/2003 |
| WO | WO 03/041729 A1 | 5/2003 |
| WO | WO 03/055883 A1 | 7/2003 |
| WO | WO 2005/063231 A2 | 7/2005 |
| WO | WO 2007/016390 A1 | 2/2007 |
| WO | WO 2008/075788 A1 | 6/2008 |
| WO | WO 2008/113177 A1 | 9/2008 |
| WO | WO 2009/028457 A1 | 3/2009 |
| WO | WO 2009/151116 A1 | 12/2009 |
| WO | WO 2009/151125 A1 | 12/2009 |
| WO | WO 2009/154230 A1 | 12/2009 |
| WO | WO-2010004982 A1 | 1/2010 |
| WO | WO 2010/134614 A1 | 11/2010 |
| WO | WO-2011046204 A1 | 4/2011 |
| WO | WO 2012/032417 A2 | 3/2012 |
| WO | WO 2013/127728 A1 | 9/2013 |
| WO | WO 2014/057522 A1 | 4/2014 |
| WO | WO 2014/142364 A2 | 9/2014 |
| WO | WO 2015/053379 A1 | 4/2015 |

OTHER PUBLICATIONS

Tarek et al. ( see p. 5, para 3; J. Hepatol . . . Jun. 2011; 54(6): 1224-1229).*
Yilmaz et al. Hepatology, vol. 49, No. 2, 2009 (697).*
U.S. Appl. No. 14/914,444, filed Feb. 25, 2016, Suzuki et al.
Lee, et al. Comparison of methods to measure low serum estradiol levels in postmenopausal women. J Clin Endocrinol Metab. Oct. 2006;91(10):3791-7. Epub Aug. 1, 2006.
Nichols, et al. From menarche to menopause: trends among US Women born from 1912 to 1969. Am J Epidemiol. Nov. 15, 2006;164(10):1003-11. Epub Aug. 23, 2006.
American Diabetes Association and National Institute of Diabetes, Digestive, and Kidney Diseases. The prevention or delay of type 2 diabetes. Diabetes Care. Apr. 2002;25(4):742-9.
Armutcu, et al. Thymosin alpha 1 attenuates lipid peroxidation and improves fructose-induced steatohepatitis in rats. Clin Biochem. Jun. 2005;38(6):540-7.
Capanni, et al. Prolonged n-3 polyunsaturated fatty acid supplementation ameliorates hepatic steatosis in patients with non-alcoholic fatty liver disease: a pilot study. Aliment Pharmacol Ther. Apr. 15, 2006;23(8):1143-51.
Carpentier, et al. n-3 fatty acids and the metabolic syndrome. Am J Clin Nutr. Jun. 2006;83(6 Suppl):1499S-1504S.
Chatzigeorgiou, et at. Plasma and urine soluble CD40 (sCD40) in children and adolescents with type 1 diabetes mellitus (T1DM). A possible pathway to diabetic angiopathy. FEBS Journal (2008), vol. 275 (Suppl. 1). PP7A-14, p. 303 (abstract).
Cleveland Clinic (downloaded online on Feb. 26, 2015 from URL:< http://my.clevelandclinic.org/health/diagnostics/hic-blood-glucose-test>).

Communication Pursuant to Article 94(3) EPC issued May 16, 2014, in European Patent Application No. 10823472.5.
Database Biosis (Online] BioSciences Information Service, Philadelphia. PA, US (Apr. 2006); Gurhen et at, The Effects of Atorvastatin on Hematological and Inflammatory Parameters,' XP002700442, Database Accession No. PREV200900258247— abstract'.
Database Biosis [Online) BioSciences Information Service, Philadelphia, PA, US (Nov. 2008): Cayon et al, "Gene expression in obese patients with non-alcoholic steatohepatitis," XP002700444, Database Accession No. PREV200800490452 'abstract'.
Dennis. The growing phospholipase A2 superfamily of signal transduction enzymes. Trends Biochem Sci. Jan. 1997;22(1):1-2.
English translation of International Preliminary Report on Patentability and Written Opinion dated Apr. 17, 2012, in PCT International Application No. PCT/JP2010/068168.
Estep, et al. Expression of cytokine signaling genes in morbidly obese patients with non-alcoholic steatohepatitis and hepatic fibrosis. Obes Surg. May 2009;19(5):617-24. doi: 10.1007/s11695-009-9814-x. Epub Mar. 12, 2009.
European search report and opinion dated Mar. 4, 2013 for EP Application No. 12188329.2.
Extended European Search Report dated Jul. 13, 2012, in European Patent Application No. 10823472.5.
Feldstein, et al. Hepatocyte apoptosis and fas expression are prominent features of human nonalcoholic steatohepatitis. Gastroenterology. Aug. 2003;125(2):437-43.
Forst, et al. Improved plaque stabilityyand reduced inflammation during pioglitazone treatment in type 2 diabetic patients with CHD. Diabetes. Jun. 2007; vol. 55, Suppl. 1. 647-P, p. A172.
Forst, et al. Pleiotrophic and anti-inflammatory effects of pioglitazone precede the metabolic activity in type 2 diabetic patients with coronary artery disease. Atherosclerosis. Mar. 2008;197(1):311-7. Epub Jun. 22, 2007.
Hanniman, et al. Apolipoprotein A-IV is regulated by nutritional and metabolic stress: involvement of glucocorticoids, HNF-4 alpha, and PGC-1 alpha. J Lipid Res. Nov. 2006;47(11):2503-14. Epub Aug. 23, 2006.
Haukeland, et al. Systemic inflammation in nonalcoholic fatty liver disease is characterized by elevated levels of CCL2. J Hepatol. Jun. 2006;44(6):1167-74. Epub Mar. 20, 2006.
Horie et al. Hepatocyte-specific pten deficiency results in steatohepatitis and hepatocellular carcinoma, and Insulin Hypersensitivity. Hepatology, Oct. 2004, No. 609, p. 428A.
International preliminary report on patentability and written opinion dated Nov. 20, 2012 for PCT Application No. JP2012/006551.
International search report and written opinion dated Nov. 20, 2012 for PCT Application No. JP2012/006551.
International search report and written opinion dated Dec. 16, 2014 for PCT Application No. JP2014/077120.
International search report dated Jan. 25, 2011 for PCT/JP2010/ 068168.
Jeppesen et al, Relation of High TG—Low HDL Cholesterol and LDL Cholesterol to the Incidence of Ischemic Heart Disease (Arteriosclerosis, Thrombosis, and Vascular Biology. 1997; 17: 1114-1120).
Jin et al. Telmisartan prevents hepatic fibrosis and enzyme-altered lesions in liver cirrhosis rat induced by a choline-deficient L-amino acid-defined diet. Biochem Biophys Res Commun. Dec. 28, 2007;364(4):801-7. Epub Oct. 24, 2007.
Johannsson, et al. Growth hormone treatment of abdominally obese men reduces abdominal fat mass, improves glucose and lipoprotein metabolism, and reduces diastolic blood pressure. J Clin Endocrinol Metab. Mar. 1997;82(3):727-34.
Kajikawa, et al. Eicosapentaenoic acid attenuates progression of hepatic fibrosis with inhibition of reactive oxygen species production in rats fed methionine- and choline-deficient diet. Digestive Diseases and Sciences, 201, vol. 56, No. 4, p. 1065-1074.
Kajikawa, et al. Highly Purified Eicosapentaenoic Acid Ethyl Ester Prevents Development of Steatosis and Hepatic Fibrosis in Rats. Digestive Diseases and Sciences, 2010, vol. 55, No. 3, p. 631-641.
Kan Tan Sui. 2010, vol. 60, No. 5, p. 759-764.
Kanzo. 2002, vol. 43, No. Supplement 2, p. A397.

(56) References Cited

OTHER PUBLICATIONS

Kanzo. 2005, vol. 46, No. Supplement 2, p. A329.
Kanzo. vol. 53, No. Supplement 2, 212, p. A706.
Kawashima, et al. Preventive Effects of Highly Purified Eicosapentaenoic Acid on Development of Steatosis and Hepatic Fibrosis Induced by a Methionine- and Choline-Deficient Diet in Rats. Gastroenterology, 2009, vol. 136, No. 5, p. A804.
Kleiner, et al. Design and validation of a histological scoring system for nonalcoholic fatty liver disease. Hepatology. Jun. 2005;41(6):1313-21.
Kudo, et al. Lipopolysaccharide triggered TNF-alpha-induced hepatocyte apoptosis in a murine non-alcoholic steatohepatitis model. J Hepatol. Jul. 2009;51(1):168-75. doi: 10.1016/j.jhep.2009.02.032. Epub May 3, 2009.
Kurita et al. Olmesartan ameliorates a dietary rat model of non-alcoholic steatohepatitis through its pleiotropic effects. Eur J Pharmacol. Jul. 7, 2008;588(2-3):316-24. doi: 10.1016/j.ejphar.2008.04.028. Epub Apr. 16, 2008.
Mason, et al. Effect of enhanced glycemic control with saxagliptin on endothelial nitric oxide release and CD40 levels in obese rats. J Atheroscler Thromb. 2011;18(9):774-83. Epub Jun. 13, 2011.
MedIndia (downloaded online on Feb. 25, 2015 from URL:<http://www.medindia.net/patients/patientinfo/hba1c-blood-sugar-test.htm>).
Meigs, et al. The natural history of progression from normal glucose tolerance to type 2 diabetes in the Baltimore Longitudinal Study of Aging. Diabetes. Jun. 2003;52(6):1475-84.
Mitsuhashi, H. [Thrombo test (TBT), hepaplastin test (HPT)]. Nihon Rinsho. Dec. 2004;62 Suppl 12:594-6.
National Institutes of Health (NIH) National Institute of Diabetes and Digestive and Kidney Diseases, "Nonalcoholic Steatohepatitis", Nov. 2006.
Neuschwander-Tetri, et al. Nonalcoholic steatohepatitis: summary of an AASLD Single Topic Conference. Hepatology. May 2003;37(5):1202-19.
Notice of allowance dated Feb. 20, 2015 for U.S. Appl. No. 13/500,753.
Notification of Reasons for Refusal dated Nov. 4, 2014, in Japanese Patent Application No. 2011-536192, with English translation.
Obstetrical and Gynecological Practice. vol. 56, No. 8, 2007, p. 1161-1165.
Oestvang, et al. PhospholipaseA2: a key regulator of inflammatory signalling and a connector to fibrosis development in atherosclerosis. Biochim Biophys Acta. Nov. 2006;1761(11):1309-16. Epub Jul. 1, 2006.
Office action dated Feb. 11, 2013 for U.S. Appl. No. 13/088,072.
Office action dated Mar. 21, 2014 for U.S. Appl. No. 13/500,753.
Office action dated May 8, 2015 for U.S. Appl. No. 14/209,964.
Office action dated Jul. 20, 2015 for U.S. Appl. No. 13/088,072.
Office action dated Aug. 13, 2013 for U.S. Appl. No. 13/088,072.
Office action dated Sep. 11, 2015 for U.S. Appl. No. 14/209,964.
Office action dated Nov. 12, 2014 for U.S. Appl. No. 13/500,753.
Office action dated Nov. 21, 2014 for U.S. Appl. No. 13/088,072.
Proceedings of the 61st meeting of Japan Society of Home Economics. 2009, vol. 61st, p. 32.
Proceedings of the 65th Annual meeting of the Japan Society of Nutrition and Food Science. 2011, vol. 65th, p. 110.
Saebo (Pharma marine, downloaded online on Feb. 27, 2015 from URL:<www.calamarine.com>).
Sawada, et al. [NASH model—role of interleukin-1 receptor]. Nihon Rinsho. Jun. 2006;64(6):1063-70.
Schlemmer, et al. Oestrogen and essential fatty acid supplementation corrects bone loss due to ovariectomy in the female Sprague Dawley rat. Prostaglandins Leukot Essent Fatty Acids. vol. 61, No. 6, 1999, pp. 381-390.
Schmilovitz-Weiss et al. Role of circulating soluble CD40 as an apoptotic marker in liver disease. Apoptosis. Mar. 2004;9(2):205-10.
Tamimi, et al. An apoptosis panel for nonalcoholic steatohepatitis diagnosis. J Hepatol. Jun. 2011;54(6):1224-9. doi: 10.1016/j.jhep.2010.08.023. Epub Feb. 12, 2011.
Tanaka, et al. Highly Purified Eicosapentaenoic Acid Treatment Improves Nonalcoholic Steatohepatitis. Journal of Clinical Gastroenterology, 2008, vol. 42, No. 4, p. 413-418.
The Japan Society of Hepatology ed., "NASH • NAFLD no Shinryo Gaido (Guidelines for Diagnosis and Treatment of NASH and NAFLD)", Bunkodo Co., Ltd., Aug. 22, 2006, and its partial translation.
Tirosh, et al. Nutritional lipid-induced oxidative stress leads to mitochondrial dysfunction followed by necrotic death in FaO hepatocytes. Nutrition. Feb. 2009;25(2):200-8. doi: 10.1016/j.nut.2008.07.023. Epub Oct. 22, 2008.
Valva, et al. Apoptosis markers in liver biopsy of nonalcoholic steatohepatitis in pediatric patients. Hum Pathol. Dec. 2008;39(12):1816-22. doi: 10.1016/j.humpath.2008.04.022. Epub Aug. 20, 2008.
Varma, et al. Thrombospondin-1 is an adipokine associated with obesity, adipose inflammation, and insulin resistance. Diabetes. Feb. 2008;57(2):432-9. Epub Dec. 5, 2007.
Varo, et al. Elevated plasma levels of the atherogenic mediator soluble CD40 ligand in diabetic patients: a novel target of thiazolidinediones. Circulation. Jun. 3, 2003;107(21):2664-9. Epub May 12, 2003.
Watanabe, et al. Hepatology Oct. 2004, 428A, 609.
Yener, et al. Plasminogen activator inhibitor-1 and thrombin activatable fibrinolysis inhibitor levels in non-alcoholic steatohepatitis. J Endocrinol Invest. Nov. 2007;30(10):810-9. Abstract only.
Yoneda, et al. Plasma Pentraxin3 is a novel marker for nonalcoholic steatohepatitis (NASH). BMC Gastroenterol. Nov. 14, 2008;8:53. doi: 10.1186/1471-230X-8-53.
Office action dated Nov. 16, 2015 for U.S. Appl. No. 14/435,121.
Notice of allowance dated Jul. 25, 2016 for U.S. Appl. No. 14/435,121.
Office action dated Apr. 27, 2016 for U.S. Appl. No. 14/435,121.
Office action dated Oct. 6, 2016 for U.S. Appl. No. 13/088,072.
Ahmed, et al., Asian J. Biochem., 2012; 7(1): 16-26.
Anty, R., A new composite model including metabolic syndrome, alanine aminotransferase and cytokeratin-18 for the diagnosis of non-alcoholic steatohepatitis in morbidly obese patients. Aliment Pharmacol Ther. Dec. 2010;32(11-12):1315-22. doi: 10.1111/j.1365-2036.2010.04480.x. Epub Oct. 7, 2010.
Bauer, et al., Connective tissue growth factor level is increased in patients with liver cirrhosis out is not associated with complications or extent of liver injury. Regulatory peptides. 2012, 179(1-3):10-14.
Brown, TT. et al., Association between systemic inflammation and incident diabetes in HIV-infected patients after initiation of antiretroviral therapy. Diabetes Care. Oct. 2010;33(10):2244-9. doi: 10.2337/dc10-0633. Epub Jul. 27, 2010.
Ciprandi, G. et al., Serum adipsin levels in patients with seasonal allergic rhinitis: preliminary data.Int Immunopharmacol. Nov. 2009;9(12):1460-3. doi: 10.1016/j.intimp.2009.08.004. Epub Aug. 20, 2009.
Florentino, et al., Nonalcoholic fatty liver disease in menopausal women. Arquivos de gastroenterologia. 2013;50(3): p. 180-185.
Gomolka, B. et al., Analysis of omega-3 and omega-6 fatty acid-derived lipid metabolite formation in human and mouse blood samples. Prostaglandins Other Lipid Mediat. Apr. 2011;94(3-4):81-7. doi: 10.1016/j.prostaglandins.2010.12.006. Epub Jan. 12, 2011.
Hosoyamada, K. et al., Fatty liver in men is associated with high serum levels of small, dense low-density lipoprotein cholesterol. Diabetol Metab Syndr. Jul. 18, 2012;4(1):34.
Kalhan, SC. et al., Plasma metabolomic profile in nonalcoholic fatty liver disease. Metabolism. Mar. 2011;60(3):404-13. doi: 10.1016/j.metabol.2010.03.006. Epub Apr. 27, 2010.
Lanfear, DE. et al., Short term effects of milrinone on biomarkers of necrosis, apoptosis, and inflammation in patients with severe heart failure.J Transl Med. Jul. 29, 2009;7:67. doi: 10.1186/1479-5876-7-67.

(56) References Cited

OTHER PUBLICATIONS

Lee, H. et al., Diagnostic Significance of Serum HMGB1 in Colorectal Carcinomas. 2012.PLoS One 7(4): e34318. doi:10.1371/journal.pone.0034318.

Lowe, GDO. et al., Blood viscosity and risk of cardiovascular events: the Edinburgh Artery Study. British Journal of Haematalogy. 1997.96: 168-173.

Nakajima, K. et al., The characteristics of remnant lipoproteins in the fasting and postprandial plasma.Clinica Chimica Acta; International Journal of Clinical Chemistry [2012, 413(13-14):1077-1086].

Office Action dated Jan. 13, 2017 for U.S. Appl. No. 14/914,444.

Office Action dated Dec. 2, 2016 for U.S. Appl. No. 14/209,964.

Rabelo, F. et al., Pro- and anti-inflammatory cytokines in steatosis and steatohepatitis. Obes Surg. Jul. 2010;20(7):906-12. doi: 10.1007/s11695-010-0181-4.

Schmilovitz-Weiss, H. et al., Role of circulating soluble CD40 as an apoptotic marker in liver disease. Mar. 2004, vol. 9, Issue 2, pp. 205-210.

Sumida, Y. et al., Serum thioredoxin levels as a predictor of steatohepatitis in patients with nonalcoholic fatty liver disease. J Hepatol. Jan. 2003;38(1):32-8.

Tavares De Almeida, I. et al., Plasma total and free fatty acids composition in human non-alcoholic steatohepatitis. Jun. 2002. 21(3). 219-223.

Zimmermann, E. et al., C-reactive protein levels in relation to various features of non-alcoholic fatty liver disease among obese patients. J Hepatol. Sep. 2011;55(3):660-5. doi: 10.1016/j.jhep.2010.12.017. Epub Jan. 14, 2011.

European Search Report dated Feb. 8, 2017 for EP Application No. 14852793.0.

Montenegro, et al., Gum Arabic: More than an edible emulsifier, products and applications of biopolymers, ISBN:978-953-51-0226-7, 2012.

Office Action dated Apr. 5, 2017 for U.S. Appl. No. 14/209,964.

Witt, P.M. et al., The incorporation of marine n-3 PUFA into platelets and adipose tissue in pre- and postmenopausal women: a randomised, double-blind, placebo-controlled trial. British journal of nutrition. 104; 2010: 318-325.

EPADEL Capsules 300—An EPA Preparation, Apr. 2011 (7th Version) with Translation, 4 Pages.

Office Action dated Aug. 16, 2017 for U.S. Appl. No. 15/269,134.

\* cited by examiner

| Proportion of responder (n of responder/n of cases) | Placebo | EPA-E 1800mg/day |
|---|---|---|
| All Cases | 32.7% (18/55) | 32.7% (18/55) |
| Non-Diabetes | 27.5% (11/40) | 41.9% (13/31) |
| Non-Diabetes + Mild Diabetes (anti-diabetes agent ≦1) | 27.7% (13/47) | 37.8% (17/45) |

| p value by $\chi$ square test vs. Placebo | EPA-E 1800mg/day |
|---|---|
| All Cases | 1.000 |
| Non-Diabetes | 0.202 |
| Non-Diabetes + Mild Diabetes (anti-diabetes agent ≦1) | 0.301 |

Fig. 1

| Proportion of responder (n of responder/n of cases) | | Placebo | EPA-E 1800mg/day |
|---|---|---|---|
| All Cases | HbA1c=<6.4 | 23.7% (9/38) | 42.1%* (16/38) |
| Non-Diabetes | HbA1c=<6.4 | 22.9% (8/35) | 46.4%** (13/28) |

$\chi$ square test vs. Placebo     *: p<0.10     **: p<0.05

| p value by $\chi$ square test vs. Placebo | | EPA-E 1800mg/day |
|---|---|---|
| All Cases | HbA1c=<6.4 | 0.087* |
| Non-Diabetes | HbA1c=<6.4 | 0.049** |

Fig. 2

| Proportion of responder (n of responder/n of cases) | | Placebo | EPA-E 1800mg/day |
|---|---|---|---|
| All Cases | Glucose=<125 | 25.6% (11/43) | 36.2% (17/47) |
| Diabetes | Glucose=<125 | 0.0% (0/5) | 22.2% (4/18) |
| Non-Diabetes | Glucose=<125 | 28.9% (11/38) | 44.8% (13/29) |

| p value by $\chi$ square test vs. Placebo | | EPA-E 1800mg/day |
|---|---|---|
| All Cases | Glucose=<125 | 0.278 |
| Diabetes | Glucose=<125 | 0.246 |
| Non-Diabetes | Glucose=<125 | 0.179 |

Fig. 3

| Proportion of responder (n of responder/n of cases) | | Placebo | EPA-E 1800mg/day |
|---|---|---|---|
| All Cases | HbA1c=<6.4 and Glucose=<125 | 22.9% (8/35) | 43.2%* (16/37) |
| Diabetes | HbA1c=<6.4 and Glucose=<125 | 0.0% (0/2) | 33.3% (3/9) |
| Non-Diabetes | HbA1c=<6.4 and Glucose=<125 | 24.2% (8/33) | 46.4%* (13/28) |

$\chi$ square test vs.Placebo      *: p<0.10

| p value by $\chi$ square test vs. Placebo | | EPA-E 1800mg/day |
|---|---|---|
| All Cases | HbA1c=<6.4 and Glucose=<125 | 0.067* |
| Diabetes | HbA1c=<6.4 and Glucose=<125 | 0.338 |
| Non-Diabetes | HbA1c=<6.4 and Glucose=<125 | 0.069* |

Fig. 4

|  | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| ALT (6-41 U/L) | 10-300 | Lower limit range values of 10, 50, 100, 150, | at least 1% lower | 1 to about 95% reduction |

|  | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| AST (9-34 U/L) | 10-250 | or 200, upper limit range values of 100, 150, 200, 250, or 300, ranges of 10-300, 10-200, 10-150, 10-100, 100-200, 200-300 Lower limit range values of 10, 50, 100, 150, or 200, upper limit range values of 100, 150, 200, 250, or 300, ranges of 10-300, 10-200, 10-150, 10-100, 100-200, 200-300 | at least 1% lower | 1 to about 95% reduction |
| AST/ALT ratio |  | upper limit range values of 0.5, 0.7, 0.8, 1, 1.2, 2, ranges of 0.5-2, 0.5-1, 1-2 |  |  |
| alkaline phosphatase (ALP) (80-260 IU/L) | 80-300 | ranges of 50-800 | no worsening | no worsening, 1 to about 90% reduction, 300 IU/L or less, 250 IU/L or less |
| Total bilirubin (0.2-1.9 mg/dL) |  |  | no worsening | no worsening, 1 to about 90% reduction |
| Gamma-Glutamyl Transferase (GGT or γGTP) (males: 5-60 U/L) |  |  | no worsening | no worsening, 1 to about 90% reduction, 100 U/L or less, 70 U/L or less |
| Albumin (3.8-5.2 g/dL) |  |  | no worsening | no worsening, 1 to about 90% increase, ranges of 3-6 g/dL, 3.8-5.2 g/dL |
| HDL-C (high density lipoprotein cholesterol) (35-80 mg/dL) | less than 55 | less than 60 mg/dL, 55, 50, 45, 40, 35, 30, 25, or 25 mg/dL, ranges of 25-55, 30-80 mg/dL, 40-50 mg/dL, 50-60 mg/dL, at least 60 | no worsening, at least 1% increase | no change, 1-90% increase, 40 mg/dL or more |
| LDL-C (low density lipoprotein cholesterol) (50-130 mg/dL) | 100-200 | at least 70 mg/dL, 100, 125, 130, 140, 150, 170, 180, or 200 or a range of 70-200, 70-250, 70-200, 100-250, 100-200, 130-200, 140-180, 100-150, 130-160, 160-190 | no worsening | no change, 1-90% reduction, less than 160 mg/dL, 140, 130, 120, 100, 70 mg/dL |

Fig. 5

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| Triglycerides (TG) (fed or fasting, 50-150 mg/dl) | 100-1000 | at least 80 mg/dl, 100, 150, 180, 200, 300, 500, 700, 1000, 1200, or 1500, or less than 150, or a range of 100-2500, 100-1500, 100-1000, 150-500, 200-500, 150-300, 150-200, 200-500 | at least 1% lower | 1 to about 90% reduction, 500 mg/dl or less, 300, 200, 150, 100 mg/dl or less |
| Total Cholesterol (TC) (100-200 mg/dl) | 170-300 | a range of 130-300 mg/dl, 200-220, 220-240, 240-260, or at least 260, or less than 200 mg/dl | no worsening | no change, 1-90% reduction |
| TG and HDL-C | High TG and low HDL-C (ex. TG ≥ 150 mg/dl and HDL ≤ 40 mg/dl) | TG: at least 150, 200, 500 mg/dl; HDL-C: less than 40, 50 mg/dl | no worsening | |
| TG/HDL-C ratio | at least 3.75 | at least 2, 2.5, 3, 2.75, 4, 5, 10, or ranges of 2-3.75, 3.75-10 | at least 1% lower | no worsening, at least 1% lower, or 1-90% reduction |
| Non-HDL-C (mg/dl) | at least 130 | at least 100 mg/dl, 130, 150, 160, 170, 190, a range of 100 to 250 | no worsening | no worsening, or at least 1% lower, or less than 130 mg/dl, 150, 160, 170, 190 |
| Free fatty acid (µEq/l) (140-850) | at least 400 | less than 400, at least 400, 600, 800, 1000 | at least 1% lower | no change, or at least 1 to 90% reduction |
| Eicosapentaenoic Acid/Arachidonic Acid (EPA/AA) (ex. (mol%)/(mol%)) | less than 0.3 low compared to average level of normal subjects | less than 1, 0.75, 0.5, 0.1, ranges of 0.01-2 | at least 5% increase | 5 to about 200% increase, about 2-200-fold increase |
| Arachidonic Acid (AA) (ex. mol%) | High compared to average level of normal subjects | | at least 1% lower | no change, 1 to about 90% reduction |
| Eicosapentaenoic Acid (EPA) (ex. mol%) | low compared to average level of normal subjects | | at least 5% increase | 5 to about 200% increase, about 2-500-fold increase |
| Docosapentaenoic Acid (DPA) (ex. mol%) | low compared to average level of normal subjects | | at least 1% increase | 1 to about 90% increase |
| Docosahexaenoic Acid (DHA) (ex. mol%) | low compared to average level of normal subjects | | | |
| DPA/AA ratio | low compared to average level of normal subjects | | | |

Fig. 5 (continued)

| | Pre-treatment baseline | | After dosing (effect values) | |
|---|---|---|---|---|
| Item (Typical Normal Values, Units) | Typical Range(s) | Observable Ranges or Values | Typical Range(s) | Observable Ranges or Values |
| DPA/AA ratio | low compared to average level of normal subjects | | | |
| DHA/DPA ratio | low compared to average level of normal subjects | | | |
| Monounsaturated fatty acid (MUFA) (ex. mol%) | High compared to average level of normal subjects | | at least 1% lower | no change, at least 1% lower |
| Palmitoleic acid (16:3 n7) (ex. mol%) | High compared to average level of normal subjects | | at least 1% lower | no change, at least 1% lower |
| Oleic acid (18:1 n9) (ex. mol%) | High compared to average level of normal subjects | | at least 1% lower | no change, at least 1% lower |
| Oleic acid (18:1 n9)/ stearic acid (18:0) ratio | High compared to average level of normal subjects | | at least 1% lower | no change, at least 1% lower |
| Palmitoleic acid (16:1)/ Palmitic acid (16:0) ratio | High compared to average level of normal subjects | | at least 1% lower | no change, at least 1% lower |
| Stearic acid (18:0)/ Palmitic acid (16:0) ratio | High compared to average level of normal subjects | | no change, or at least 1% lower | no change, or at least 1% lower |
| γ-linoleic acid (18:3 n6)/ Linoleic acid (18:2 n6) ratio | High compared to average level of normal subjects | | no change, or at least 1% lower | no change, or at least 1% lower |
| AA/Homo-γ-linolenic acid (20:3 n6) ratio | low compared to average level of normal subjects | | no change, or at least 1% increase | no change, or at least 1% increase |
| Adrenic acid (22:4 n6)/ AA ratio | High compared to average level of normal subjects | | no change, or at least 1% lower | no change, or at least 1% lower |
| Ferritin (ng/mL) | | at least 100, 150, 180, 200, 250, 300, 350, 400, or 500 | at least 1% lower | at least 1 to about 95% lower |
| Thioredoxin (ng/mL) | | at least 15, 20, 25, 30, 35, 40, 45, or 50 | at least 1% lower | at least 1 to about 95% lower |
| TNFα (pg/mL) (1.79 or less) | at least 1.5 | at least 1, 1.5, 1.6, 1.7, 1.79, 1.8, 1.9, 2.0, 2.2, 2.5, 3, 3.5, 4, 5, 6, 7 or 10 | at least 1% lower | at least 1 to about 95% lower |

Fig. 5 (continued)

|  | Pre-treatment baseline | | After dosing (effect) values | |
| --- | --- | --- | --- | --- |
| Item (Typical Normal Values, Units) | Typical Range(s) | Observable Ranges or Values | Typical Range(s) | Observable Ranges or Values |
| sTNF-R1 (pg/mL) |  | at least 400, 500, 600, 700, 800, 900, 1000, 1100, 1200, 1500, or 2000 | at least 1% lower | at least 1 to about 95% lower |
| sTNF-R2 (pg/mL) |  | at least 500, 700, 1000, 1200, 1500, 1700, 2000, 2300, 2500, 2700, or 3000 | at least 1% lower | at least 1 to about 95% lower |
| High Sensitivity C-reactive protein (Hs-CRP, mg/dl) | 0.3 | 0.1 or more, 0.2, 0.3, 0.4, 0.5 or more, ranges of 0.1-1, 0.1-0.8, 0.1-0.5, 0.2-0.5 | at least 1% lower | at least 5 to about 95% lower |
| Connective Tissue Growth Factor (CTGF) |  |  | at least 1% lower | at least 1 to about 95% lower |
| Serum Soluble CD40 (sCD40, pg/ml) |  | 5 pg/ml or more, 10, 20, 30, 50, 70, 100, 120, 150, 170, 200, 220, 250, 300, 350, 400, 450, 500 or more | at least 1% lower | at least 5 to about 95% lower |
| Insulin resistance Index (HOMA-IR) (1.6 or less) | 1.5 or more | 1.6 or less/1.5 or more, 1.6, 2, 2.5, 3, 3.5, 4 | no worsening | no change, at least 1 to about 50% lower |
| Glycated hemoglobin (HbA1c) (4.3-5.8%) | 5.7 or more | a range of 4.3-5.8, 5.7-6.4, 5.8-6.5, 6.5-7.0, 7.0-8.0/5.7 or more, 5.8, 6, 6.5, 7, 7.5, 8, or 8.5 | no worsening | no change, at least 1 to about 50% lower |
| Fasting plasma glucose (FPG) (mg/dl) (less than 100) | 100 or more | less than 100/ 100 or more, 110, 120, 126, 150, 180, 200, 250, 300/ ranges of 100-110, 100-126 | no worsening | no change, or at least 1 to about 50% lower |
| Postprandial plasma glucose (after a meal) | 140 or more | less than 140, 160, 200/ 140 or more, 170, 180, 200, 250, 300, 350, 400/ranges of 140-200, 140-170, 170-200 | no worsening | no change, or at least 1 to about 50% lower |
| two-hour glucose levels on the 75-g oral glucose tolerance test (mg/dl) (OGTT) | 140-200 | less than 140, 160, 200/140 or more, 170, 180, 200, 250, 300, 350, 400/ ranges of 140-200, 140-170, 170-200 | no worsening | no change, or at least 1 to about 50% lower |
| Leptin (ng/ml) |  | 5 ng/ml or more, 10, 12, 15, 17, 20, 22, 25, 30, 35, 40 or more | at least 1% lower | at least 1 to about 95% reduction |

Fig. 5 (continued)

|  | Pre-treatment baseline | | After dosing (effect) values | |
| --- | --- | --- | --- | --- |
| Item (Typical Normal Values, Units) | Typical Range(s) | Observable Ranges or Values | Typical Range(s) | Observable Ranges or Values |
| Serum adiponectin (μg/mL) | | 5 μg/mL or less, 4.5, 4, 3.5, or 3 μg/mL or less | at least 1% increase | no change, at least 1 to about 95% increase |
| complement factor D | | | at least 1% lower | at least 1 to about 95% reduction |
| CK18 fragment | | | at least 1% lower | at least 1 to about 95% reduction |
| serum High mobility group box 1 protein (HMGB1) | | | at least 1% lower | at least 1 to about 95% reduction |
| Fas | | | at least 1% lower | at least 1 to about 95% reduction |
| Hyaluronic acid (50 ng/mL or less) | | 25 ng/mL or more, 50, 75, 100, 120, 150, 200, 250, or 300 or more; 300 mL or less, 100, 70, or 50 or less | at least 1% lower | at least 1 to about 95% reduction |
| Type IV collagen (7s domain) (6 ng/mL or less) | | 5 ng/mL or more, 6, 7, 8, 10, 12, 15, or 20 or more; 25 ng/mL or less, 20, 15, 10, or 6 or less | at least 1% lower | at least 1 to about 95% reduction |
| procollagen III peptide 0.3-0.8 U/ml | | 0.2 U/ml or more, 0.3, 0.5, 0.7, 1, 1.2, 1.5, 2, 2.5, 3, 3.5, or 4 or more; 10 or less, 8, 5, 3, 1, or 0.8 or less | at least 1% lower | at least 1 to about 95% reduction |
| PAI-1 (ng/mL) 50 or less | 50 or more | | | |
| | | Items other than serum | | |
| platelet count 150000-400000/μl | 150000-300000 | 400000/μl or less, 300000, 200000/a range of 150000-300000 | no change | no change, at least 1% increase |
| BMI | 18.5-40 | 18.5 or more, 20, 25, 30, 35, 40, or 50 or more; 50 or less, 40, 30, 25, 20 or 18.5 or less; or range of 18.5-25, 25-30, 30-35, 35-40 | no change | no change, at least 1% reduction |

Fig. 5 (continued)

| Proportion of responder (n of responder/n of cases) | All Cases | Placebo | EPA-E 1800mg/day | EPA-E 2700mg/day |
|---|---|---|---|---|
| All Cases | 32.2% (56/174) | 32.7% (18/55) | 32.7% (18/55) | 31.3% (20/64) |
| GGT≦33 | 41.9% (13/31) | 23.1% (3/13) | 45.5% (5/11) | 71.4%* (5/7) |
| GGT>33 | 30.1% (43/143) | 35.7% (15/42) | 29.5% (13/44) | 26.3% (15/57) |

χ square test vs Placebo    *: p<0.05

| p value by χ square test vs. Placebo | All Cases | Placebo | EPA-E 1800mg/day | EPA-E 2700mg/day |
|---|---|---|---|---|
| All Cases | - | - | 1.000 | 0.863 |
| GGT≦33 | - | - | 0.247 | 0.035* |
| GGT>33 | - | - | 0.542 | 0.315 |

Fig. 7

| Primary endpoint achieved rate (n of achieved/n of cases) | Placebo | EPA-E 1800mg/day | EPA-E 2700mg/day |
|---|---|---|---|
| GGT=<24,25,26 or 27 | 12.5% (1/8) | 50.0% (2/4) | 60.0%* (3/5) |
| GGT=<28 | 12.5% (1/8) | 40.0% (2/5) | 60.0%* (3/5) |
| GGT=<29 | 12.5% (1/8) | 33.3% (2/6) | 66.7%** (4/6) |
| GGT=<30 | 11.1% (1/9) | 33.3% (2/6) | 66.7%** (4/6) |
| GGT=<31 | 10.0% (1/10) | 28.6% (2/7) | 66.7%** (4/6) |
| GGT=<32 | 16.7% (2/12) | 33.3% (3/9) | 66.7%** (4/6) |
| GGT=<33 | 23.1% (3/13) | 45.5% (5/11) | 71.4%** (5/7) |
| GGT=<34 | 23.1% (3/13) | 41.7% (5/12) | 62.5%* (5/8) |
| GGT=<35 | 23.1% (3/13) | 41.7% (5/12) | 55.5% (5/9) |
| GGT=<40 | 27.8% (5/18) | 38.9% (7/18) | 46.7% (7/15) |
| GGT=<45 | 27.8% (5/18) | 40.9% (9/22) | 33.3% (8/24) |
| GGT=<50 | 28.6% (6/21) | 38.5% (10/26) | 32.1% (9/28) |
| GGT=<55 | 30.4% (7/23) | 35.5% (11/31) | 31.3% (10/32) |
| GGT=<60 | 28.0% (7/25) | 36.4% (12/33) | 31.3% (10/32) |
| GGT male=<30, female=<24 | 11.1% (1/9) | 33.3% (2/6) | 60.0%* (3/5) |

Fig. 8

| χ square test vs.Placebo | | *: p<0.10 | **: p<0.05 |
|---|---|---|---|
| p value by χ square test vs. Placebo | Placebo | EPA-E 1800mg/day | EPA-E 2700mg/day |
| GGT=<24,25,26 or 27 | - | 0.157 | 0.071* |
| GGT=<28 | - | 0.252 | 0.071* |
| GGT=<29 | - | 0.347 | 0.036** |
| GGT=<30 | - | 0.292 | 0.025** |
| GGT=<31 | - | 0.323 | 0.018** |
| GGT=<32 | - | 0.375 | 0.034** |
| GGT=<33 | - | 0.247 | 0.035** |
| GGT=<34 | - | 0.319 | 0.071* |
| GGT=<35 | - | 0.319 | 0.119 |
| GGT=<40 | - | 0.480 | 0.261 |
| GGT=<45 | - | 0.386 | 0.700 |
| GGT=<50 | - | 0.477 | 0.788 |
| GGT=<55 | - | 0.697 | 0.949 |
| GGT=<60 | - | 0.502 | 0.790 |
| GGT male=<30, female=<24 | - | 0.292 | 0.052* |

Fig. 8 (continued)

| Change of NAS score mean±SD (n) | Placebo | EPA-E 1800mg/day | EPA-E 2700mg/day |
|---|---|---|---|
| All Cases | 0.927±1.500 (55) | 1.018±1.258 (55) | 0.844±1.573 (64) |
| GGT≦33 | 0.769±1.527 (13) | 1.818±1.029* (11) | 2.286±1.248* (7) |
| GGT>33 | 0.976±1.476 (42) | 0.818±1.230 (44) | 0.667±1.514 (57) |

Student's t test vs Placebo    *: p<0.05

| p value by student's t test vs. Placebo | Placebo | EPA-E 1800mg/day | EPA-E 2700mg/day |
|---|---|---|---|
| All Cases | - | 0.367 | 0.385 |
| GGT≦33 | - | 0.039* | 0.024* |
| GGT>33 | - | 0.298 | 0.159 |

Fig. 9

| EPA/AA ratio at Day365 mean±SD (n) | Placebo | EPA-E 1800mg/day | EPA-E 2700mg/day |
|---|---|---|---|
| All Cases | 0.076±0.080 (46) | 0.311±0.206 (51) | 0.557±0.374 (56) |
| GGT≦33 | 0.124±0.165 (8) | 0.313±0.192 (11) | 1.026±0.488* (7) |
| GGT>33 | 0.077±0.080 (38) | 0.383±0.251 (40) | 0.507±0.326 (49) |

Student's t test vs GGT>33    *: $p<0.05$

| p value by student's t test | Placebo | EPA-E 1800mg/day | EPA-E 2700mg/day |
|---|---|---|---|
| GGT≦33 vs GGT>33 | 0.070 | 0.202 | 0.0004* |

Fig. 10

| Parameter (Baseline) | Group | GGT=<33 | GGT>33 | Stedman [a] | Merck Manual [b] |
|---|---|---|---|---|---|
| GGT (U/L) | Placebo | 24.4±6.4 | 102.9±71.5 | M:2-30 F:1-24 | 8-78 |
| | 1800 | 27.8±4.7 | 98.0±125.2 | | |
| | 2700 | 23.3±6.4 | 95.4±111.9 | | |
| ALP (U/L) | Placebo | 62.8±13.1 | 93.7±38.9 | - | 36-92 |
| | 1800 | 71.1±17.0 | 82.1±24.9 | | |
| | 2700 | 76.3±20.8 | 90.1±25.9 | | |
| Direct Bilirubin (mg/dL) | Placebo | 0.09±0.03 | 0.11±0.05 | 0-0.4 | 0-0.3 |
| | 1800 | 0.11±0.03 | 0.10±0.05 | | |
| | 2700 | 0.11±0.05 | 0.11±0.05 | | |
| ALT (U/L) | Placebo | 47.4±22.9 | 96.0±48.9 | M:13-40 F:10-28 | 0-35 |
| | 1800 | 51.5±28.4 | 94.0±51.9 | | |
| | 2700 | 86.4±79.2 | 81.6±34.8 | | |

Fig. 11 a) Stedmansonline Laboratory Reference Range Values
b) Merck Manual Appendix II Normal Laboratory Values

| Parameter (Baseline) | Group | GGT=<33 | GGT>33 | Stedman [a] | Merck Manual [b] |
|---|---|---|---|---|---|
| AST (U/L) | Placebo | 35.0±12.9 | 69.3±44.2 | 10-59 | 0-35 |
| | 1800 | 36.1±16.1 | 68.6±38.9 | | |
| | 2700 | 66.7±63.7 | 61.1±32.4 | | |
| Albumin(g/dL) | Placebo | 4.52±0.38 | 4.53±0.62 | 3.5-5.2 (>60y:3.2-4.6) | 3.5-5.5 |
| | 1800 | 4.47±0.29 | 4.56±0.27 | | |
| | 2700 | 4.66±0.18 | 4.53±0.29 | | |
| Ferritin (ng/mL) | Placebo | 76.0±51.6 | 253.3±221.4 | M:20-150 F:10-120 | 15-200 |
| | 1800 | 134.7±96.1 | 239.6±264.1 | | |
| | 2700 | 151.3±98.5 | 234.9±159.4 | | |
| CK18 Fragment (U/L) | Placebo | 428.5±229.1 | 928.5±839.5 | | - |
| | 1800 | 357.7±174.8 | 811.5±665.7 | | |
| | 2700 | 546.7±368.4 | 798.0±673.5 | | |

Fig. 11 (continued)

| Proportion of responder (n of responder/n of cases) | Placebo | EPA-E 1800mg/day |
|---|---|---|
| All Cases | 32.7% (18/55) | 34.0% (18/53) |
| sFas≦9.5 | 33.3% (3/9) | 80.0%** (8/10) |
| sFas>9.5 | 32.6% (15/46) | 23.3 (10/43) |

$\chi$ square test vs Placebo  **: $p<0.05$

| p value by $\chi$ square test vs. Placebo | Placebo | EPA-E 1800mg/day |
|---|---|---|
| All Cases | - | 0.892 |
| sFas≦9.5 | - | 0.040** |
| sFas>9.5 | - | 0.327 |

Fig. 14

| χ square test vs Placebo | *:p<0.10 | **:p<0.05 |

| Proportion of responder (n of responder/n of cases) | Placebo | EPA-E 1800mg/day |
|---|---|---|
| sFas=<10.0 | 36.4% (4/11) | 61.5% (8/13) |
| sFas=<9.9 | 36.4% (4/11) | 61.5% (8/13) |
| sFas=<9.8 | 40.0% (4/10) | 61.5% (8/13) |
| sFas=<9.7 | 40.0% (4/10) | 72.7% (8/11) |
| sFas=<9.6 | 40.0% (4/10) | 72.7% (8/11) |
| sFas=<9.5 | 33.3% (3/9) | 80.0%** (8/10) |
| sFas=<9.4 | 37.5% (3/8) | 88.9%** (8/9) |
| sFas=<9.3 | 37.5% (3/8) | 87.5%** (7/8) |
| sFas=<9.2 | 42.9% (3/7) | 100.0%** (5/5) |
| sFas=<9.1 | 50.0% (3/6) | 100.0%* (5/5) |
| sFas=<9.0 | 50.0% (3/6) | 100.0%* (5/5) |
| sFas=<8.9 | 50.0% (3/6) | 100.0%* (4/4) |
| sFas=<8.8 | 50.0% (3/6) | 100.0%* (4/4) |
| sFas=<8.7 | 50.0% (3/6) | 100.0% (3/3) |

Fig. 15

χ square test vs.Placebo     *:p<0.10     **:p<0.05

| p value by χ square test vs. Placebo | Placebo | EPA-E 1800mg/day |
|---|---|---|
| sFas=<10.0 | - | 0.219 |
| sFas=<9.9 | - | 0.219 |
| sFas=<9.8 | - | 0.305 |
| sFas=<9.7 | - | 0.130 |
| sFas=<9.6 | - | 0.130 |
| sFas=<9.5 | - | 0.040** |
| sFas=<9.4 | - | 0.027** |
| sFas=<9.3 | - | 0.039** |
| sFas=<9.2 | - | 0.038** |
| sFas=<9.1 | - | 0.064* |
| sFas=<9.0 | - | 0.064* |
| sFas=<8.9 | - | 0.091* |
| sFas=<8.8 | - | 0.091* |
| sFas=<8.7 | - | 0.134 |

Fig. 15 (continued)

| Change of NAS score mean±SD (n) | Placebo | EPA-E 1800mg/day |
|---|---|---|
| All Cases | 0.927±1.500 (55) | 1.057±1.265 (53) |
| sFas≦9.5 | 1.000±1.491 (9) | 2.200±0.872** (10) |
| sFas>9.5 | 0.913±1.501 (46) | 0.791±1.192 (43) |

Student's t test vs Placebo  **:p<0.05

| p value by student's t test vs. Placebo | Placebo | EPA-E 1800mg/day |
|---|---|---|
| All Cases | - | 0.316 |
| sFas≦9.5 | - | 0.028** |
| sFas>9.5 | - | 0.338 |

Fig. 16

| Proportion of responder (n of responder/n of cases) | Placebo | EPA-E 1800mg/day |
|---|---|---|
| M30=<1500 | 26.7% (12/45) | 31.9% (15/47) |
| M30=<1000 | 26.7% (12/45) | 34.9% (15/43) |
| M30=<900 | 21.4% (9/42) | 34.9% (15/43) |
| M30=<800 | 23.7% (9/38) | 33.3% (14/42) |
| M30=<700 | 25.0% (9/36) | 32.4% (12/37) |
| M30=<600 | 26.6% (8/30) | 35.5% (11/31) |
| M30=<500 | 25.9% (7/27) | 45.5% (10/22) |

| p value by $\chi$ square test vs. Placebo | Placebo | EPA-E 1800mg/day |
|---|---|---|
| M30=<1500 | - | 0.581 |
| M30=<1000 | - | 0.403 |
| M30=<900 | - | 0.168 |
| M30=<800 | - | 0.341 |
| M30=<700 | - | 0.483 |
| M30=<600 | - | 0.433 |
| M30=<500 | - | 0.153 |

Fig. 17

Student's t test vs Placebo    *:p<0.10    **:p<0.05

| Proportion of responder (n of responder/n of cases) | | Placebo | EPA-E 1800mg/day | EPA-E 2700mg/day |
|---|---|---|---|---|
| sFas=<10.0 | M30≦1500 | 27.3 (3/11) | 58.3 % (7/12) | 47.1 % (8/17) |
| | M30≦600 | 30.0% (3/10) | 66.6 % (6/9) | 50.0 % (6/12) |
| | M30≦500 | 25.0% (2/8) | 66.6 %* (6/9) | 55.5 % (5/9) |
| sFas=<9.7 | M30≦1500 | 33.3% (3/9) | 70.0 % (7/10) | 61.5% (8/13) |
| | M30≦600 | 37.5% (3/8) | 66.6 % (6/9) | 75.0 % (6/8) |
| | M30≦500 | 33.3% (2/6) | 66.6 % (6/9) | 83.3 %* (5/6) |
| sFas=<9.6 | M30≦1500 | 33.3% (3/9) | 77.8 %* (7/9) | 66.7 % (8/12) |
| | M30≦600 | 37.5% (3/8) | 75.0 % (6/8) | 75.0 % (6/8) |
| | M30≦500 | 33.3% (2/6) | 75.0 % (6/8) | 83.3 %* (5/6) |
| sFas=<9.5 | M30≦1500 | 25.0% (2/8) | 77.8 %** (7/9) | 66.7 %* (8/12) |
| | M30≦600 | 28.6% (2/7) | 75.0 %* (6/8) | 75.0 %* (6/8) |
| | M30≦500 | 20.0% (1/5) | 75.0 %* (6/8) | 83.3 %** (5/6) |

Fig. 18

| χ square test vs.Placebo | | *:p<0.10 | **:p<0.05 | |
|---|---|---|---|---|
| p value by χ square test vs. Placebo | | Placebo | EPA-E 1800mg/day | EPA-E 2700mg/day |
| sFas=<10.0 | M30≦1500 | - | 0.133 | 0.295 |
| | M30≦600 | - | 0.110 | 0.342 |
| | M30≦500 | - | 0.086 * | 0.201 |
| sFas=<9.7 | M30≦1500 | - | 0.110 | 0.193 |
| | M30≦600 | - | 0.229 | 0.131 |
| | M30≦500 | - | 0.205 | 0.079 * |
| sFas=<9.6 | M30≦1500 | - | 0.058 * | 0.130 |
| | M30≦600 | - | 0.131 | 0.131 |
| | M30≦500 | - | 0.119 | 0.079 * |
| sFas=<9.5 | M30≦1500 | - | 0.030 ** | 0.068 * |
| | M30≦600 | - | 0.072 * | 0.072 * |
| | M30≦500 | - | 0.053 * | 0.036 ** |

Fig. 18 (continued)

Further Characterization of Patient Group 3: Risk Score※
Proportion of responder of Primary Endpoint
(NAS score $\leq$ 3 or improve $\geq$ 2 across at least 2 of NAS components)

| Proportion of responder (n of responder/n of cases) | Placebo | EPA-E 1800mg/day |
|---|---|---|
| Risk Score=<4.000 | 25.0 % (8/32) | 40.6% (13/32) |
| Risk Score=<3.000 | 27.6 % (8/29) | 50.0 %* (12/24) |
| Risk Score=<2.859 | 29.6 % (8/27) | 47.8% (11/23) |

$\chi$ square test vs. Placebo   *: p<0.10

| p value by $\chi$ square test vs. Placebo | Placebo | EPA-E 1800mg/day |
|---|---|---|
| Risk Score=<4.000 | - | 0.183 |
| Risk Score=<3.000 | - | 0.094* |
| Risk Score=<2.859 | - | 0.186 |

The regression formula for prediction of presence of NASH based on sFas and M30
Risk Score=-6.4894+0.0078×M30(U/L)+0.4668×sFas(ng/mL)

(Tamimi TI., et.al., J. Hepatol., 54, 1224-1229, 2011)

Fig. 19

| Parameter (Baseline) | Group | sFas=<9.5 | sFas>9.5 | Tamimi TI., et.al [a] |
|---|---|---|---|---|
| sFas (ng/mL) | Placebo | 8.3±0.9 | 13.2±2.0 | Median (25th,75th percentile) NASH: 11.8 (7.8,12.5) Not NASH: 5.9 (4.8,8.3) |
| | 1800 | 8.5±1.4 | 13.2±4.1 | |
| | 2700 | 8.8±0.5 | 12.7±3.1 | |
| M30 (U/L) | Placebo | 537±419 | 862±902 | Range:60-2306 Median (25th,75th percentile) NASH: 508 (280,846) Not NASH: 176 (131,224) |
| | 1800 | 562±642 | 753±616 | |
| | 2700 | 602±350 | 813±702 | | a) Tamimi TI., et.al., J. Hepatol., 54, 1224-1229, 2011

Fig. 20

| EPA/AA ratio at Day365 mean±SD (n) | Placebo | EPA-E 1800mg/day | EPA-E 2700mg/day |
|---|---|---|---|
| All Cases | 0.086±0.080 (46) | 0.362±0.240 (50) | 0.572±0.390 (56) |
| sFas≦9.5 | 0.056±0.012 (4) | 0.458±0.322* (9) | 0.731±0.442* (10) |
| sFas>9.5 | 0.088±0.084 (42) | 0.341±0.212 (41) | 0.537±0.369 (46) |

Student's t test vs sFas>9.5    * p<0.10

| p value by student's t test | Placebo | EPA-E 1800mg/day | EPA-E 2700mg/day |
|---|---|---|---|
| sFas≦9.5 vs sFas>9.5 | 0.227 | 0.097* | 0.080* |

Fig. 22

COMPOSITIONS AND METHODS FOR TREATING NON-ALCOHOLIC STEATOHEPATITIS

CROSS-REFERENCE

This application claims the benefit of U.S. Provisional Application No. 61/791,533, filed Mar. 15, 2013; 61/793,309, filed Mar. 15, 2013; and 61/817,796, filed Apr. 30, 2013, each of which applications is incorporated herein in its entirety by reference.

BACKGROUND

Heavy alcohol use is known to lead to liver complications, including alcoholic hepatitis which is often characterized by fatty liver and inflammation. Alcoholic hepatitis can ultimately lead to cirrhosis of the liver (scarring) and hardening of the liver tissue. However, individuals that do not consume excessive amounts of alcohol can also be found to have liver disease complications. Non-alcoholic fatty liver disease (NAFLD) is understood to encompass a variety of liver diseases, including steatosis (simple fatty liver), non-alcoholic steatohepatitis (NASH) and advanced scarring of the liver (cirrhosis). NASH has traditionally been diagnosed by means of a liver biopsy to characterize the liver histology, particularly with respect to the characteristics of inflammation, fibrosis and steatosis (fat accumulation). NASH then generally refers to clinical findings based upon the liver biopsy of a patient with steatohepatitis, combined with the absence of significant alcohol consumption (Neuschwander-Tetri, B. A. and S. H. Caldwell (2003) Hepatology 37(5): 1202-1209).

In NASH, fat accumulation is seen in varying degrees of inflammation (hepatitis) and may lead to more serious conditions involving scarring (fibrosis). Patients having NASH are also often characterized by abnormal levels of liver enzymes, such as aspartate aminotransferase (AST) and alanine aminotransferase (ALT). Currently, there are few therapies to slow down or alter the course of further disease progression in NASH. Therefore, there remains a need for effective NASH treatments.

SUMMARY OF THE DISCLOSURE

The disclosure provides for a method for treating a fatty liver disease or disorder in a subject in need thereof, comprising selecting a subject having or suspected of having a fatty liver disease or disorder, wherein the subject is non diabetic, pre-diabetic, or mildly diabetic; or has normal or substantially normal biliary tract function; or has non or early stage hepatocyte apoptosis; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the present disclosure provides for a method for treating a fatty liver disease or disorder in a subject in need thereof, comprising selecting a subject having or suspected of having a fatty liver disease or disorder, wherein the subject is non diabetic, pre-diabetic, or mildly diabetic and undergoing medical nutrition therapy and/or physical exercise; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases the EPA-E or EPA present may be at least 40% by weight in total of the fatty acids and their derivatives.

In some embodiments, the present disclosure provides for a method for treating a fatty liver disease or disorder in a subject in need thereof, comprising selecting a subject having or suspected of having a fatty liver disease or disorder, wherein the subject presents non or early stage hepatocyte apoptosis or serum or plasma soluble Fas (sFas) or serum or plasma cytokeratin-18 fragment M30 (M30) levels associated with non or early stage hepatocyte apoptosis or is considered to have a NASH risk score of 3.0 or lower; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases the EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject presents non or early stage hepatocyte apoptosis or sFas levels equal to or less than 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL, preferably equal to or less than 9.5 ng/mL, and/or M30 levels equal to or less than 1500, 1400, 1300, 1200, 1100, 1000, 900, 800, 700, 600, or 500 U/L, preferably equal to or less than 900 U/L, more preferably equal to or less than 500 U/L, or a NASH risk score equal to or less than 3.0, 2.9, 2.859, 2.8, 2.7, 2.6, 2.5, 2.4, 2.3, 2.2, 2.1 or 2.0, preferably equal to or less than 3.0, and administering a therapeutically effective amount of a pharmaceutical composition comprising ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject presents non or early stage hepatocyte apoptosis or sFas levels equal to or less than 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL, preferably equal to or less than 9.5 ng/mL, and/or M30 levels equal to or less than 1500, 1400, 1300, 1200, 1100, 1000, 900, 800, 700, 600, or 500 U/L, preferably equal to or less than 900 U/L, more preferably equal to or less than 500 U/L, or a NASH risk score equal to or less than 3.0, 2.9, 2.859, 2.8, 2.7, 2.6, 2.5, 2.4, 2.3, 2.2, 2.1 or 2.0, preferably equal to or less than 3.0, and administering a therapeutically effective amount of a pharmaceutical composition comprising ethyl eicosapentanoate (EPA-E), eicosapentaenoic acid (EPA) and its pharmaceutically acceptable amides, salts, esters and phospholipids; (b) improving the steatosis and lobular inflammation condition of said subject, and no worsening of said fibrosis stage score; and (c) the subject exhibits the following changes in said at least one marker as compared to a baseline pretreatment level of at least 1% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Stearic acid/Palmitic acid ratio, γ-linoleic acid/Linoleic acid ratio, Adrenic acid/AA ratio, Ferritin, Thioredoxin, TNF α, sTNF-R1, sTNF-R2, Hs-CRP, CTGF, sCD40, Leptin, complement factor D, CK18 fragment, serum HMGB1, Fas, Hyaluronic acid, Type IV collagen (7s domain), procollagen III peptide or PAI-1; at least 5% increase for EPA or EPA/AA ratio; at least 1% increase for DPA, AA/Homo-γ-linoleic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count or BMI.

In some embodiments, the disclosure provides for a method for treating a fatty liver disease or disorder in a subject in need thereof, comprising: selecting a subject where at least one criteria selected from the group consisting of NAS score, steatosis score, lobular inflammation score, ballooning score and fibrosis stage is indicative of fatty liver disease; and wherein the subject presents non or early stage hepatocyte apoptosis or sFas levels equal to or less than 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL, preferably equal to or less than 9.5 ng/mL, and/or M30 levels equal to or less than 1500, 1400, 1300, 1200, 1100, 1000, 900, 800, 700, 600, or 500 U/L, preferably equal to or less than 900 U/L, more preferably equal to or less than 500 U/L, or a NASH risk score equal to or less than 3.0, 2.9, 2.859, 2.8, 2.7, 2.6, 2.5, 2.4, 2.3, 2.2, 2.1 or 2.0, preferably equal to or less than 3.0, and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

The disclosure also provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level is normal or substantially normal, and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids; and administering in step b results in an improvement of serum EPA/AA ratio as compared to a baseline EPA/AA ratio equal to or greater than 0.1, 0.15, 0.2, 0.25, 0.3, 0.35, or 0.4 in the subject. In some cases EPA-E or EPA present may be at least 40% by weight in total of the fatty acids and their derivatives.

The disclosure also provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level equal to or less than 24, 25, 26, 27, 28, 29, 30, 31, 32, 33, 34, 35, 40, 45, 50, 55, 60 or 78 IU/L, or GGT level equal to or less than 30 or 85 IU/L for men and GGT level equal to or less than 24 or 55 IU/L for women and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; wherein the subject is not treated with an anti-diabetic agent or has been previously treated with an anti-diabetic agent; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level equal to or less than 24, 25, 26, 27, 28, 29, 30, 31, 32, 33, 34, 35, 40, 45, 50, 55, 60 or 78 IU/L, or GGT level equal to or less than 30 or 85 IU/L for men and GGT level equal to or less than 24 or 55 IU/L for women, (a) administering to a subject an effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids; (b) improving the steatosis and lobular inflammation condition of said subject, and no worsening of said fibrosis stage score; and (c) the subject exhibits the following changes in said at least one marker as compared to a baseline pretreatment level of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Stearic acid/Palmitic acid ratio, γ-linoleic acid/Linoleic acid ratio, Adrenic acid/AA ratio, Ferritin, Thioredoxin, TNF α, sTNF-R1, sTNF-R2, Hs-CRP, CTGF, sCD40, Leptin, complement factor D, CK18 fragment, serum HMGB1, Fas, Hyaluronic acid, Type IV collagen (7s domain), procollagen III peptide or PAI-1; at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 200, 250, 300, 350, 400, 450, 500, 600, 700, 800, 900, 1000, 1500, 2000, 3000, 4000, 5000% increase for EPA or EPA/AA ratio; at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 200, 250, 300, 350, 400, 450, 500% increase for DPA, AA/Homo-γ-linoleic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count, sFas, M30, NASH risk score or BMI.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids in combination with one or more anti-diabetic agents.

In some embodiments, the disclosure provides for a method for treating a fatty liver disease or disorder in a subject in need thereof, comprising: selecting a subject where at least one criteria selected from the group consisting of NAS score, steatosis score, lobular inflammation score, ballooning score and fibrosis stage is indicative of fatty liver disease; and wherein the subject shows a serum gamma glutamyl transferase (GGT) level equal to or less than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids. In some cases EPA-E or EPA present may be at least 40% by weight in total of the fatty acids and their derivatives.

In some embodiments, the disclosure provides for a method for treating a fatty liver disease or disorder in a subject in need thereof, comprising selecting a subject having a: NAS score greater than or equal to 3; or steatosis score equal to or greater than 1; or lobular inflammation score equal to or greater than 1; or ballooning score equal to or greater than 1; or fibrosis score equal to or greater than 1; administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids to the subject; and wherein the subject's serum HbA1c level is equal to or less than 6.4% or ii) the subject's fasting serum glucose level is equal to or less than 125 mg/dl.

In some embodiments, the disclosure provides for a method for treating a fatty liver disease or disorder in a subject in need thereof, comprising: selecting a subject having a: NAS score greater than or equal to 3; or steatosis score equal to or greater than 1; or lobular inflammation score equal to or greater than 1; or ballooning score equal to or greater than 1; or fibrosis score equal to or greater than 1; determining the subject's sFas or M30 serum level or NASH risk score; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids to the subject, if the i) subject presents non or early stage hepatocyte apoptosis or sFas levels equal to or less than 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL, preferably equal to or less than 9.5 ng/mL, and/or M30 levels equal to or less than 1500, 1400, 1300, 1200, 1100, 1000, 900, 800, 700, 600, 500 U/L, preferably equal to or less than 900 U/L, more preferably equal to or less than 500 U/L, or a NASH risk score equal to or less than 3.0, 2.9, 2.859, 2.8, 2.7, 2.6, 2.5, 2.4, 2.3, 2.2, 2.1 or 2.0, preferably equal to or less than 3.0. In some embodiments, the fatty liver disease or disorder is selected from the group consisting of Non-Alcoholic Fatty Liver Disease (NAFLD) and Non-Alcoholic Steatohepatits (NASH).

In some embodiments, the present disclosure provides for the subject is characterized by at least one criteria selected from the group consisting: non or early stage hepatocyte apoptosis; sFas levels equal to or less than 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL, preferably equal to or less than 9.5 ng/mL; M30 levels equal to or less than 1500, 1400, 1300, 1200, 1100, 1000, 900, 800, 700, 600, or 500 U/L, preferably equal to or less than 900 U/L, more preferably equal to or less than 500 U/L; a NASH risk score equal to or less than 3.0, 2.9, 2.859, 2.8, 2.7, 2.6, 2.5, 2.4, 2.3, 2.2, 2.1 or 2.0, preferably equal to or less than 3.0; a baseline steatosis grade of about 2 to 3; and a baseline lobular inflammation grade of about 2 to 3.

In some embodiments, the present disclosure provides for a subject that is non diabetic, pre-diabetic or mildly diabetic. In some aspects of the disclosure, the subject receives no treatment for diabetes or no anti-diabetic agent. In some aspects of the disclosure, the subject receives at least one treatment for diabetes or at least one anti-diabetic agent. In some aspects of the disclosure, the subject receives at least one treatment for diabetes or at least one anti-diabetic agent is administered simultaneously with the pharmaceutical composition.

In some embodiments, the present disclosure provides for an anti-diabetic agent that is selected from the following group: PPARγ agonists, biguanides, protein tyrosine phosphatase-1B (PTP-1B) inhibitors, meglitinides, α glucoside hydrolase inhibitors, insulin secreatagogues, A2 antagonists, insulin and related compounds, PPAR dual agonists, Sodium glucose co-transporters (SGLT) 2 inhibitors, GSK 3β/GSK 3 inhibitors, dipeptidyl peptidase IV (DP-IV) inhibitors, peptides, sulfonylureas, and nonsulfonylurea secretagogues.

In some embodiments, the present disclosure provides for a subject who consumes a diabetic diet or a western diet.

In some embodiments, the disclosure provides for a method for treating a fatty liver disease or disorder in a subject in need thereof, comprising: selecting a subject having a: NAS score greater than or equal to 3; or steatosis score equal to or greater than 1; or lobular inflammation score equal to or greater than 1; or ballooning score equal to or greater than 1; or fibrosis score equal to or greater than 1; determining the subject's gamma glutamyl transferase (GGT) serum level; and administering a therapeutically effective amount of a pharmaceutical composition comprising at least one compound selected from the group consisting of ethyl eicosapentanoate (EPA-E), eicosapentaenoic acid (EPA) and its pharmaceutically acceptable amides, salts, esters and phospholipids to the subject, if the subject i) shows a serum gamma glutamyl transferase (GGT) level equal to or less than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women.

In some embodiments, the fatty liver disease or disorder is selected from the group consisting of Non-Alcoholic Fatty Liver Disease (NAFLD) and Non-Alcoholic Steatohepatits (NASH).

In some embodiments, selecting a subject having or suspected of having a fatty liver disease or disorder comprises selecting a subject having a score selected from the group consisting of: a NAS score greater than or equal to 3, a steatosis score equal to or greater than 1, a lobular inflammation score equal to or greater than 1, a ballooning score equal to or greater than 1 and a fibrosis score equal to or greater than 1.

In some embodiments, the disclosure provides for selecting a subject having or suspected of having a fatty liver disease or disorder, further comprising selecting a subject who is overweight.

In some embodiments, the disclosure provides for selecting a subject having or suspected of having a fatty liver disease or disorder, further comprising selecting a subject with a body mass index (BMI) greater than or equal to 25, 25.5, 26, 26.5, 27, 27.5, 28, 28.5, 29, 29.5, 29.9, 30, 30.5, 31, 32, 33, 34, 35, 36, 37, 38, 39 or 40 kg/m$^2$.

In some embodiments, the disclosure provides for selecting a subject having or suspected of having a fatty liver disease or disorder, further comprising selecting a subject with a familial history of fatty liver disease.

In some embodiments, the disclosure provides for selecting a subject having or suspected of having a fatty liver disease or disorder, further comprising selecting a subject with a NAS score greater than or equal to 4.

In some embodiments, the disclosure provides for selecting a subject having or suspected of having a fatty liver disease or disorder comprises selecting a subject with a normal serum direct bilirubin level equal to or less than 0.4, 0.3, 0.2, 0.17 or 0.1.

In some embodiments, a subject is characterized by at least one criteria selected from the group consisting of a baseline ALT value of about 10 to about 300 IU/L; a baseline AST value of about 10 to about 250 IU/L; a baseline steatosis grade of about 2 to 3; and a baseline lobular inflammation grade of about 2 to 3.

In some embodiments, the present disclosure provides for fatty liver disease characterized by the baseline pretreatment level in the subject of at least one criteria selected from the group consisting of ALT in a range of 10 to 300 IU/L, AST in a range of 10 to 250 IU/L, HDL/C in a range of 25 to 55 mg/dl, LDL-C in a range of 100 to 200 mg/dl, triglycerides in a range of 100 to 1000 mg/dl, TC in a range of 170 to 300 mg/dl, High TG and low HDL-C, TG/HDL-C ratio in a range of 3.75 to 10, non-HDL-C in a range of 100 to 250 mg/dl, Free fatty acid in a range of 400 to 1000 µEq/L, HOMA-IR in a range of 1.5 to 5, HbA1c in a range of 5.7 to 10%, Fasting plasma glucose in a range of 100 to 200 mg/dl, impaired glucose tolerance and metabolic syndrome.

In some embodiments, the present disclosure provides for fatty liver disease characterized by the baseline pretreatment level in the subject of at least one criteria selected from the group consisting of low level of EPA, docosapentaenoic acid (DPA), docosahexaenoic acid (DHA), EPA/arachidonic acid (AA), DHA/AA, DHA/DPA, AA/Homo-γ-linoleic acid: and high level of AA, monounsaturated fatty acid (MUFA), Palmitoleic acid, Oleic acid, Oleic acid/Stearic acid, Palmitoleic acid/Palmitic acid, γ-linoleic acid/Linoleic acid, Adrenic acid/AA compared to each average level in subjects with fatty liver disease.

In some embodiments, the present disclosure provides for administration of EPA-E and/or EPA and/or its pharmaceutically acceptable amides, salts, esters or phospholipids for about one year, and the subject exhibits at least one improvement selected from the group consisting of a reduced ALT value as compared to said baseline ALT value; a reduced AST value as compared to said baseline AST value; a reduced steatosis grade as compared to said baseline steatosis grade; and a reduced lobular inflammation grade as compared to said baseline lobular inflammation grade.

In some embodiments, the present disclosure provides for a therapeutically effective amount of EPA-E and/or EPA and/or its pharmaceutically acceptable amides, salts, esters or phospholipids administered to the subject is an amount between about 1800 and about 2700 mg per day.

In some embodiments, the present disclosure provides for a therapeutically effective amount of EPA-E and/or EPA and/or its pharmaceutically acceptable amides, salts, esters or phospholipids administered to the subject is at least 1800 mg per day.

In some embodiments, the present disclosure provides for a therapeutically effective amount of EPA-E and/or EPA and/or its pharmaceutically acceptable amides, salts, esters or phospholipids administered to the subject is at least 2700 mg per day.

In some embodiments, the present disclosure provides for the subject further characterized by having at least one condition selected from the group consisting of high triglycerides and low HDL-C, impaired glucose tolerance and metabolic syndrome.

In some embodiments, the present disclosure provides for reduced ALT value at least 1%, 2%, 3%, 4%, or 5% lower than said baseline ALT value and/or said reduced AST value is at least 1%, 2%, 3%, 4%, or 5% lower than said baseline AST value.

In some embodiments, the present disclosure provides for determining in a subject prior to treatment a baseline level in serum of at least one member selected from the group consisting of ALT in a range of 10 to 300 IU/L, AST in a range of 10 to 250 IU/L, HDL-C in a range of 25 to 55 mg/dl, LDL-C in a range of 100 to 200 mg/dl, triglycerides in a range of 100 to 1000 mg/dl, TC in a range of 170 to 300 mg/dl, High TG and low HDL-C, TG/HDL-C ratio in a range of 3.75 to 10, non-HDL-C in a range of 100 to 250 mg/dl, Free fatty acid in a range of 400 to 1000 µEq/L, HOMA-IR in a range of 1.5 to 5, HbA1c in a range of 5.7 to 10%, Fasting plasma glucose in a range of 100 to 200 mg/dl.

In some embodiments, the present disclosure provides for administration of ethyl eicosapentanoate for at least 3 months, said subject exhibits the following changes in said at least one marker as compared to the baseline level of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Adrenic acid/AA ratio, Ferritin, Thioredoxin, TNF α, sTNF-R1, sTNF-R2, Hs-CRP, CRGF, sCD40, Leptin, complement factor D, CK18 fragment, serum HMGB1, Fas, Hyaluronic acid, Type IV collagen (7s domain), procollagen III peptide or PAI-1; at least 5% increase for EPA or EPA/AA ratio; at least 1% increase for DPA, AA/Homo-γ-linoleic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count, sFas, M30, NASH risk score or BMI.

In some embodiments, the present disclosure provides for improving the steatosis and lobular inflammation condition of said subject, and no worsening of said fibrosis stage score.

In some embodiments, the present disclosure provides for improving the NAS score in said subject (i) to a composite score of ≤3 and no worsening of said fibrosis stage score, or (ii) by ≥2 across at least two of the NAS components and no worsening of said fibrosis stage score.

In some embodiments, the present disclosure provides for an improvement in serum EPA/AA ratio as compared to a baseline EPA/AA ratio.

In some embodiments, the present disclosure provides for improvement in serum EPA/AA ratio as compared to a baseline EPA/AA ratio equal to or greater than 0.1, 0.15, 0.2, 0.25, 0.3, 0.35 or 0.4.

In some embodiments, the present disclosure provides for the pharmaceutical composition administered to the subject 1 to 4 times per day.

In some embodiments, the present disclosure provides for the composition present in one or more capsules.

In some embodiments, the present disclosure provides for the composition comprising a self-emulsifying composition comprising 50 to 95% by weight of omega-3 polyunsaturated fatty acids or a pharmaceutically acceptable salt or ester thereof.

In some embodiments, the present disclosure provides for the composition comprising a self-emulsifying composition comprising 50 to 95% by weight, of EPA-E or a pharmaceutically acceptable salt or ester thereof.

In some embodiments, the present disclosure provides for the composition comprising a self-emulsifying composition comprising at least 60%, by weight, of EPA-E or a pharmaceutically acceptable salt or ester thereof.

In some embodiments, the present disclosure provides for the composition comprising a self-emulsifying composition comprising at least 70%, by weight, of EPA-E or a pharmaceutically acceptable salt or ester thereof.

In some embodiments, the present disclosure provides for the composition comprising a self-emulsifying composition comprising at least 80%, by weight, of EPA-E or a pharmaceutically acceptable salt or ester thereof.

In some embodiments, the present disclosure provides for the composition comprising a self-emulsifying composition comprising at least 90%, by weight, of EPA-E or a pharmaceutically acceptable salt or ester thereof.

In some embodiments, the present disclosure provides for the composition comprising a self-emulsifying composition comprising at least 95%, by weight, of EPA-E or a pharmaceutically acceptable salt or ester thereof.

In some embodiments, the present disclosure provides for the composition comprising a self-emulsifying composition comprising at least 96%, by weight, of EPA-E or a pharmaceutically acceptable salt or ester thereof.

In some embodiments, the present disclosure provides for the composition comprising, 5 to 50% by weight, an emulsifier having a hydrophilic lipophilic balance of at least 10.

In some embodiments, the present disclosure provides for the composition comprising, 10 to 50% by weight, an emulsifier having a hydrophilic lipophilic balance of at least 10.

In some embodiments, the present disclosure provides for the composition comprising, 20 to 50% by weight, an emulsifier having a hydrophilic lipophilic balance of at least 10.

In some embodiments, the present disclosure provides for the composition comprising, 30 to 50% by weight, an emulsifier having a hydrophilic lipophilic balance of at least 10.

In some embodiments, the present disclosure provides for the composition comprising, 40 to 50% by weight, an emulsifier having a hydrophilic lipophilic balance of at least 10.

In some embodiments, the present disclosure provides for the composition comprising, ethanol content up to 4% by weight in relation to the total content of the compound and the emulsifier.

In some embodiments, the present disclosure provides for the composition not containing ethanol.

In some embodiments, the present disclosure provides for the emulsifier at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, sorbitan fatty acid ester, glycerin fatty acid ester and lecithin.

In some embodiments, the present disclosure provides for the emulsifier as at least one member selected from the group consisting of polyoxyethylene hydrogenated castor oil, polyoxyethylene sorbitan fatty acid ester, polyoxyethylene castor oil, sucrose fatty acid ester, sorbitan fatty acid ester and glycerin fatty acid ester.

In some embodiments, the present disclosure provides for the polyoxyethylene hydrogenated castor oil as at least one member selected from the group consisting of polyoxyethylene (20) hydrogenated castor oil, polyoxyethylene (40) hydrogenated castor oil, polyoxyethylene (50) hydrogenated castor oil, polyoxyethylene (60) hydrogenated castor oil, and polyoxyethylene (100) hydrogenated castor oil.

In some embodiments, the present disclosure provides for the polyoxyethylene sorbitan fatty acid ester as at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate.

In some embodiments, the present disclosure provides for the polyoxyethylene castor oil as at least one member selected from the group consisting of compound prepared by adding polymerization of ethylene oxide to castor oil with an average ethylene oxide mole number of 3, 10, 20, 30, 40, 50 or more.

In some embodiments, the present disclosure provides for the sucrose fatty acid ester as at least one member selected from the group consisting of sucrose laurate, sucrose myristate, sucrose palmitate, sucrose stearate, and sucrose oleate.

In some embodiments, the present disclosure provides for the polyoxyethylene polyoxypropylene glycol as at least one member selected from the group consisting of polyoxyethylene (3) polyoxypropylene (17) glycol, polyoxyethylene (20) polyoxypropylene (20) glycol, polyoxyethylene (42) polyoxypropylene (67) glycol, polyoxyethylene (54) polyoxypropylene (39) glycol, polyoxyethylene (105) polyoxypropylene (5) glycol, polyoxyethylene (120) polyoxypropylene (40) glycol, polyoxyethylene (160) polyoxypropylene (30) glycol, polyoxyethylene (196) polyoxypropylene (67) glycol, and polyoxyethylene (200) polyoxypropylene (70) glycol.

In some embodiments, the present disclosure provides for the sorbitan fatty acid ester as at least one member selected from the group consisting of sorbitan monolaurate, sorbitan monostearate, sorbitan monooleate, sorbitan monopalmitate, sorbitan trioleate, and sorbitan sesquioleate.

In some embodiments, the present disclosure provides for the glycerin fatty acid ester as at least one member selected from the group consisting of glyceryl monooleate, glyceryl monostearate, decaglyceryl monooleate, decaglyceryl monolaurate decaglyceryl trioleate and tetraglyceryl monooleate.

In some embodiments, the present disclosure provides for the composition as containing a lecithin where lecithin is at least one member selected from the group consisting of soybean lecithin, enzymatically decomposed soybean lecithin, hydrogenated soybean lecithin, and egg yolk lecithin.

In some embodiments, the present disclosure provides the composition as containing a polyhydric alcohol, where it may further comprise propylene glycol or glycerin.

In some embodiments, the present disclosure provides the composition contains at least one member selected from the group consisting of eicosapentaenoic acid, docosahexaenoic acid, and their pharmaceutically acceptable amides, salts, esters and phospholipids.

In some embodiments, the present disclosure provides the composition contains less than 5% eicosapentaenoic acid, and their pharmaceutically acceptable amides, salts, esters and phospholipids.

In some embodiments, the present disclosure provides the composition contains less than 5% docosahexaenoic acid, and their pharmaceutically acceptable amides, salts, esters and phospholipids.

In some embodiments, the present disclosure provides the composition contains ethyl icosapentate and/or ethyl docosahexaenoate.

In some embodiments, the present disclosure provides the composition a total content of the emulsifier having an HLB of at least 10 is 10 to 100 parts by weight in relation to 100 parts by weight of the at least one compound selected from the group consisting of omega-3 polyunsaturated fatty acids and their pharmaceutically acceptable amides, salts, esters and phospholipids.

In some embodiments, the present disclosure provides the composition a total content of the emulsifier having an HLB of at least 10 is 10 to 50 parts by weight in relation to 100 parts by weight of the at least one compound selected from the group consisting of EPA-E and/or EPA and/or its pharmaceutically acceptable amides, salts, esters and phospholipids.

In some embodiments, the present disclosure provides the subject's serum HbA1c level is equal to 6.4%, less than 6.4%, between 5.7% and 6.4%, equal to 5.6% or less than 5.6%

In some embodiments, the present disclosure provides the subject's fasting serum glucose level is equal to 125 mg/dL, less than 125 mg/dL, between 100 mg/dL and 125 mg/dL, equal to 100 mg/dL or less than 100 mg/dL.

In some embodiments, the present disclosure provides the subject's serum HbA1c level is measured using a technique selected from the following group: high-performance liquid chromatography (HPLC); immunoassay; enzymatic assay; colorimetric assay; capillary electrophoresis and boronate affinity chromatography.

In some embodiments, the subject shows a serum gamma glutamyl transferase (GGT) level equal to or less than 24 IU/L.

In some embodiments the subject does not have a condition selected from the following group consisting of alcoholic liver injury, drug-induced liver injury, chronic active hepatitis, cirrhosis, liver cancer, hepatic steatosis and biliary tract disease.

In some embodiments, the present disclosure provides the subject's glucose level is measured using methods selected from the following: FPG, RPG and OGTT.

In some embodiments the subject shows unobstructed or normal excretion of bile, does not suffer from injury in the liver, does not exhibit liver dysfunction, shows normal levels of direct bilirubin, does not possess biliary tract disease or the subject possess biliary tract disease in an early stage.

In some embodiments the subject does not have a condition selected from the following group consisting of alcoholic liver injury, drug-induced liver injury, chronic active hepatitis, cirrhosis, liver cancer, hepatic steatosis and hepatocyte apoptosis.

In some embodiments the subject does not suffer from injury in the liver, does not exhibit liver dysfunction, shows levels of sFas, M30 corresponding to non or early stage hepatocyte apoptosis or a NASH risk score less than 3, or does not possess hepatocyte apoptosis or early stages of hepatocyte apoptosis.

In some embodiments the subject consumes a diabetic diet or a western diet.

In some embodiments EPA-E or EPA is at least 40% by weight in total of the fatty acids and their derivatives in the composition.

In some embodiments, the pharmaceutical composition of the present disclosure may be any EPA-E or EPA containing compositions, including commercially available sources such as Epadel® (Mochida Pharmaceutical Co., Ltd., Tokyo Japan), Lovaza™ (Glaxo SmithKline, FL USA), Omacor™ (Pronova Biopharma ASA, Oslo Norway), Lotriga™ (Takeda Pharmaceutical Co., Ltd., Osaka Japan) or Vascepa™ (Amarin Pharma Inc., NJ USA).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of a device of this disclosure are set forth with particularity in the appended claims. A better understanding of the features and advantages of this disclosure will be obtained by reference to the following detailed description that sets forth illustrative embodiments, in which the principles of a device of this disclosure are utilized, and the accompanying drawings.

FIG. 1 is a table representing the proportion of responders to EPA-E treatment (NAS Score ≤3 or improvement of ≥2 across at least 2 of NAS components) in a group of non diabetic (including pre-diabetic) and mild diabetic patients.

FIG. 2 is a table representing further characterization of the patients in FIG. 1. The table reflects the proportion of responders to EPA-E treatment (NAS Score ≤3 or improvement of ≥2 across at least 2 of NAS components) in a sub-group of non diabetic (including pre-diabetic) patients with HbA1c levels=<6.4.

FIG. 3 is a table representing further characterization of the patients in FIG. 1. The table reflects the proportion of responders to EPA-E treatment (NAS Score ≤3 or improvement of ≥2 across at least 2 of NAS components) in a sub-group of non diabetic (including pre-diabetic) and diabetic patients with fasting glucose levels=<125 mg/dL.

FIG. 4 is a table representing further characterization of the patients in FIG. 1. The chart reflects the proportion of responders to EPA-E treatment (NAS Score ≤3 or improvement of ≥2 across at least 2 of NAS components) in a sub-group of non diabetic (including pre-diabetic) and diabetic patients with fasting glucose levels=<125 mg/dL and HbA1c levels=<6.4.

FIG. 5 is a table of possible criteria for the evaluation of NASH for baseline scores before treatment, or after treatment.

FIG. 7 is a table representing the proportion of responders to EPA-E treatment (NAS Score ≤3 or improvement of across at least ≥2 of NAS components) in a group of patients found to have γ-Glutamyl Transferase (GGT) levels ≤33 IU/L.

FIG. 8 is a table of γ-Glutamyl Transferase (GGT) levels in the patients shown in FIG. 7 at the completion of the study.

FIG. 9 is a table representing further characterization of the patients shown in FIG. 7. The table reflects the improvement in NAS score of patients with γ-Glutamyl Transferase (GGT) levels ≤33 IU/L.

FIG. 10 is a table representing further characterization of the patients shown in FIG. 7. The table reflects the improvement of serum EPA/AA ratio on Day 365 of patients with γ-Glutamyl Transferase (GGT) levels ≤33 IU/L.

FIG. 11 is a table corresponding reference values for parameters of liver function in patients with γ-Glutamyl Transferase (GGT) levels ≤33 IU/L and patients with γ-Glutamyl Transferase (GGT) levels ≥33 IU/L.

FIG. 14 is a table representing the proportion of responders to EPA-E treatment (NAS Score ≤3 or improvement of ≥2 across at least 2 of NAS components) in a group of patients found to have serum levels of sFas equal to or less 9.5 ng/mL associated with NASH (1800 mg EPA-E, TID).

FIG. 15 is a table of sFas levels in the patients shown in FIG. 1 at the completion of the study.

FIG. 16 is a table representing further characterization of the patients shown in FIG. 1. The table reflects the improvement in NAS score of patients with sFas equal to or less 9.5 ng/mL associated with NASH (1800 mg EPA-E, TID).

FIG. 17 is a table representing the proportion of responders to EPA-E treatment (NAS Score ≤3 or improvement of ≥2 across at least 2 of NAS components) in a group of patients found to have serum levels of M30 (cytokeratin-18 fragment) equal to or less 1500 U/L associated with NASH (1800 mg EPA-E, TID).

FIG. 18 representing patients with blood serum sFas equal to or less 10.0 ng/mL and serum levels of M30 equal to or less 1500 U/L levels associated with NASH (1800 mg EPA-E, TID and 2700 mg EPA-E, TID) vs. Proportion of responders.

FIG. 19 representing patients who were determined to have NASH risk score equal to or less than 3.0 associated with NASH (1800 mg EPA-E, TID) vs. proportion of responders.

FIG. 20 is a table corresponding reference values for parameters of hepatocyte apoptosis in patients with sFas ≤9.5 ng/mL and reference values as determined by Tamimi T I., et. al., J. Hepatol., 54, 1224-1229, 2011.

FIG. 22 is a table of corresponding EPA/AA ratios for patients including patients with a serum sFas level equal to or less than 9.5 ng/mL.

I. TERMINOLOGY

Figure 6:
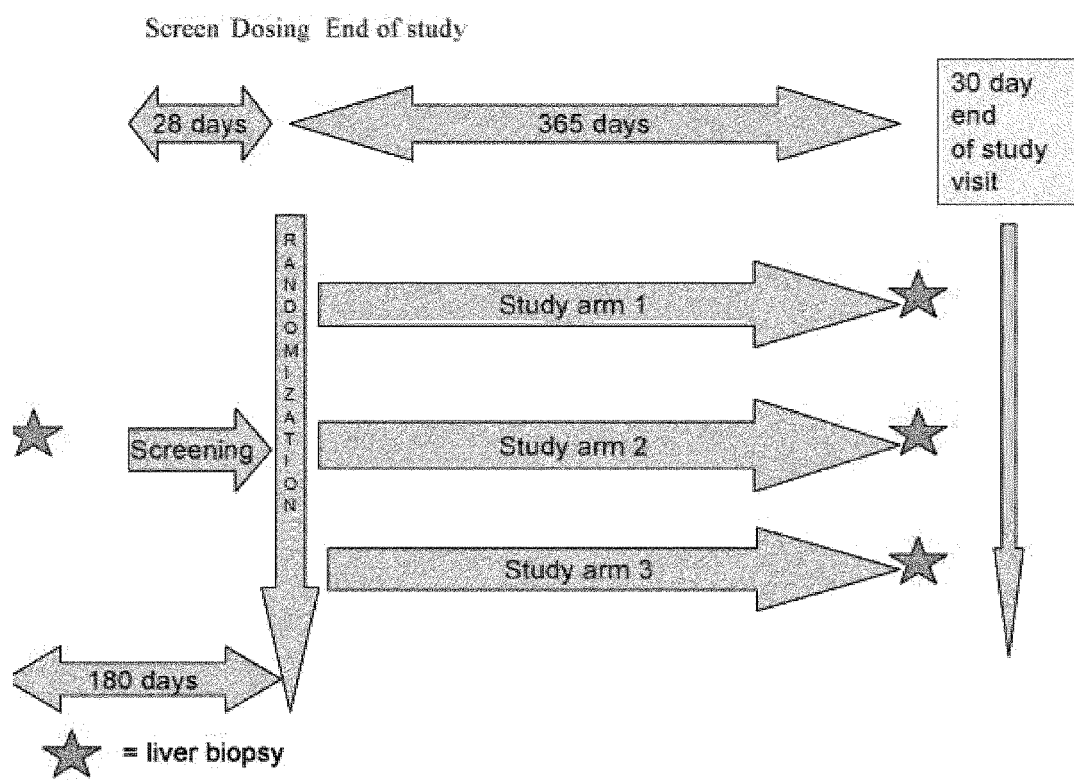
FIG. 6 is a schematic of the experimental screen dosing at the end of a clinical trial study as described herein.

The terminology of the present disclosure is for the purpose of describing particular embodiments only and is not intended to be limiting of compositions, methods and devices of this disclosure.

The terms "methods of treating" mean amelioration, prevention or relief from the symptoms and/or effects associated with NAFLD-associated disorders, including steatosis (simple fatty liver), NASH and advanced scarring of the liver (cirrhosis). As used herein, reference to "treatment" of a patient is intended to include prophylaxis.

As used herein, a "therapeutically effective amount" of a drug or pharmaceutical composition or formulation, or agent, described herein is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

A "subject" or "patient" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The term "pre-diabetic" is the condition wherein an individual is pre-disposed to the development of type 2 diabetes. Pre-diabetes extends the definition of impaired glucose tolerance to include individuals with a fasting blood glucose within the high normal range ≥100 mg/dL (J. B. Meigs, et al. Diabetes 2003; 52:1475-1484) and fasting hyperinsulinemia (elevated plasma insulin concentration), fasting serum glucose levels between 100 mg/dL and 125 mg/dL, or HbA1c levels between 5.7% and 6.4%. The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749). Pre-diabetic may be included in non-diabetic as provided by this disclosure.

The term "mildly-diabetic" is the condition wherein an individual in early progression of the development of type 2 diabetes. Diabetes extends the definition of impaired glucose tolerance to include individuals with a fasting blood glucose within the high normal range ≥126 mg/dL and/or HbA1c levels ≥6.5%. Mild-diabetes is diabetes who receives no treatment for diabetes, no ant-diabetic agents or only one anti-diabetic agent.

The term "non-diabetic" is the condition wherein an individual does not present impaired glucose tolerance and includes individuals with a fasting blood glucose within the normal range less than 100 mg/dL or HbA1c levels equal to or less than 5.6%.

The term "medical nutrition therapy" is a therapeutic approach to treating medical conditions and their associated symptoms via the use of a specifically tailored diet devised and monitored by a: registered dietitian. The diet is based upon the patient's medical and psychosocial history, physical examination, functional examination and dietary history, for example a diabetic diet, a low-salt diet, a low-fat diet, a low carbohydrate diet, a western diet, a oriental diet, a Japanese diet or Mediterranean diet.

The term "physical exercise" is any bodily activity that enhances or maintains physical fitness and overall health and wellness. It is performed for various reasons including strengthening muscles and the cardiovascular system, honing athletic skills, weight loss or maintenance, as well as for the purpose of enjoyment.

The term "HbA1c" refers to the product of a non-enzymatic glycation of the haemoglobin B chain. The HbA1c value is determined by HbA1c (NGSP: National Glycohemoglobin Standardization Program, USA) or A1C (USA). The HbA1c includes also HbA1c (JDS: Japan Diabetes Society, Japan), HbA1c (IFCC: International Federation of Clinical Chemistry, International) and Mono-S (Sweden). Conversion factors for HbA1c(NGSP) or A1C compared to each of the HbA1c are shown below; HbA1c (JDS)=(980× (HbA1c(NGSP))−0.245, HbA1c(IFCC)=(10.93×HbA1c (NGSP))−23.50 and Mono-S=(1.081×HbA1c(NGSP))− 1.440.

Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks.

The term "biliary tract function" is any anatomical, physiological or biochemical function provided by the biliary tract in the body. The biliary tract is the common anatomical term for a duct that transports bile, secreted by the liver, to the small intestine (duodenum). As provided by this disclosure, biliary traction function may also include secretion of bile. Additionally, biliary tract function may also include the excretion of bilirubin, a byproduct of red blood cells recycled by the liver.

The term "normal" or "substantially normal" as applied to biliary tract function refers to unobstructed or otherwise functioning transport of bile. Abnormal biliary tract function or biliary disease, used interchangeably herein, may include but is not limited to abnormal or elevated levels of markers associated with biliary disease, obstruction of the bial duct, decreased secretion of bile or bilirubin, failure to secrete bile or bilirubin, abnormal pressure in the biliary duct, gallstones or cirrhosis of the liver as a result thereof.

The term "GGT" refers to γ-glutamyl transferase enzyme or gamma-glutamyl transpeptidase (also γ-glutamyltransferase, GGT, GGTP, gamma-GT). This enzyme catalyzes the transfer of gamma-glutamyl functional groups of glutathione which is a strong anti-oxidant. It is found in many tissues, the most notable one being the liver, and has significance in medicine as a diagnostic marker. Other lines of evidence indicate that GGT can also exert a prooxidant role, A digested product of glutathione "Cys-Gly", in conjunction with metal ions, will produce active oxygen. Therefore, oxidation stress may increase when GGT level remains high.

The term "GGT test" refers to a common liver function test to test the activity levels of GGT. Blood test results for GGT suggest that the normal value is 8-78 IU/L (Merck Manual Appendix II, 2001, Merck Sharp & Dohme Corp., NJ USA), for men is 2-30 IU/L (Duh S H., Laboratory Reference Range Values, 2005, StedmansOnline, Lippincott Williams & Wilkins, PA USA) or 15-85 IU/L (*General Laboratory Manual*. Department of Pathology, Hackensack University Medical Centre. 2010. p. 117), whereas for women it is 1-24 IU/L (Laboratory Reference Range Values) or 5-55 IU/L (*General Laboratory Manual*. Department of Pathology, Hackensack University Medical Centre. 2010. p. 117).

The term "liver injury" or "liver disease" or "liver dysfunction" may be used interchangeably and refer to any injury of the liver, including but not limited to hardening of the liver, scarring of the liver, decreased or abnormal biliary tract function, abnormal liver enzyme activity, cirrhosis of the liver, abnormal physiology as determined by common diagnostic methods include but not limited to ultrasound, or biopsy/histopathology, necrosis of the liver and the like.

The term "EPAs" refer to eicosapentaenoic acid (EPA) and/or any pharmaceutically acceptable amides, salts, esters and phospholipids of EPA or any other form which lead to metabolization of EPA, or the incorporation of EPA into body fluids, tissues or organs, including but not limited to inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as mono-, di- and TG, and exemplary phospholipids such as phosphatidylcholine, phosphatidylethanolamine, phosphatidylserine, phosphatidylglycerol and phosphatidylinositol. Preferable examples include ethyl ester and TG ester, and the more preferred is ethyl ester. More specifically, preferable examples include EPA-E, TG ester of EPA, and the like. The term "DHAs" refer to docosahexaenoic acid (DHA) and/or any pharmaceutically acceptable amides, salts, esters and phospholipids of DHA or any other form which lead to metabolization of DHA, or the incorporation of DHA into body fluids, tissues or organs, including but not limited to inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as mono-, di- and TG, and exemplary phospholipids such as phosphatidylcholine, phosphatidylethanolamine, phosphatidylserine, phosphatidylglycerol and phosphatidylinositol. Preferable examples include ethyl ester and TG ester, and the more preferred is ethyl ester.

More specifically, preferable examples include ethyl docosahexaenoic acid (DHA-E), TG ester of DHA, and the like.

The term "hepatocyte apoptosis" refers to any mode of cell death of liver cells. The term may be used to comprise cell death described as apoptosis, necrosis, necroptosis, autophagy or cornification. Hepatocyte apoptosis may result from any form of liver injury or disease, including but not limited to cancer and fatty liver disease or disorders which may further comprise non-alcoholic steatohepatitis (NASH), non-alcoholic associated fatty liver disease, secondary NAFLD, steatosis, progressive fibrosis, liver failure and cirrhosis. As used herein, secondary NAFLD may refer to NAFLD or similar symptoms that result from the use of one or more of the following medications: amiodarone, antiviral drugs such as nucleoside analogues, aspirin or NSAIDs, corticosteroids, methotrexate, nifedipine, perhexiline, tamozifen, tetracycline, and valproic acid. Hepatocyte apoptosis is a prominent pathologic feature of human NASH and the magnitude of apoptosis present correlates with the degree of liver damage and stage of fibrosis.

The term "non" or "early stage" as applied to hepatocyte apoptosis refers to the absence or beginning stages of cell death in the liver. Non and early stage hepatocyte apoptosis may be determined by any suitable means, including suitable immunoassays, biochemical assays, detection and measurement of abnormal or elevated levels of markers associated with hepatocyte apoptosis, such as sFas or M30, histological studies, microscopic studies or a NASH risk score calculated to be 3.0 or less. In some cases, non or early stages of hepatocyte apoptosis refers to a serum levels of sFas in a patient equal to or less than 10.0 ng/mL. In some cases non or early stages of hepatocyte apoptosis refers to a serum levels of M30 in a patient equal to or less than 1500 U/L. In some cases non or early stages of hepatocyte apoptosis refers to a NASH risk score equal to or less than 3.0.

The term "sFas" refers to soluble Fas. Fas is a protein belonging to a death receptor of the tumor necrosis factor (TNF) family and involved in caspase activated pathways associated with cell death. Fas may also be known as Apo-1 or CD95. sFas is generated either by alternative mRNA splicing or proteolysis of membrane Fas. sFas may refer to any Fas or variant thereof capable of binding the Fas ligand. sFas refers to any related sFas that may be used as a biochemical marker, as measured in blood serum, to indicate the presence or absence of hepatocyte apoptosis in a subject.

The term "cytokeratin M30" or "M30" refers to cytokeratin-18 fragment M30 (M30). Cytokeratin-18 is a type I cytokeratin, or intermediate filament protein. M30 refers to a soluble fragment of the cytokeratin-18 protein that may be cleaved. M30 may be generated by any caspase enzymes during apoptosis or cell death, such as in hepatocytes. In some cases, M30 may be generated through cleavage of cytokeratin-18 by caspase-3. "M30", "M30 fragment" or CK-18 fragment may be used interchangeably as provided herein. M30 may also be known as ccK18, K19-Asp396, cytokeratin 18, ccCK18 or CK18-Asp396. M30 may further refer to any related soluble fragment of cytokeratin-18 that may be used as a biochemical marker, as measured in blood serum, to indicate the presence or absence of hepatocyte apoptosis in a subject.

In some cases, as determined by the method of Tamimi T I., et. al., J. Hepatol., 54, 1224-1229, 2011, incorporated by reference herein, NASH patients may be characterized by plasma sFas median ($25^{th}$, $75^{th}$ percentile) levels 11.8 (7.8, 12.5) ng/mL and M30 median ($25^{th}$, $75^{th}$ percentile) levels 598 (280, 846) U/L. Non-NASH patients may be characterized by plasma sFas median ($25^{th}$, $75^{th}$ percentile) levels 5.9 (4.8, 8.3) ng/mL and M30 median ($25^{th}$, $75^{th}$ percentile) levels 176 (131, 224) U/L.

The term "NASH risk score" or "risk score, refers to a composite score as calculated by the following equation: Risk Score=−6.4894+0.0078×M30 (U/L)+0.4668×sFas (ng/mL) as cited by Tamimi T I., et. al., J. Hepatol., 54, 1224-1229, 2011. Serum or plasma levels sFas and M30 are measured in a subject and used to compute a risk score based on the regression equation as provided herein.

The term "liver injury" or "liver disease" or "liver dysfunction" may be used interchangeably and refer to any injury of the liver, including but not limited to hardening of the liver, scarring of the liver, decreased or abnormal biliary tract function, abnormal liver enzyme activity, hepatocyte apoptosis, cirrhosis of the liver, abnormal physiology as determined by common diagnostic methods include but not limited to ultrasound, or biopsy/histopathology, necrosis of the liver and the like.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". As used herein, the term "Unit (U)" is intended to include not only "U" but also "International Unit (IU)".

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

The term "combination use" used in the present invention designates the embodiment in which the drug is administered when the effect and/or action of another drug is present in the body of the patient. In some embodiments, both drugs are simultaneously present in the patient's body, for example, in the patients' blood. In some embodiments, the other drug is administered within 24 hours after the administration of the first drug. Combinations according to the invention are generally envisioned and not specifically limited as long as the active ingredients are used in combination. Exemplary such embodiments of the drug administration include, for example, (1) administration of single preparation having both active ingredients incorporated therein; (2) administration of both active ingredients by preparing separate preparations each containing different active ingredients, and simultaneously administering these separate preparations from the same administration route with or without producing a kit of the combination of two preparations; (3) administration of both active ingredients by preparing separate preparations each containing different active ingredients, and administering these separate preparations at different timing with time lag from the same administration route with or without producing a kit of the combination of two preparations; (4) administration of both active ingredients by preparing separate preparations each containing different active ingredients, and simultaneously administering these separate preparations from different administration routes (of the same patient from different site) with or without producing a kit of the combination of two preparations; and (5) administration of both active ingredients by preparing separate preparations each containing different active ingredients, and administering these separate preparations at different timing with time lag from different administration routes (of the same patient from different site) with or without producing a kit of the combination of two preparations.

When the active ingredients are administered at different timing with time lag, the first and the second ingredients may be administered in this order, or in opposite order. When the active ingredients are administered simultaneously, these ingredients may be mixed immediately before the administration if the administration route is the same, while the active ingredients may be separately administered. The active ingredients may be used deliberately at different timing for various purposes. In an exemplary embodiment, one ingredient may be administered, and thereafter, the other ingredient may be administered while the effect of the first ingredient is about to occur or the effect of the first ingredient is still fully present.

In another embodiment, one drug, and in particular, the second ingredient may be administered once or twice a day by using an extended release formulation, and the other ingredient, and in particular, the first ingredient may be administered two or more times, for example, twice or three times a day, or alternatively, once or twice a day by using an extended release formulation. When both drugs are administered once or twice a day, and more preferably, when both drugs are administered once or twice a day simultaneously, or administered by incorporating in a composite formulation, the burden of the patients can be reduced to improve the drug compliance, and in turn, to improve the prophylactic/ameliorative or therapeutic effects and reduce the side effect. It is also possible that both drugs are administered and one drug is withdrawn while the effects of the ingredients are about to occur or the effects of the ingredients are still fully present.

II. TREATMENT INDICATIONS

The methods and compositions of the present disclosure are useful for the treatment of subjects having fatty liver related disorders and are known, or suspected to be, non-diabetic, pre-diabetic, or mildly diabetic, by administration of an effective amount of EPAs. The methods and compositions of the present disclosure are also useful for the treatment of subjects having fatty liver related disorders and are known to have or suspected of having normal or substantially normal biliary tract function, by administration of an effective amount of EPAs.

A. Fatty Liver Disease or Disorders

This disclosure provides compositions and methods for treating fatty liver disease or disorders which may include but are not limited to non-alcoholic steatohepatitis (NASH), non-alcoholic associated fatty liver disease, secondary NAFLD, steatosis, progressive fibrosis, liver failure and cirrhosis. As used herein, secondary NAFLD may refer to NAFLD or similar symptoms that result from the use of one or more of the following medications: amiodarone, antiviral drugs such as nucleoside analogues, aspirin or NSAIDs, corticosteroids, methotrexate, nifedipine, perhexiline, tamoxifen, tetracycline, and valproic acid. The term fatty liver disease or disorder, NASH, as described herein, may be referred to and used interchangeably as NASH herein.

B. Diabetes

This disclosure also provides compositions and methods for treating NASH subjects who may also be or suspected to be non-diabetic, pre-diabetic, or mildly diabetic. Diabetes mellitus, commonly called diabetes, refers to a disease process derived from multiple causative factors and characterized by elevated levels of plasma glucose, referred to as hyperglycemia. There are two major forms of diabetes: Type 1 diabetes (also referred to as insulin-dependent diabetes or IDDM) and Type 2 diabetes (also referred to as noninsulin dependent diabetes or NIDDM). Type 1 diabetes is the result of an absolute deficiency of insulin, the hormone that regulates glucose utilization. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies. Type 2 diabetes is a disease characterized by insulin resistance accompanied by relative, rather than absolute, insulin deficiency. Premature development of atherosclerosis and increased rate of cardiovascular and peripheral vascular diseases are characteristic features of patients with diabetes.

Subjects referred herein as "diabetic" may have diabetes or associated conditions. Diabetes, may include but is not limited to Type 1 diabetes, Type 2 diabetes, gestational diabetes mellitus (GDM), maturity onset of diabetes of the young (MODY), pancreatitis, polycystic ovarian disease, impaired glucose tolerance, insulin resistance, hyperglycemia, hyperinsulinemia, elevated blood levels of fatty acids or glycerol, obesity, Syndrome X, dysmetabolic syndrome and related diseases, diabetic complications (including retinopathy, neuropathy, nephropathy) and sexual dysfunction. The conditions, diseases, and maladies collectively referenced to as "Syndrome X" or Dysmetabolic Syndrome (as detailed in Johanson, J. Clin. Endocrinol. Metab., 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications or NAFLD.

C. Biliary Tract Function

This disclosure also provides compositions and methods for treating NASH subjects who are known to have or suspected of having normal or substantially normal biliary tract function. As herein described, biliary tract function generally relates to any function of the biliary of tract in the body, including anatomical, physiological and biochemical function. The primary function of the biliary tract is the transport of bile, secreted by the liver, to the small intestine. As provided by this disclosure, biliary tract function may also include the secretion of bile.

Bile or gall, is a dark green, or yellowish fluid that aids in the process of the digestion of lipids in the small intestine. Bile is stored in the gallbladder and upon eating, is discharged into the duodenum. Bile may comprise water, bile salts, mucus and pigments, fats and inorganic salts.

Bile may act a surfactant, aiding in emulsifying the fats in food. Bile salts may be amphopathic, wherein salts contain both hydrophilic and hydrophobic elements. Bile may form micelles around hydrophobic molecules, such as fats and fatty acids, wherein the hydrophobic sides orient toward the hydrophobic molecule with the hydrophilic sides facing outward. Bile is also used for the excretion of bilirubin, a byproduct of red blood cells recycled by the liver. It is well known that bile enhances forming micelles and an absorption of fatty acids at small intestine.

D. Hepatocyte Apoptosis

This disclosure also provides compositions and methods for treating NASH subjects who are known to have or suspected of having non or early stage hepatocyte apoptosis. As herein described, hepatocyte apoptosis generally relates to any modes of cell death of liver cells. Cell death may include mechanisms or biochemical pathways characterized by apoptosis, necrosis, necroptosis, autophagy or cornification. Hepatocyte apoptosis may result from any form of liver injury or disease, including but not limited to cancer and fatty liver disease or disorders which may further include non-alcoholic steatohepatitis (NASH), non-alcoholic associated fatty liver disease, secondary NAFLD, steatosis, progressive fibrosis, liver failure and cirrhosis.

i. Caspase-Dependent Apoptosis

In some cases, hepatocyte apoptosis may be induced by caspase-dependent or caspase-independent pathways. Biochemically, apoptosis may be commonly initiated and executed by activation of intracellular caspases (cysteine-dependent aspartate specific protease). Like other intracellular proteases, caspases are synthesized as zymogens that must undergo proteolytic cleavage to exert proteolytic activity. Caspases have a dominant specificity for protein substrates containing four- or five-amino acid sequences containing an aspartate residue in the P1 position (the amino acid on the $NH_2$-terminal side of the scissile bond), a unique feature of this class of proteases. Caspases themselves must be cleaved at aspartate residues for activation, and thus caspases are activated by other caspases. These proteases may be classified as initiator caspases, which contain a long prodomain for scaffolding with other proteins, and executioner (effector) caspases, containing a short prodomain. Initiator caspases include caspases 2, 8, 9, and 10. The initiator caspases 8 and 10 are involved in death receptor-mediated apoptosis, whereas caspase 9 initiates apoptosis following mitochondrial dysfunction. "Executioner caspases" such as caspases 3, 7, and 6 are activated by cleavage by initiator caspases at aspartate residues and can be activated by either death receptor or mitochondrial pathways of apoptosis. These caspases may activate caspase-activated DNase (CAD) by cleaving ICAD, an inhibitor of this enzyme. CAD activation results in DNA cleavage at internucleosomal linker regions of DNA resulting in the ladder pattern of DNA cleavage (multiples of the 180-bp nucleosomal regions) that may be characteristic of apoptosis.

ii. sFas in Hepatocyte Apoptosis

Death receptors such as Fas are a subgroup of the TNF/nerve growth factor (NGF) receptor superfamily that may play a role in inducing apoptosis in hepatocytes. These cytokine receptors are type I transmembrane proteins (single membrane-spanning proteins with an extracellular $NH_2$ terminus) with three distinct regions: an extracellular, $NH_2$-terminal ligand-interacting domain characterized by serial cysteine-rich repeat domains, a membrane-spanning region, and an intracellular COOH-terminal domain characterized by a stretch of ~60-80 amino acids known as the "death domain" necessary for the initiation of cytotoxic signals when engaged by cognate ligands. Some death receptors, namely, Fas (CD95/APO1), TNF-R1 (p55/CD120a), TRAIL-R1 (death receptor 4-DR4), and TRAIL-R2 (death receptor 5-DR5/APO-2/KILLER), are ubiquitously expressed in the liver. These receptors bind to specific ligands, the majority of which are type II transmembrane proteins (single membrane-spanning proteins with an extracellular COOH terminus) belonging to the TNF family. Engagement of death receptors by their corresponding ligands such as Fas ligand (FasL) or soluble Fas ligand (sFasL) may trigger the so-called extrinsic pathways of apoptosis, a signaling cascade resulting in activation of effector caspases and cell death. The liver contains a high level of expression of death receptors and renders it more susceptible to excessive apoptosis by this pathway. Death receptors expressed in the liver have been implicated in various liver injuries in different pathological settings.

The Fas receptor is constitutively expressed by every cell type in the liver. Its ligand, FasL, may be expressed as a transmembrane protein on the cell surface of activated cytotoxic T lymphocytes (CTL) but is also found in the soluble non membrane bound form (sFasL). Both forms of FasL, including sFasL, may play a role in hepatocyte apoptosis. In certain pathological conditions, sFasL can also be expressed by hepatocytes and induce fratricide cell death of sFasL-expressing hepatocytes, amplifying the tissue damage. Kupffer cells also express FasL in response to engulfment of apoptotic bodies, a process that may, under pathological conditions, exacerbate hepatocyte apoptosis and liver injury and promote liver inflammation and fibrosis such as in fatty liver related diseases such as NASH or NAFLD. sFas may be expressed as an alternative splice variant in response to a pathological condition such as NASH.

The FasL may bind to preoligomerized Fas receptor on the plasma membrane to initiate the signaling cascade. FasL binding induces a conformational change in the receptor intracellular domain which results in recruitment of the adaptor protein FADD (Fas-associated protein with death domain) and pro-caspase 8 and/or 10, after relocalization of the receptor to lipid rafts. Multiple receptors may then be recruited to the lipid rafts to form larger aggregates that are subsequently internalized via clathrin-mediated endocytosis and delivered to the early endosomal compartment, a step required for efficient complex formation and amplification of the death signal. This complex, comprising Fas, FasL, FADD, and caspase 8, is referred to as death-inducing signaling complex (DISC) which triggers death of the cell.

Dysregulation of Fas and sFas apoptosis has been associated with several liver diseases. Toxic bile acids accumulating within the hepatocyte in cholestatic disease are known to induce hepatocyte apoptosis in a sFas-mediated manner. Elevated intracellular concentrations of bile acids can induce Fas translocation from the cytosol and Golgi complex to the plasma membrane, where the increased surface density facilitates its oligomerization and initiation of the apoptotic signal.

Fas expression and hepatocyte apoptosis are elevated in the liver of NASH patients, and sensitivity to sFasL is increased in steatotic livers compared with normal livers, suggesting that Fas-mediated cell death may be an important feature of NASH and fatty liver diseases. sFas has been shown to be a suitable biomarker for the assessment of NASH disease.

iii. Cytokeratin-M30 and sFas in Hepatocyte Apoptosis

Cytokeratin-18 fragment M30 (M30) is a type I cytokeratin, or intermediate filament protein that may be cleaved during hepatocyte apoptosis. M30 refers to a soluble fragment or product of this enzymatic cleavage. M30 may be generated by an enzyme, including caspase cleavage, such as with caspase-3, during activation of the caspase cascade pathway was described herein. As referenced in U.S. Pat. No. 7,883,904, M30 may be a suitable biomarker for hepatocyte apoptosis.

E. Evaluation Criteria for Subjects with NASH

Generally, any suitable method or combination of methods may be used in evaluating NASH in a subject. In terms of physical symptoms, NASH is generally asymptomatic until severe liver impairment occurs. Patients may generally feel well in the early stages and only begin to have symptoms, such as fatigue, weight loss, and weakness once the disease is more advanced or cirrhosis develops. The progression of NASH may take years, or even decades. The process can stop and, in some cases, reverse on its own without specific therapy. In some cases, NASH may slowly worsen, causing scarring or "fibrosis" to appear and accumulate in the liver. As fibrosis worsens, cirrhosis develops; the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. These physical symptoms in the late stages of the disorder may be used to determine the presence or absence of NASH in a subject.

i. Biopsy

Due to the asymptomatic nature of the disorder, particularly in early stages of the disease, one or more technique and methods may be used to assess the absence or presence of NASH in a subject. In some cases, a biopsy is performed on the liver, whereby a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or NAFLD is diagnosed. In some cases, a biopsy may also indicate the presence or absence of scar tissue that has developed in the liver. Currently, no blood tests or scans can reliably provide this information.

ii. Blood Tests and Biomarkers

While there are no single laboratory tests for NASH, various abnormal levels of liver enzymes, biomarkers and other biological blood components may be used in aiding diagnosis of the disorder. For example, in some cases, elevated serum aminotransferase may indicate NASH. In some cases measuring the level of a plurality of suitable biomarkers in a sample derived from the subject may be used. In some cases such as adipocytokine, apoptosis markers, and/or cell death markers, may be analyzed and compared to reference levels to aid in diagnosis of NASH.

In some cases subjects treated for NASH according to the present disclosure can also be evaluated for baseline scores of the following criteria before treatment, and evaluated after treatment for possible changes in those criteria. The evaluated criteria can comprise one or more of the following criteria set forth in FIG. 5.

iii. NAS Score

In some cases, patients or subjects treated for NASH according to the present disclosure can also be evaluated using a combination of standardized histologic scores, as known in the art. Due to significant inter-observer variance in the clinical diagnosis of NASH, and the severity of the disorder at given time, a composite score of histologic features using a standardized NASH scoring system has been implemented and can be used to provide a measurement of NASH in a subject. This combined measurement is known as the non-alcoholic fatty liver disease activity score (NAS).

In some cases the NAS score may be determined for a subject prior to initiation of treatment in order to provide a baseline level or score for the criteria as well as evaluation after the dosing regimen to evaluate any improvement in the criteria. In other cases, a NAS score may be determined for a subject undergoing treatment. In some cases, a NAS score and comparison of NAS scores over time may be used in assess disease progression of NASH.

The non-alcoholic fatty liver disease activity score (NAS) is defined as the unweighted sum of the values for steatosis (ranging from 0-3), lobular inflammation (ranging from 0-3) and ballooning (ranging from 0-2), thereby providing a range of NAS score of from 0 to 8. (See Kleinen et al., Design and Validation of a Histological Scoring System for Nonalcoholic Fatty Liver Disease, Hepatology, Vol. 41, No. 6, 2005, pp. 1313-1321) Patients treated for NASH according to the present disclosure can show a NAS score prior to treatment of ≥4, with a minimum score of 1 each for steatosis and lobular inflammation plus either ballooning or at least 1 a sinusoidal fibrosis and a finding of possible or definite steatohepatitis. After dosing/treatment, such as for one year, patients can show a composite NAS score of ≤3, ≤2 or ≤1, together with no worsening in fibrosis. Alternatively, patients can show an improvement in NAS by a value of ≥2 across at least two of the NAS components, together with no worsening in fibrosis. Alternatively, patients can show an improvement in NAS score by ≥3, 4, 5, 6, 7 or 8.

iv. Steatosis

Steatosis is broadly understood to describe a process involving the abnormal accumulation of lipids within the liver, which inhibits normal liver function. Liver biopsy enables analysis and scoring of steatosis in a patient, with scores ranging from 0-3. Patients treated for NASH according to the present disclosure can have a steatosis score of 1, 2 or 3, such as between about 2 and about 3. After treatment, it is desired for patients to exhibit no worsening of steatosis, alternatively a reduction of at least 1 in the steatosis score, or a reduction of 2 or 3 in the steatosis score. Steatosis is traditionally graded with a score of 1 indicating the presence of fat droplets in less than 33% of hepatocytes, a score of 2 indicating fat droplets observed in 33-66% of hepatocytes, and a score of 3 indicating observation of fat droplets in greater than 66% of hepatocytes. (See Kleinen et al., Design and Validation of a Histological Scoring System for Nonalcoholic Fatty Liver Disease, Hepatology, Vol. 41, No. 6, 2005, pp. 1313-1321)

v. Lobular Inflammation

Lobular inflammation is also evaluated upon liver biopsy and scored with values of 0-3. (See Kleinen et al., Design and Validation of a Histological Scoring System for Nonalcoholic Fatty Liver Disease, Hepatology, Vol. 41, No. 6, 2005, pp. 1313-1321 Table 1) Patients to be treated for NASH can have lobular inflammation scores of 1, 2 or 3, alternatively ranging between 1 and 2 or 2 and 3. After treatment, patients can have a reduction in lobular inflammation score of at least 1, alternatively a reduction of 2 or 3 in lobular inflammation score, and at least no worsening of the lobular inflammation score.

vi. Ballooning

Ballooning of hepatocytes is generally scored with values of 0-2, (See Kleinen et al., Design and Validation of a Histological Scoring System for Nonalcoholic Fatty Liver Disease, Hepatology, Vol. 41, No. 6, 2005, pp. 1313-1321 Table 1), and patients treated for NASH according to the present disclosure can have ballooning scores of 0-2, including specific values of 1 or 2, and alternatively a score ranging from 1 to 2. After treatment, patients can show at least no worsening of the ballooning score, alternatively a reduction of at least one value lower in the ballooning score, and alternatively a reduction of two in the value of the ballooning score.

vii. Fibrosis Stage

Fibrosis is also evaluated upon liver biopsy and scored with values of 0-4, the scores being defined as: 0 represents no fibrosis, 1 represents perisinusoidal or periportal fibrosis, 1a represents mild, zone 3, perisinusoidal fibrosis; 1b represents moderate zone 3, perisinusoidal fibrosis; 1c represents portal/periortal fibrosis; 2 represents perisinusoidal and portal/periportal fibrosis; 3 represents bridging fibrosis; and 4 represents cirrhosis. (See Kleinen et al., Design and Validation of a Histological Scoring System for Nonalcoholic Fatty Liver Disease, Hepatology, Vol. 41, No. 6, 2005, pp. 1313-1321) Patients treated according to the present disclosure can have a fibrosis stage score of 0-3, including 0, 1, 1a, 1 b, 1 c, 2 or 3, and can have a fibrosis stage score of at least 1a. After treatment, patients can have a fibrosis stage score that is at least no worse than the baseline score, and alternatively can have a reduction in the fibrosis stage score of at least one level, alternatively at least two or three levels.

F. Evaluation Criteria for Diabetes in NASH Subjects

As described herein, the methods and compositions of the present disclosure are useful for the treatment of subjects having fatty liver related disorders and are known, or suspected to be, non-diabetic, pre-diabetic, or mildly diabetic, by administration of an effective amount of EPAs. The presence of absence of non diabetes, pre-diabetes, or mild diabetes may be determined in a subject using any suitable methods known in the art. Generally, preferred tests for diabetes in NASH patients may be characterized in two groups: serum glucose-based tests and glycated proteins. Serum glucose-based tests may include but are not limited to tests such as fasting plasma glucose (FPG), random plasma glucose (RPG), and the oral glucose tolerance test (OGTT). Tests of glycated proteins may include but are not limited to tests that measure proteins such as HbA1c. In some cases, one or more tests may be used to determine the presence or absence of non diabetes, pre-diabetes, or mild diabetes. In some cases a combination of tests may be used to assess diabetes in NASH subjects.

i. Fasting Plasma Glucose (FPG)

The FPG test is a simple plasma glucose measurement obtained after at least 8 hours of fasting (usually an overnight fast). This test may be used for screening and diagnosis of diabetes in NASH subjects due to ease, expense and risk factors. FPG is the ADA test of choice for diagnosis of both pre-diabetes and diabetes. When compared directly, FPG has better intra-individual reproducibility than 2-hour post-load plasma glucose, with intra-individual coefficients of variation of 6.4-11.4% for FPG versus 14.3-16.7% for 2-hour plasma glucose.

FPG may be a reliable predictor of diabetes complications at the current threshold for diagnosis, and studies examining FPG have underlined much of the current knowledge about the pathology of diabetes. However, as known in the art the threshold for pre-diabetes and its relationship to complications may vary across individuals or populations of individuals. General ranges for FPG for assessing non diabetes, pre-diabetes, or mild diabetes are described herein.

ii. Causal Plasma Glucose (RPG)

RPG (or "casual" plasma glucose) measurements may be easily obtained from NASH subjects, do not require fasting, and are frequently included in a basic metabolic panel ordered for other purposes. RPG tests may be determine diabetes, wherein a commonly accepted RPG threshold is ≥200 mg/dl, along with symptoms of polyuria, polydipsia, and unexplained weight loss to indicate a second test for confirmation of diagnosis. An RPG of 140-199 mg/dl is suggestive of pre-diabetes. Based on diagnosis by OGTT, an RPG ≥200 mg/dl is insensitive but has a specificity approaching 100%.

Impairing the overall utility of the RPG as a testing tool is the absence of data comparing it directly to rates of diabetes-specific complications. For this reason, use of the RPG test may be used for rapid, any-time testing with high specificity in symptomatic NASH subjects.

iii. Oral Glucose Tolerance Test (OGTT)

Alternative tests for glucose also may include oral glucose tolerance testing. In some cases it is the preferred test for diabetes diagnosis. Regarding the diagnosis of diabetes, OGTT identifies about 2% more individuals than does FPG, OGTT has poor reproducibility compared to other glucose-based tests such as HbA1c (NGSP) or A1C.

HbA1c testing is known in the art as a standardized measure for diabetes diagnosis that is now broadly used for both research and clinical purposes and may used to determine the presence of absence of non diabetes, pre-diabetes, or mild diabetes in NASH subjects. Its major practical advantages are that it can be obtained in both fasting and nonfasting states, and it represents average glucose control over a period of months rather than a single point value. The ADA recommends this test a first-line test for screening and diagnosis. At approximately the same time, the International Expert Committee released the formal recommendation of an HbA1c level ≥6.5% for diabetes diagnosis.

HbA1c level may be measured using any suitable biochemical techniques. These may include but are not limited to high-performance liquid chromatography (HPLC); immunoassay; enzymatic assay; colorimetric assay; capillary electrophoresis and boronate affinity chromatography.

As with the glucose-based tests, there is no finite threshold of HbA1c at which normality ends and diabetes begins. The International Expert Committee has elected to recommend a cut point for diabetes diagnosis that emphasizes specificity, commenting that this "balanced the stigma and cost of mistakenly identifying individuals as diabetic against the minimal clinical consequences of delaying the diagnosis in someone with an HbA1c level <6.5%.

iv. General Thresholds for Evaluating Diabetes

The tests recommended for screening are the same as those for making the diagnosis, with the result that a positive screen is equivalent to a diagnosis of mild diabetes, pre-diabetes or diabetes. The term "pre-diabetes" has been assigned to those considered to be at higher risk for developing diabetes. In some cases, pre-diabetes is diagnosed by having one or both of the following: 1) an FPG of 100-125 mg/dl, which is also referred to as impaired fasting glucose (IFG) or 2) a 2-hour, 75-g OGTT, with 2-hour plasma glucose levels of 140-199 mg/dl, which is also described as IGT. To get a diagnosis of diabetes, patients must satisfy one of the following criteria: 1) symptoms of diabetes (polyuria, polydipsia, and unexplained weight loss) AND an RPG ≥200 mg/dl, 2) an FPG ≥126 mg/dl, or 3) a 2-hour plasma glucose level ≥200 mg/dl during a 75-g OGTT. Additional diagnostic criteria of an HbA1c result ≥6.5% may also indicate pre-diabetes or mild diabetes. Subjects having mild diabetes may have levels at or about threshold levels as described herein.

As already described herein, the term "pre-diabetic" in the present disclosure extends the definition of impaired glucose tolerance to include individuals with a fasting blood glucose within the high normal range ≥100 mg/dL (J. B. Meigs, et al.

Diabetes 2003; 52:1475-1484) and fasting hyperinsulinemia (elevated plasma insulin concentration), or HbA1c levels between 5.7% and 6.4%.

The term "mildly-diabetic" extends the definition of impaired glucose tolerance to include individuals with a fasting blood glucose within the high normal range ≥126 mg/dL and/or HbA1c levels ≥6.5% and who receives no treatment for diabetes, no ant-diabetic agents or only one anti-diabetic agent.

The term "non-diabetic" is the condition wherein an individual does not present impaired glucose tolerance and includes individuals with a fasting blood glucose within the normal range less than 100 mg/dL or HbA1c levels less equal to or less than 5.6%.

In some instances, wherein a NASH subject may be pre-diabetic or mildly diabetic, the NASH subject may undergo treatment or receive an anti diabetic agent. In some cases a NASH subject may have a western diet, which may comprise foods heavy in carbohydrates and fats. In other cases, a NASH subject may adopt a diabetic diet, which may comprise a lower carbohydrate diet. In some cases, a NASH subject may receive one or anti-diabetic agents alone or in combination with the pharmaceutical compositions of this disclosure. In some cases, the anti-diabetic may be administered simultaneously as the pharmaceutical composition. In some cases, the pharmaceutical compositions are administered after a NASH subject receives one or more anti-diabetic agents.

v. Anti-Diabetic Agents

In some cases as NASH a subject may be receive one or more anti diabetic agents which may include: PPARγ agonists such as glitazones (e.g., WAY-120,744, AD 5075, balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), rivoglitazone (CS-011, Sankyo), GL-262570 (Glaxo Welcome), BRL49653 (disclosed in WO98/05331), CLX-0921, 5-BTZD, GW-0207, LG-100641, JJT-501 (JPNT/P&U), L-895645 (Merck), R 119702 (Sankyo/Pfizer), NN-2344 (Dr. Reddy/NN), YM-440 (Yamanouchi), LY-300512, LY-519818, R483 (Roche), T131 (Tularik) and the like. In some embodiments, the glitazone used is pioglitazone, rosiglitazone or troglitazone.

In some cases an anti diabetic agent may comprise biguanides such as metformin hydrochloride (N,N-dimethylimidodicarbonimidic diamide hydrochloride, such as Glucophage™, Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A. G.); other metformin salt forms (including where the salt is chosen from the group of, acetate, benzoate, citrate, ftimarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octanoate, decanoate, hexadecanoate, octodecanoate, benzenesulphonate, trimethoxybenzoate, paratoluenesulphonate, adamantanecarboxylate, glycoxylate, glutamate, pyrrolidonecarboxylate, naphthalenesulphonate, 1-glucosephosphate, nitrate, sulphite, dithionate and phosphate), and phenformin; bile acid sequestrants that include, but are not limited to, cholestyramine (i.e., QUESTRAN®, QUESTRAN LIGHT®, CHOLYBAR®, CA registry no. 11041-12-6), colesevelam (i.e., WELCHOL®, CA registry nos. 182815-43-6 and 182815-44-7), colestipol (i.e., COLESTID®, CA registry nos. 50925-79-6 and 37296-80-3), sevelamer, dialkylaminoalkyl derivatives of a cross-linked dextran, LOCHOLEST®, DEAE-Sephadex (SECHOLEX®, POLIDEXIDEL®), water soluble derivatives such as 3,3-ioene, N-(cycloalkyl)alkylamines and poliglusam, insoluble quaternized polystyrenes, saponins and mixtures thereof, those bile acid sequestrants disclosed in WO97/11345, WO98/57652, U.S. Pat. No. 3,692,895, and U.S. Pat. No. 5,703,188, including pharmaceutically acceptable salts or mixtures thereof. Suitable inorganic cholesterol sequestrants include bismuth salicylate plus montmorillonite clay, aluminum hydroxide and calcium carbonate antacids. In some embodiments, the biguanide used is metformin hydrochloride, metformin hydrochloride with glyburide, buformin or etoformine. In some embodiments, the bile acid sequestrant used is cholestyramine, colestipol, or dialkylaminoalkyl derivatives of a cross-linked dextran and DEAE-Sephadex.

In some cases an anti diabetic agent may comprise protein tyrosine phosphatase-1B (PTP-1B) inhibitors, such as A-401,674, KR 61639, OC-060062, OC-83839, OC-297962, MC52445, MC52453, ISIS 113715, and those disclosed in WO99/585521, WO99/58518, WO99/58522, WO99/61435, WO03/032916, WO03/032982, WO03/041729, WO03/055883, WO02/26707, WO02/26743, JP2002114768, and pharmaceutically acceptable salts and esters thereof; sulfonylureas such as acetohexamide (e.g., Dymelor, Eli Lilly), carbutamide, chlorpropamide (e.g., Diabinese®, Pfizer), gliamilide (Pfizer), gliclazide (e.g., Diamcron, Servier Canada Inc), glimepiride (e.g., disclosed in U.S. Pat. No. 4,379,785, such as Amaryl™, Aventis), glipentide, glipizide (e.g., Glucotrol or Glucotrol XL Extended Release, Pfizer), gliquidone, glisolamide, glyburide/glibenclamide (e.g., Micronase or Glynase Prestab, Pharmacia & Upjohn and Diabeta, Aventis), tolazamide (e.g., Tolinase), and tolbutamide (e.g., Orinase), and pharmaceutically acceptable salts and esters thereof.

In some cases an anti diabetic agent may comprise meglitinides such as repaglinide (e.g., Pranidin®, Novo Nordisk), KAD1229 (PF/Kissei), mitiglinide (e.g. Glufast®, Kissei) and nateglinide (e.g., Starlix®, Novartis), and pharmaceutically acceptable salts and esters thereof;

In some cases an anti diabetic agent may comprise a glucoside hydrolase inhibitors (or glucoside inhibitors) such as acarbose (e.g., Precose™, Bayer disclosed in U.S. Pat. No. 4,904,769), miglitol (such as Glyset™, Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-alpha-D-glucopyranoside, Marion Merrell Dow), voglibose (Takeda), adiposine, emiglitate, pradimicin-Q, salbostatin, CKD-711, MDL-25,637, MDL-73,945, and MOR 14, and the like. For example, the α glucoside hydrolase inhibitor is acarbose, voglibose or miglitol.

In some cases an anti diabetic agent may comprise insulin secreatagogues such as linogliride, A-4166, forskilin, dibutyrl cAMP, isobutylmethylxanthine (IBMX), and pharmaceutically acceptable salts and esters thereof, fatty acid oxidation inhibitors, such as clomoxir, and etomoxir, and pharmaceutically acceptable salts and esters thereof.

In some cases an anti diabetic agent may comprise A2 antagonists, such as midaglizole, isaglidole, deriglidole, idazoxan, earoxan, and fluparoxan, and pharmaceutically acceptable salts and esters thereof.

In some cases an anti diabetic agent may comprise insulin and related compounds (e.g., insulin mimetics) such as biota, LP-100, novarapid, insulin detemir, insulin lispro, insulin glargine, insulin zinc suspension (lente and ultralente), Lys-Pro insulin, GLP-1 (1-36) amide, GLP-1 (73-7) (insulintropin, disclosed in U.S. Pat. No. 5,614,492), LY-315902 (Lilly), GLP-1 (7-36)-NH2), AL-401 (AutoImmune), certain compositions as disclosed in U.S. Pat. No. 4,579,730, U.S. Pat. No. 4,849,405, U.S. Pat. No. 4,963,526, U.S. Pat. No. 5,642,868, U.S. Pat. No. 5,763,396, U.S. Pat. No. 5,824,638, U.S. Pat. No. 5,843,866, U.S. Pat. No. 6,153,632, U.S. Pat. No. 6,191,105, and WO 85/05029, and primate, rodent, or rabbit insulin including biologically active variants thereof including allelic variants, human insulin available in recombinant form (sources of human insulin include pharmaceutically acceptable and sterile formulations such as those available from Eli Lilly (Indianapolis, Ind. 46285) as Humulin™ (human insulin rDNA origin), also see the Physician's Desk Reference, 55.sup.th Ed. (2001) Medical Economics, Thomson Healthcare (disclosing other suitable human insulins).

In some cases an anti diabetic agent may comprise PPAR dual agonists and pharmaceutically acceptable salts and esters thereof;
PPARα/γ dual agonists such as AR-H039242 (Astrazeneca), GW-409544 (Glaxo-Wellcome), BVT-142 (Biovitrum), CLX-0940, GW-1536 (Glaxo-Wellcome), GW-1929 (Glaxo-Wellcome), GW-2433 (Glaxo-Wellcome), KRP-297 (Kyorin Merck; 5-[(2,4-Dioxo thiazolidinyl)methyl]methoxy-N-[[4-(trifluoromethyl)phenyl]methyl]benzamide), L-796449, LR-90, LY-578 (lilly), LY-4655608 (lilly), LSN-862, LY-510929 (lilly), LY-929 (lilly), DRF4158 (Dr Reddys), MK-0767 (Merck/Kyorin/Banyu), SB 219994 (SmithKline Beecham), muraglitazar (BMS), tesaglitzar (Astrazeneca), reglitazar (JT-501, JTT-501), farglitazar (GW-2570/GI-262579), aleglitazar (Roche), saroglitazar (Zydus) and the like;
PPARα/δ dual agonists such as GFT505 (Genfit), TIPP401 (Okayama University) and the like.

In some cases an anti diabetic agent may comprise SGLT2 inhibitors such as canagliflozin (Mitsubishi Tanabe, TA-7284), dapagliflozin (Astrazeneca), Luseogliflozin (Taisho, TS-071), tofogliflozin (Kowa, CSG452), empagliflozin (Boehringer-Ingelheim, Lilly, BI-10773), ipragliflozin (Astellas, ASP1941), BI44847 (Boehringer-Ingelheim, Ajinomoto), LX-4211 (Lexicon), DSP-3235/GSK1614235 (Glaxo SmithKline, Dainippon Sumitomo, Kissei) ISIS388626 (Isis), sergliflozin (Glaxo SmithKline), remogliflozin (Glaxo SmithKline) and the like, In some cases an anti diabetic agent may comprise GSK 3β/GSK 3 inhibitors such as 4-[2-(2-bromophenyl)-4-(4-fluorophenyl-1H-imidazol-5-yl] pyridine and the like.

In some cases an anti diabetic agent may comprise dipeptidyl peptidase IV (DPP-IV) inhibitors such as sitagliptin, vildagliptin, alogliptin, linagliptin and saxagliptin, glucagon-like peptide 1 derivative reagents such as exenatide, lixisenatide and liraglutide, or peptides including amlintide and Symlin® (pramlintide acetate).

G. Evaluation Criteria of Biliary Function in NASH Subjects

As described herein, the methods and compositions of the present disclosure are useful for the treatment of subjects having fatty liver related disorders and are known, or suspected to have normal or substantially normal biliary tract function, by administration of an effective amount of EPAs. The presence of absence of normal or substantially normal biliary tract function may be determined in a subject using any suitable methods known in the art. Generally, preferred tests for biliary tract function in NASH patients may be characterized in two groups: physiological based tests and biochemical based tests. Physiological based tests may include but are not limited to abdominal ultrasound, abdominal CT scan, endoscopic retrograde cholangiopancreatography (ECRP), Percutaneous transhepatic cholangiogram (PTCA) or Magnetic resonance cholangiopancreatography (MRCP). Biochemical based tests may include but are not limited to GGT tests, liver function tests, bilirubin tests, alkaline phosphatase (ALP) tests, liver enzyme tests, amylase blood test, lipase blood test, prothrombin time, and measurement of urine bilirubin. In some cases, one or more tests may be used to characterize biliary function. In some cases a combination of tests may be used to assess biliary function in NASH subjects.

i. Physiological Tests

Generally, the physiological tests, examples of which are provided herein, provide a visualization of the biliary duct, which may aid in the diagnosis of an obstruction. For example, if gallstones are present, these may be result in obstruction or partial obstruction of the biliary duct and the presence of gallstones may be visualized. In some cases visualization is achieved with X-rays (PTCA or abdominal CT), magnetic resonance (MRCRP) or ultrasound. In some cases, a direct obstruction may not be visualized. In some cases, these methods may indicate the narrowing of the biliary duct, or secondary effect of an obstruction. These may also aid in evaluating biliary function in a NASH subject.

ii. GGT Test

The GGT test is a common liver function enzyme test that measures the activity of the enzyme GGT. Blood test results for GGT suggest that the normal value is 8-78 IU/L (Merck Manual Appendix II), for men is 2-30 IU/L (Laboratory Reference Range Values) or 15-85 IU/L (*General Laboratory Manual*. Department of Pathology, Hackensack University Medical Centre. 2010. p. 117), whereas for women it is 1-24 IU/L (Laboratory Reference Range Values) or 5-55 IU/L (*General Laboratory Manual*. Department of Pathology, Hackensack University Medical Centre. 2010. p. 117).

In some cases, elevated serum GGT activity may be indicative of diseases of the liver, biliary system, and pancreas. In this respect, it is similar to alkaline phosphatase (ALP) tests, as described herein in detecting disease of the biliary tract. Both ALP and GGT may be used to as biochemical indicator of potential liver disease, although GGT tests generally provide increased sensitivity. Slightly elevated serum GGT may also been found to correlate with cardiovascular diseases in NASH subjects. GGT may accumulate in atherosclerotic plaques, and may circulate in blood in the form of distinct protein aggregates, some of which may indicate specific pathologies such as metabolic syndrome, alcohol addiction and chronic liver disease. High body mass index (BMI) may be associated with type 2 diabetes subjects with high serum GGT. Tests for GGT levels may be used alone or in combination with other tests to assess biliary tract function in NASH subjects.

iii. ALP Test

The ALP test is a common liver function enzyme test that measures the activity of the enzyme ALP. The normal range is 36-92 IU/L (Merck Manual Appendix II) or 20 to 140 IU/L (*General Laboratory Manual*. Department of Pathology, Hackensack University Medical Centre. 2010. p. 117) High ALP levels can show that the bile ducts are obstructed. Levels are significantly higher in children and pregnant women.

iv. Additional Biochemical Based Tests

Generally, any suitable biochemical tests may be used in the assessment of biliary function of NASH subjects. In some cases, tests, as part of a standard liver function panel, may be used to assess biliary function. In some cases, bilirubin tests may be useful to assess biliary function. One or more tests may be used in combination tests as provided herein in the assessment of biliary function.

iv. General Thresholds for Evaluating Biliary Function

The tests recommended for screening are the same as those for making the diagnosis, with the result that a positive screen is equivalent to a diagnosis of normal or substantially normal biliary function. In this case, normal or substantially normal may also comprise a subject being at risk for biliary disease. In some cases, biliary disease is diagnosed by having one or both of the following: 1) GGT equal to or more than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women 2) an ALP test equal to or more than 92 or 140 IU/L. To get a diagnosis of abnormal biliary function, patients must satisfy one of the following criteria: 1) symptoms of biliary disease (i.e. narrowing or obstruction of the bial duct, weight loss, pain in the abdomen,) AND abnormal levels of GGT or ALP. Additional diagnostic criteria of one or more of these indicators may also indicate abnormal biliary function. In some cases, biliary disease is diagnosed by having serum direct bilirubin equal to or more than 0.3 or 0.4. Subjects having early stages of biliary disease may have levels at or about threshold levels as described herein.

D. Evaluation Criteria of Hepatocyte Apoptosis in NASH Subjects

As described herein, the methods and compositions of the present disclosure are useful for the treatment of subjects having fatty liver related disorders and are known, or suspected to have non or early stage hepatocyte apoptosis, by administration of an effective amount of ethyl eicosapentaenoic acid (EPA-E). The presence of absence non or early stage hepatocyte apoptosis may be determined in a subject using any suitable methods known in the art. Generally, preferred tests for non or early stage hepatocyte apoptosis in NASH patients may be characterized in two groups: physiological based tests and biochemical based tests. Physiological based tests may include but are not limited to abdominal ultrasound, abdominal CT scan, endoscopic retrograde cholangiopancreatography (ECRP), Percutaneous transhepatic cholangiogram (PTCA) or Magnetic resonance cholangiopancreatography (MRCP). Biochemical based tests may include but are not limited to serum level measurements of sFas and M30, liver function tests, liver enzyme tests or a composite NASH risk score as provided by Tamimi T I., et. al., J. Hepatol., 54, 1224-1229, 2011. In some cases, one or more tests may be used to characterize hepatocyte apoptosis. In some cases a combination of tests may be used to assess hepatocyte apoptosis in NASH subjects.

i. Physiological Tests

Generally, the physiological tests, examples of which are provided herein, provide a visualization of the liver, which may aid in the diagnosis of a hepatocyte apoptosis. For example, if apoptosis is present, histological samples may be taken to visualize tissue. In some cases visualization is achieved with differential staining such as with hetaoxylin and eosin-stains. Other stains, specific for dead or dying cells may also be used to visualize hepatocyte apoptosis. In some cases, fluorescence microscopy examination may be also used to visualize apoptotic cells. In some cases, visualization of other histological or cellular indicators such as an elevated presence of lysomes may also be used to assess hepatocyte apoptosis.

ii. Measurement of sFas

In some cases, sFas may be used as a biochemical marker for the assessment of hepatocyte apoptosis. In some cases, sFas is measured as protein in serum or plasma of a subject having or suspected of having NASH. Blood test results for sFas suggest a level equal to or less than 10.0 ng/mL, preferably a level equal to or less than 9.5 ng/mL for a subject having non or early stage hepatocyte apoptosis.

In some cases, elevated serum or plasma sFas levels may be indicative of diseases of the liver and hepatocyte apoptosis. Elevated sFas may also been found to correlate with cardiovascular diseases in NASH subjects. sFas may circulate and may indicate specific pathologies such as metabolic syndrome, alcohol addiction and chronic liver disease. High body mass index (BMI) may be associated with type 2 diabetes subjects with high sFas. Tests for sFas levels may be used alone or in combination with other tests to assess hepatocyte apoptosis in NASH subjects.

Generally, any suitable means for assessing sFas levels may be used. In some cases, sFas may be determined using any suitable biochemical assay including but not limited to immunoassay, ELISA, western blot, PCR, activity assays, binding assays, chromatography, spectrometry, mass spectrometry and the like.

For example, sFas may be measured by any non commercial or commercial kits available. Commercial kits may include but are not limited to Quantikine Human soluble Fas Kit (R&D systems, Minneapolis, Minn.), sFas ELISA Kit (Orient Yeast, Osaka, Japan), Human Soluble Fas Ligand ELISA Kit (Kamiya Biomedical, Seattle, Wash.) or FAS Ligand (Soluble) Human ELISA Kit (Invitrogen, Camarillo, Calif.). The concentration of the sFas in the sample can be usually expressed in nanogram per milliliter (ng/mL) or picogram per milliliter (pg/mL).

The assayed level of sFas can be correlated with liver damage and/or liver disease progression by comparing the level of hepatocyte apoptosis with a predetermined value. In one aspect of the invention, the predetermined value can be based upon sFas in comparable samples obtained from the general population or from a select population of human subjects. For example, the select population may be comprised of apparently healthy subjects. In other words, such individuals, if examined by a medical professional, would be characterized as healthy and free of symptoms of liver disease.

iii. Measurement of M30

In some cases, M30 may be used as a biochemical marker for the assessment of hepatocyte apoptosis. In some cases, M30 is measured as protein in serum or plasma of a subject having or suspected of having NASH. Blood test results for M30 suggest a level equal to or less than 1500 U/L, preferably a level equal to or less than 900 U/L, more preferably a level equal to or less than 500 U/L for a subject having non or early stage hepatocyte apoptosis.

In some cases, elevated serum or plasma M30 levels may be indicative of diseases of the liver and hepatocyte apoptosis. Elevated M30 fragments may also been found to correlate with cardiovascular diseases in NASH subjects. M30 may circulate and may indicate specific pathologies such as metabolic syndrome, alcohol addiction and chronic liver disease. High body mass index (BMI) may be associated with type 2 diabetes subjects with high serum M30 levels. Tests for M30 levels may be used alone or in combination with other tests to assess hepatocyte apoptosis in NASH subjects.

Generally, any suitable means for assessing M30 levels may be used. In some cases, M30 may be determined using any suitable biochemical assay including but not limited to immunoassay, ELISA, western blot, PCR, activity assays, binding assays, chromatography, spectrometry, mass spectrometry and the like.

For example, M30 may be measured by any non commercial or commercial kits available. Commercial kits may include but are not limited to M30-Apoptosense ELISA (Peviva, Bromma, Sweden) or Human Cytokeratin 18-M30, CK 18-M30 ELISA kit (Cusabio, Newark, Del.).

In some cases, M30 can be detected and/or quantified using an immunoassay, such as an enzyme-linked immunoabsorbent assay (ELISA). In an ELISA, antibodies specific to a particular antigen are used to detect the presence of, or measure the amount of, a particular molecule. By way of example, an M30-APOPTOSENSE (PEVIVA, Grünwald, Germany) ELISA may be used to detect the presence of, or measure the amount of or level of, caspase 3-generated CK-18 fragments. The APOPTOSENSE assay uses the M30 antibody, which recognizes a neo-epitope in the C-terminal domain of CK-18, which is exposed after cleavage of CK-18 by caspases (e.g., caspase 3) after aspartic acid residue 396. The M30 antibody used in the APOPTOSENSE assay is a mouse monoclonal antibody of the IgG2b subtype.

An ELISA typically comprises the steps of contacting a sample taken from a subject with one or more antibodies, and then assaying for the formation of a complex between the antibody and a protein or peptide in the sample. For ease of detection, the antibody can be attached to a substrate such as a column, plastic dish, matrix, or membrane, such as nitrocellulose. The sample may be untreated, subject to precipitation, fractionation, separation, or purification before combining with the antibody. The APOPTOSENSE assay, for example, is a solid-phase, two-site immunosorbent assay. In some cases bodily samples, such as blood serum, may be simultaneously reacted with the mouse monoclonal antibody M5 (directed against CK-18 and immobilized to a polystyrene well) and a horseradish peroxidase-conjugated M30 monoclonal antibody. Following the formation of the solid phase/antigen/labeled antibody sandwich, excess unbound conjugate may be removed by a washing step. It should be noted that the APOPTOSENSE assay may also be used in combination with the M65 ELISA (PEVIVA, Grünwald, Germany) which measures total CK-18. Combining the two assays allows the calculation of the relative fraction of CK-18 that is caspase-cleaved.

In an ELISA, interactions between the antibody or antibodies in the sample and the protein(s) or peptide fragment(s) are detected by radiometric, colorimetric, or fluorometric means, size-separation, or precipitation. In one example, detection of the antibody-protein or peptide complex is by addition of a secondary antibody coupled to a detectable tag, such as an enzyme, fluorophore, or chromophore. In the present invention, tetramethyl-benzidine substrate may be added to the assay and color develops in proportion to the bound analyte. The color development may then be stopped and color intensity measured in a microplate reader at 450 nm. By plotting a standard curve from known concentrations versus measured absorbance, the amount of caspase 3-generated CK-18 fragments in the bodily sample can be calculated. The concentration of the M30 fragment in the sample can be expressed in Units per Liter (U/L).

Additional assays can be used to detect and/or quantify M30 fragment in the bodily sample. These additional assays can include other immunoassays, such as immunoassays employing antibodies disclosed in U.S. Pat. Nos. 6,296,850, 6,716,968, 6,706,488 and 7,883,904 all of which are incorporated herein by reference in their entirety. Other immunoassays that use CK-18 detecting antibodies can be used to detect the CK-18 fragments. These assays can include radioimmunoassays, both solid and liquid phase, fluorescence-linked assays, and competitive immunoassays as well as other assays, such as mass spectrometry (MS)-based methods (e.g., liquid chromatography MS and electrospray ionization MS). MS based methods may be useful for detecting and/or quantifying the level of M30 fragments as, for example, the parent molecules, i.e., the non-cleaved M30 fragment molecules will have different masses than the M30 fragment. Additionally, methods such as HPLC may also be useful for detecting the presence of M30 fragment because distinct parent-daughter ion transitions can occur after cleavage of CK-18 by caspase 3. Thus, charge differences and changes in polarity between cleaved and non-cleaved CK-18 proteins have a high likelihood of showing distinct retention times on HPLC.

The assayed level of M30 can be correlated with liver damage and/or liver disease progression by comparing the level of hepatocyte apoptosis with a predetermined value. In one aspect of the invention, the predetermined value can be based upon the level of Ck-18 fragments (e.g., IU/L) in comparable samples obtained from the general population or from a select population of human subjects. For example, the select population may be comprised of apparently healthy subjects. In other words, such individuals, if examined by a medical professional, would be characterized as healthy and free of symptoms of liver disease.

iv. Additional Biochemical Based Tests

Generally, any suitable biochemical tests may be used in the assessment of hepatocyte apoptosis in NASH subjects. In some cases, tests, as part of a standard liver function panel, may be used to assess hepatocyte apoptosis. In some cases, the state of lysosomes may be assessed by determining the proportion of lysosomal enzymes (β-galactosidase, β-glucuronidase, cathepsin C and cathepsin B) present in a sample, such as liver tissue. Apoptosis may also be monitored by measuring caspase 3 activity (DEVDase) or the measurement of sulfite cytochrome c reductase, an enzyme located in the mitochondrial intermembrane space that may be released upon apoptotic pathways in liver cells. Generally, any protein, gene or biomarker known to be involved in cell death or apoptosis related pathways of liver cells may be used to assess hepatocyte apoptosis.

iv. General Thresholds for Evaluating Hepatocyte Apoptosis

The tests recommended for screening are the same as those for making the diagnosis, with the result that a positive screen is equivalent to a diagnosis of non or early stage hepatocyte apoptosis. In this case, non or early stage hepatocyte apoptosis may also comprise a subject being at risk for non or early stage hepatocyte apoptosis. In some cases, non or early stage hepatocyte apoptosis is diagnosed by having one or both of the following: 1) sFas levels equal to or less than at least 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL or sFas levels equal to or less than at most 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, or 8.0 ng/mL; 2) M30 levels equal to or less than at least 1500, 1400, 1300, 1200, 1100, 1000, 900, 800, 700, 600, or 500 U/L or M30 levels equal to or less than at most 1500, 1400, 1300, 1200, 1100, 1000, 900, 800, 700, 600, or 500

U/L; a NASH risk score equal to or less than at least 3.0, 2.9, 2.859, 2.8, 2.7, 2.6, 2.5, 2.4, 2.3, 2.2, 2.1 or 2.0 or a NASH risk score equal to or less than at most 3.0, 2.9, 2.859, 2.8, 2.7, 2.6, 2.5, 2.4, 2.3, 2.2, 2.1 or 2.0. In some cases, to get a diagnosis of non or early stage hepatocyte apoptosis, patients may also satisfy one of the following criteria: 1) symptoms of hepatocyte apoptosis (i.e. histological visualization, cirrhosis of the liver or other clinical symptoms related to liver damage) and levels of sFas or M30 corresponding to non or early stage hepatocyte apoptosis. Additional diagnostic criteria of one or more of these indicators may also indicate hepatocyte apoptosis. Subjects having early stages of hepatocyte apoptosis may have levels at or about threshold levels as described herein.

III. PHARMACEUTICAL COMPOSITION

A. Compositions Comprising EPAs

Eicosapentaenoic acid (EPA) is a known omega-3 polyunsaturated, long-chain fatty acid. Omega-3 fatty acids are known as components of oils, such as fish oil. A variety of commercial products are promoted as containing omega-3 fatty acids, or their salts, esters, phospholipids, derivatives, conjugates and the like. Eicosapentaenoic acid (EPA) is also known as its ethyl ester form, ethyl eicosapentanoate (EPA-E). According to the present disclosure, EPAs (including, but not limited to EPA or EPA-E) can be administered in a composition. Content of EPAs in the total fatty acid of the compositions of the present disclosure is not particularly limited as long as the composition contains EPAs as its effective component and intended effects of the present disclosure are attained, high purity EPAs are preferably used.

The present disclosure may be a self-emulsifying composition comprising 50 to 95% by weight in total of EPAs of preferably 60% by weight or more, more preferably 90% by weight or more, and still more preferably 96.5% by weight or more in total of the fatty acids and their derivatives. In some cases, the pharmaceutical composition may comprise at least about 40%, 46%, 50%, 55%, 60%, 65%, 70%, 75%, 80%, 85%, 90%, 95%, 96%, 96.5% or 98% EPAs in total of the fatty acids and their derivatives. In some cases, the pharmaceutical composition may comprise at most about 40%, 46%, 50%, 55%, 60%, 65%, 70%, 75%, 80%, 85%, 90%, 95%, 96%, 96.5% or 98% EPAs in total of the fatty acids and their derivatives. EPAs can be administered to patients in a highly purified form, including the product known as Epadel® (Mochida Pharmaceutical Co., Ltd., Tokyo Japan) and pharmaceutically acceptable amides, salts, esters and phospholipids thereof.

The EPAs used in the present disclosure may be synthetic, semi-synthetic, natural EPAs, or a natural oil containing such EPAs. Examples of natural EPAs include an extract from a natural oil containing an EPAs, a crudely purified natural oil containing EPAs, and a highly purified natural oil containing an EPAs produced by a method known in the art. Exemplary semi-synthetic EPAs include EPAs produced by a microorganism or the like and the EPAs or the natural EPAs which have been subjected to a chemical treatment such as esterification or ester exchange.

B. Formulation

In some embodiments, omega-3 fatty acids are formulated as a self-emulsifying composition. Self-emulsifying composition of the present disclosure may preferably have at least one of the effects including excellent self-emulsifying property, excellent dispersibility in the composition, excellent emulsion stability, excellent storage stability, excellent absorption property, and in particular, excellent absorption property and rate under fasting, and excellent convenience or compliance for the patients so that the composition can exhibit pharmacological effect of the EPAs. In some cases, EPAs may be combined with 5 to 50% by weight of an emulsifier having an HLB of at least 10.

In some cases, the pharmaceutical composition may comprise at least about 5%, 10%, 15%, 20%, 25%, 30%, 35%, 40%, 45%, and 50% emulsifier. In some cases, the pharmaceutical composition may comprise at most about 5%, 10%, 15%, 20%, 25%, 30%, 35%, 40%, 45% and 50% emulsifier. The self-emulsifying composition is free from ethanol or the ethanol content is low. The present disclosure also provides a drug of such self-emulsifying composition, its production method, and the method of its use.

Examples of the pharmaceutically acceptable salts of the EPAs include inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as mono-, di- and TG. Preferable examples include ethyl ester and TG ester, and the more preferred is ethyl ester. More specifically, preferable examples include EPA-E, TG ester of EPAs, and the like.

The EPAs used for the starting material of the self-emulsifying composition of the present disclosure is not particularly limited for its purity. The purity is typically such that content of the EPAs in total of the fatty acids and their derivatives in the composition of the present disclosure could be preferably at least 40%, 45%, 46.5%, 50%, 51%, 52%, 53%, 54%, 55%. 56%, 57%, 58%, 59%, 60%, 65%, 70%, 75% by weight, more preferably at least 80% by weight, still more preferably at least 85% by weight, still more preferably at least 90% by weight, and most preferably at least 96.5% by weight. The EPAs containing EPAs and DHAs at a high purity, for example, the one with the content of (EPAs+DHAs) in relation to the EPAs of at least 50%, 55%, 60%, 65%, 70%, 75%, 80%, 85% by weight in total of the fatty acids and their derivatives is preferable, and the content is more preferably at least 90% by weight in total of the fatty acids and their derivatives, still more preferably at least 96.5% by weight in total of the fatty acids and their derivatives, and most preferably at least 98% by weight in total of the fatty acids and their derivatives. In other words, the composition of the present disclosure preferably has a high purity of EPAs in the total fatty acid.

For example, when EPA-E and DHA-E are used, compositional ratio of EPA-E/DHA-E and content of (EPA-E+DHA-E) in relation to total fatty acid are not particularly limited as long as the purity of EPAs in the composition of the present disclosure is in the range as described above. However, the compositional ratio of the EPA-E/DHA-E is preferably at least 0.5, 0.6, 0.7, 0.8, 0.9, 1.0, 1.1, 1.2, 1.5, more preferably at least 2.0, and most preferably at least 2.5.

The composition of the present disclosure may also contain an omega-3 polyunsaturated fatty acid other than the EPAs and DHAs such as DPA, hexadecatrienoic acid (HTA), alpha-linolenic acid (ALA), eicosatrienoic acid (ETE), stearidonic acid (SDA), eicosatetraenoic acid (ETA), heneicosapentaenoic acid (HPA), tetoracosapentaenoic acid (TPA) or tetracosahexaenoic acid (THA) or the pharmaceutically acceptable amide, salt or ester thereof. However, content of omega-3 polyunsaturated fatty acids other than the EPAs and DHAs preferably low, more preferably less than 60%, 55%, 50%, 45%, 40%, 35%, 30%, 25%, 20%, 15%, 10%, 5%, 4%, 3%, 2% by weight, still more preferably less than 1% by weight. The composition of the present disclosure may also contain an omega-6 polyunsaturated fatty acid other than the EPAs such as linoleic acid, γ linolenic acid, or dihomo-γ-linolenic acid or the pharmaceutically acceptable amide, salt or ester thereof. However, content of omega-6 polyunsaturated fatty acids preferably low, more preferably less than 5%, 4%, 3%, 2%, 1% and 0.5% by weight, still more preferably less than 0.2% by weight. In particular, the content of arachidonic acid or the pharmaceutically acceptable salts or esters is in total of the fatty acids and their derivatives preferably low, more preferably less than 2%, 1%, 0.5%, 0.2%, 0.1% by weight, still more preferably less than 0.05% by weight, and most preferably, the composition is substantially free from the arachidonic acid or the pharmaceutically acceptable salt or ester.

In some embodiments, the composition of the present invention comprises EPAs and DPA, alternatively EPAs, DPA and HPA, alternatively EPAs, DPA and TPA, alternatively EPAs, DPA, HPA and TPA. The preferable EPAs:DPA ratio is between 99:1 and 1:99, between 90:1 and 1:90, between 60:1 and 1:60, between 40:1 and 1:40, between 30:1 and 1:30, between 20:1 and 1:20, between 10:1 and 1:10, between 5:1 and 1:5 and between 2:1 and 1:2.

In some embodiments, the composition of the present invention comprise EPAs, DHAs and DPA, alternatively EPAs, DHAs, DPA and HPA, alternatively EPAs, DHAs, DPA and TPA, alternatively EPAs, DHAs, DPA, HPA and TPA. The preferable DHAs:DPA ratio is no more than 1:100, no more than 1:95, no more than 1/90, no more than 1:80, no more than 1/70, no more than 1:60, no more than 1:50, no more than 1:40, no more than 1:30, no more than 1:20, no more than 1:10, no more than 1:5, no more than 1:2, no more than 1:1, no more than 2:1, no more than 5:1, no more than 10:1, no more than 20:1, no more than 50:1 and no more than 100:1.

Compared to the fish oil or the fish oil concentrate, the EPA-E used in the composition or therapeutic agent of the present disclosure contains impurities such as saturated fatty acids and arachidonic acid which are unfavorable for cardiovascular events at a lower content, and this enables realization of the intended action without causing the problems of excessive nutrition or vitamin A intake. When the EPA-E in the form of ester is used, a sufficiently stable composition can be obtained by adding a commonly used antioxidant since the ester form has higher oxidation stability than the fish oils which are mainly TG form.

Purified fish oils may also be used for the EPAs, and use of monoglyceride, diglyceride, and TG derivatives and combinations thereof of the EPAs are also preferable embodiments. Various products containing the EPAs are commercially available, for example, Incromega™ DHA27, Incromega™ DHA46, Incromega™ DHA700E, Incromega™ DHA700TG, Incromega™ DHA 500TG, Incromega™ E400200, Incromega™ E4030, Incromega™ E4520, Incromega™ E460180, Incromega™ E5020, Incromega™ E530200, Incromega™ E6814, Incromega™ E1050, Incromega™ E1070, Incromega™ E3322, Incromega™ E3525, Incromega™ E3826, Incromega™ E7010, Incromega™ EPA500EE, Incromega™ EPA500TG, Incromega™ EPA700E, Incromega™ TG0525, Incromega™ TG1040, Incromega™ TG1050, Incromega™ TG3322, Incromega™ TG3322SR, Incromega™ TG4030, Incromega™ TG6015, Incromega™ TG7010, Incromega™ TrioEE and Incromega™ Trio EE (Croda International PLC, Yorkshire, England), and EPAX6500EE, EPAX6015TG, EPAX6015EE, EPAX6000TG, EPAX6000EE, EPAX6000TGN, EPAX6000FA, EPAX5500EE, EPAX5000TG, EPAX4510TG, EPAX4020TG, EPAX4020EE, EPAX2050TG, EPAX7010EE, EPAX1050TG, EPAX1050TGN, K85TG, K85EE, and K80EE (FMC Corporation, Philadelphia, U.S.A.). These products may be purchased and used for the composition of the present disclosure.

In the present disclosure, the "polyoxyethylene hydrogenated castor oil" is a compound prepared by addition polymerization of ethylene oxide to the hydrogenated castor oil which is castor oil having hydrogen added thereto, Various compounds with different average degree of polymerization of ethylene oxide are commercially available, and examples include polyoxyethylene (20) hydrogenated castor oil (NIKKOL HCO-20, Nikko Chemicals Co., Ltd.), polyoxyethylene (40) hydrogenated castor oil (NIKKOL HCO-40, Nikko Chemicals Co., Ltd.), polyoxyethylene (50) hydrogenated castor oil (NIKKOL HCO-50, Nikko Chemicals Co., Ltd.), polyoxyethylene (60) hydrogenated castor oil (NIKKOL HCO-60, Nikko Chemicals Co., Ltd.), and polyoxyethylene (100) hydrogenated castor oil (NIKKOL HCO-100, Nikko Chemicals Co., Ltd.), and the preferred is polyoxyethylene (60) hydrogenated castor oil. These may be used alone or in combination of two or more. In the present disclosure, the "polyoxyethylene hydrogenated castor oil" includes all of such compounds unless otherwise noted.

In the present disclosure, the "polyoxyethylene sorbitan fatty acid ester" is polyoxyethylene ether of a fatty acid ester wherein a part of the hydroxy groups of anhydrous sorbitol have been esterified with a fatty acid. Various compounds with different esterified fatty acid are commercially available, and examples include polyoxyethylene (20) sorbitan monolaurate (NIKKOL TL-10, Nikko Chemicals Co., Ltd.), polyoxyethylene (20) sorbitan monopalmitate (NIKKOL TP-10V, Nikko Chemicals Co., Ltd.), polyoxyethylene (20) sorbitan monostearate (NIKKOL TS-10V, Nikko Chemicals Co., Ltd.), polyoxyethylene (20) sorbitan tristearate (NIKKOL TS-30V, Nikko Chemicals Co., Ltd.), polyoxyethylene (20) sorbitan monoisostearate (NIKKOL TI-10V, Nikko Chemicals Co., Ltd.), polyoxyethylene (20) sorbitan monooleate (NIKKOL TO-10V, Nikko Chemicals Co., Ltd.), and polyoxyethylene (20) sorbitan trioleate (NIKKOL TO-30V, Nikko Chemicals Co., Ltd.), and the preferred are polyoxyethylene (20) sorbitan monolaurate, polyoxyethylene (20) sorbitan monopalmitate, polyoxyethylene (20) sorbitan monostearate, and polyoxyethylene (20) sorbitan monooleate, and the more preferred are polyoxyethylene (20) sorbitan monooleate. These may be used alone or in combination of two or more, In the present disclosure, the "polyoxyethylene sorbitan fatty acid ester" includes all of such compounds unless otherwise noted.

In the present disclosure, the "polyoxyethylene castor oil" is a compound prepared by addition polymerization of ethylene oxide to castor oil. Various compounds having different average ethylene oxide mole number are commercially available, and examples include Kolliphor EL (BASF), Kolliphor EL-P (BASF), NIKKOL CO-3 with an average ethylene oxide mole number of 3 (Nikko Chemicals Co., Ltd.), NIKKOL CO-10 with an average ethylene oxide mole number of 10 (Nikko Chemicals Co., Ltd.), EMALEX C-20 with an average ethylene oxide mole number of 20 (Nippon Emulsion Co., Ltd.), EMALEX C-30 with an average ethylene oxide mole number of 30 (Nippon Emulsion Co., Ltd.), EMALEX C-40 with an average ethylene oxide mole number of 40 (Nippon Emulsion Co., Ltd.), and EMALEX C-50 with an average ethylene oxide mole number of 50 (Nippon Emulsion Co., Ltd.). These may be used alone or in combination of two or more. In the present disclosure, the "polyoxyethylene castor oil" includes all of such compounds unless otherwise noted.

In the present disclosure, the "polyethylene glycol fatty acid ester" is a fatty acid ester of a polyethylene glycol which is a fatty acid polymerized with ethylene oxide. Various compounds with different esterified fatty acid are commercially available, and examples include polyethylene glycol monolaurate (NIKKOL MYL-10, Nikko Chemicals Co., Ltd.), polyethylene glycol monostearate (NIKKOL MYS-10V, MYS-25V, MYS-40V, NYS-45V, and MYS-55V, Nikko Chemicals Co., Ltd.), polyethylene glycol monooleate (NIKKOL MYO-6 and MYO-10, Nikko Chemicals Co., Ltd.), polyethylene glycol distearate (NIKKOL CDS-6000P, Nikko Chemicals Co., Ltd.), and polyethylene glycol diisostearate (NIKKOL CDIS-400, Nikko Chemicals Co., Ltd.). These may be used alone or in combination of two or more. In the present disclosure, the "polyethylene glycol fatty acid ester" includes all of such compounds unless otherwise noted.

In the present disclosure, the "polyoxyethylene polyoxypropylene glycol" is a compound prepared by addition polymerization of ethylene oxide to the polypropylene glycol which is a polymerized propylene oxide. Various compounds having different average degree of polymerization of the propylene oxide and the ethylene oxide are commercially available, and examples include polyoxyethylene (3) polyoxypropylene (17) glycol (Adeka Pluronic L-31, ADEKA), polyoxyethylene (20) polyoxypropylene (20) glycol (Adeka Pluronic L-44, ADEKA), polyoxyethylene (42) polyoxypropylene (67) glycol (Adeka Pluronic P-123, ADEKA), polyoxyethylene (54) polyoxypropylene (39) glycol (Newdet PE-85, Sanyo Chemical Industries, Ltd.), polyoxyethylene (105) polyoxypropylene (5) glycol (PEP101, Sanyo Chemical Industries, Ltd.), polyoxyethylene (120) polyoxypropylene (40) glycol (Adeka Pluronic F-87, ADEKA), polyoxyethylene (160) polyoxypropylene (30) glycol (Adeka Pluronic F-68, ADEKA), polyoxyethylene (196) polyoxypropylene (67) glycol (Lutrol F127, BASF Japan), and polyoxyethylene (200) polyoxypropylene (70) glycol, and the preferred is polyoxyethylene (105) polyoxypropylene (5) glycol. These may be used alone or in combination of two or more. In the present disclosure, the "polyoxyethylene polyoxypropylene glycol" includes all of such compounds unless otherwise noted.

In the present disclosure, the "sucrose fatty acid ester" is an ester of sugar and a fatty acid. Various compounds with different types of the esterified fatty acids and degree of esterification are commercially available, and examples include Surfhope SE PHARMA J-1216 containing 95% of lauric acid in the fatty acid (Mitsubishi-Kagaku Foods Corporation), Surfhope SE PHARMA J-1416 containing 95% of myristic acid in the fatty acid (Mitsubishi-Kagaku Foods Corporation), Surfhope SE PHARMA J-1615 and J-1616 containing 80% of palmitic acid in the fatty acid, (Mitsubishi-Kagaku Foods Corporation), J-1811, J-1815, and J-1816 containing 70% of stearic acid in the fatty acid (Mitsubishi-Kagaku roods Corporation), and Surfhope SE PHARMA J-1715 containing 70% of oleic acid in the fatty acid, which may be used alone or in combination of two or more. The "sucrose fatty acid ester" used in the present disclosure include all of such compounds.

The emulsifier added to a self-emulsifying composition of the present disclosure may have an HLB of at least 10, preferably at least 11, and more preferably at least 12.

Total content of the emulsifier having an HLB of at least 10 in the self-emulsifying composition of the present disclosure is not particularly limited as long as it is at least 10 parts by weight in relation to 100 parts by weight of the EPAs. The content is typically 10 to 100 parts by weight, preferably 10 to 80 parts by weight, and more preferably 10 to 50 parts by weight in relation to 100 parts by weight of the EPAs.

In the present disclosure, the "sorbitan fatty acid ester" is an ester of anhydrous sorbitol and a fatty acid. Various compounds with different types of the esterified fatty acids and degree of esterification are commercially available, and examples include sorbitan monolaurate (NIKKOL SL-10, Nikko Chemicals Co., Ltd.), sorbitan monostearate (NIKKOL SS-10MV, Nikko Chemicals Co., Ltd.), sorbitan monooleate (NIKKOL SO-10V, Nikko Chemicals Co., Ltd.), sorbitan monopalmitate (NIKKOL SP-10V, Nikko Chemicals Co., Ltd.), sorbitan trioleate (NIKKOL SO-30, Nikko Chemicals Co., Ltd.), and sorbitan sesquioleate (NIKKOL SO-15MV, Nikko Chemicals Co., Ltd.).

In the present disclosure, the "glycerin fatty acid ester" is an ester of monoglycerin or polyglycerin and a fatty acid. Various compounds with different types of the esterified fatty acids and degree of esterification are commercially available, and examples include glyceryl monooleate (PECEOL), glyceryl monostearate (NIKKOL MGS-F50SEV, Nikko Chemicals Co., Ltd.), decaglyceryl monooleate (NIKKOL Decaglyn 1-0V, Nikko Chemicals Co., Ltd.). decaglyceryl monolaurate (NIKKOL Decaglyn 1-L, Nikko Chemicals Co., Ltd.). decaglyceryl trioleate (NIKKOL Decaglyn 3-OV, Nikko Chemicals Co., Ltd.). and tetraglyceryl monooleate (NIKKOL Tetraglyn 1-OV, Nikko Chemicals Co., Ltd.).

In the present disclosure, the "lecithin" is a type of glycerophospholipid, and examples include soybean lecithin, enzymatically decomposed soybean lecithin, hydrogenated soybean lecithin, egg yolk lecithin, hydrogenated phospholipid, phospholipid from milk, lysolecithin, phosphatidyl choline, and phosphatidyl serine. The preferred are soybean lecithin, enzymatically decomposed soybean lecithin, hydrogenated soybean lecithin, and egg yolk lecithin, and the more preferred are soybean lecithin. These may be used alone or in combination of two or more. In the present disclosure, the "lecithin" includes all of such compounds unless otherwise noted.

Commercially available products include purified soybean lecithin (Nisshin Oilio), purified egg yolk lecithin (Asahi Kasei Pharma Corporation), and egg yolk lecithin PL-100M (Kewpie Corporation), and use of such product is also possible.

In the present disclosure, the "polyhydric alcohol" is a polyol compound having the structure of a straight chain or cyclic aliphatic hydrocarbon wherein two or more carbon atoms are each substituted with one hydroxy group. Exemplary such polyhydric alcohols include divalent alcohols such as ethyleneglycol, propylene glycol, trimethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexane triol, and polyhydric alcohol polymers such as diethylene glycol, dipropylene glycol, triethylene glycol, polyethylene glycol, polypropylene glycol, and polyglycerin, and the preferred are propylene glycol or glycerin. In the present disclosure, the "polyhydric alcohol" includes all of such compounds unless otherwise noted.

Total amount of the lecithin and/or the polyhydric alcohol added in the self-emulsifying composition of the present disclosure is not particularly limited. However, the total amount of the lecithin and/or the polyhydric alcohol is typically 0 to 50 parts by weight, preferably 3 to 40 parts by weight, and more preferably 5 to 30 parts by weight in relation to 100 parts by weight of the EPA-E.

The ethanol in the self-emulsifying composition of the present disclosure is preferably used at an amount not causing quality change in the course of capsulation, distribution, or storage, at an amount not causing change in the content of the capsule, and at an amount not exceeding the established upper limit of the daily dose as a drug. The ethanol content is typically up to 10% by weight, preferably up to 4% by weight, more preferably up to 1% by weight, more preferably up to 0.5% by weight, more preferably up to 0.2% by weight, still more preferably up to 0.1% by weight, and most preferably 0% by weight (no ethanol addition).

Preferable ethanol concentration can be adequately determined in consideration of the EPA-E concentration in the self-emulsifying composition and the daily dose. When the self-emulsifying composition of the present disclosure is orally administered at a daily dose in terms of the EPA-E of 1800 mg, and for example, the preparation contains 75% by weight of the EPA-E, the maximum daily dose of 3.26 mg described in "Dictionary of Drug Additives (in Japanese)" will not be exceeded when the ethanol content is not more than 0.135% by weight.

The preferable embodiment of the self-emulsifying composition of the present disclosure containing such EPAs and an emulsifier is a combination of EPAs and/or DHAs with at least one emulsifier selected from the group consisting of polyoxyethylene hydrogenated castor oil, polyoxyethylene sorbitan fatty acid ester, polyoxyethylene castor oil, sucrose fatty acid ester, sorbitan fatty acid ester, glycerin fatty acid ester and lecithin. When the self-emulsifying composition of the present disclosure is used as a food such as special purpose food, functional health food, and health food, the preferred is the combination of EPAs and/or DHAs with a sucrose fatty acid ester and/or a lecithin which has good results as a food additive. When a sucrose fatty acid ester is used, the preferable amount is 1% by weight to 20% by weight, more preferably 4% by weight to 20% by weight, and most preferably 4% by weight to 10% by weight in the self-emulsifying composition. The most preferable embodiments are a combination of EPAs and polyoxyethylene (50) hydrogenated castor oil or polyoxyethylene (60) hydrogenated castor oil; a combination of EPAs and polyoxyethylene (20) sorbitan monooleate; a combination of EPAs and polyoxyethylene castor oil; and a combination of EPAs and sucrose fatty acid ester J-1216 or J-1816.

Also preferred is the further combination with a lecithin such as soybean lecithin and/or a polyhydric alcohol such as propylene glycol.

When the emulsifier is at least one member selected from the group consisting of polyoxyethylene hydrogenated castor oil, polyoxyethylene sorbitan fatty acid ester, and polyoxyethylene castor oil, the polyhydric alcohol is preferably a dihydric alcohol, and use of propylene glycol is more preferable. When the emulsifier is a sucrose fatty acid ester, the polyhydric alcohol is preferably a trihydric alcohol, and use of glycerin is more preferable.

Preferably, the composition and therapeutic agent of the present disclosure is substantially free from water. The "substantially free from water" means that the water content is up to 10% by weight. The water is preferably used at an amount of 0.5 to 6% by weight, more preferably at 0.5 to 4% by weight, more preferably at 0.5 to 3% by weight, and most preferably at 1 to 3% by weight when the total amount of the self-emulsifying composition is 100% by weight.

The self-emulsifying composition of the present disclosure may also contain additives such as an emulsion aid, stabilizer, antiseptic, surfactant, and antioxidant. Exemplary emulsion aids include fatty acids containing 12 to 22 carbon atoms such as stearic acid, oleic acid, linoleic acid, palmitic acid, linolenic acid, and myristic acid and their salts. Exemplary stabilizers include phosphatidic acid, ascorbic acid, glycerin, and cetanols, and exemplary antiseptics include ethyl paraoxybenzoate and propyl paraoxybenzoate. Exemplary surfactants include sucrose fatty acid esters, sorbitan fatty acid esters, glycerin fatty acid esters, polyglycerin fatty acid esters, polyoxyethylene sorbitan fatty acid esters, polyoxyethylene alkyl ethers, polyoxyethylene fatty acid esters, polyoxyethylene alkyl phenyl ethers, and polyoxyethylene polyoxypropylene alkyl ethers having an HLB of less than 10. Exemplary antioxidants include oil-soluble antioxidants such as butylated hydroxy toluene, butylated hydroxy anisole, propyl gallate, propyl gallate, pharmaceutically acceptable quinone, astaxanthin, and α-tocopherol.

In addition, an adequate carrier or mediator, a colorant, a flavor, and optionally, a vegetable oil or an additive such as non-toxic organic solvent or non-toxic solubilizing agent (for example glycerin), emulsifier, suspending agent (for example, Tween 80 and gum arabic solution), isotonic agent, pH adjusting agent, stabilizer, corrective, flavoring agent, preservative, antioxidant, or absorption promoter commonly used in the art may be adequately combined to prepare an appropriate pharmaceutical preparation.

More specifically, since the EPAs are highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition. Storage temperature is preferably room temperature, and frozen storage is preferably avoided since the freezing may result in the loss of self-emulsifying property, dispersibility in the composition, or emulsion stability.

The self-emulsifying composition of the present disclosure can be produced by mixing the EPAs, the emulsifier having an HLB of at least 10, sorbitan fatty acid ester or glycerin fatty acid ester, and the optionally added components such as lecithin, polyhydric alcohol, water and antioxidant with optional heating to dissolve the components.

In some cases, the pharmaceutical composition may comprise additional elements which may include but are not limited to antihypertensives such as angiotensin II receptor blockers such as irbesartan, olmesartan medoxomil, candesartan cilexetil, telmisartan, valsartan, and losartan potassium; angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine; a receptor blocker such as tolazoline, and phentolamine; β receptor blockers such as atenolol, metoprolol, acebutolol, propranolol, pindolol, carvedilol, and labetalol hydrochloride; a receptors stimulant such as clonidine and methyldopa; and diuretics such as eplerenone, hydrochlorothiazide, and furosemide.

In some cases, the pharmaceutical composition may comprise additional elements which may include but are not limited to antidiabetics as described herein.

In some cases, the pharmaceutical composition may comprise additional elements which may include but are not limited to vitamins such as ascorbic acid (vitamin C), tocopherol (vitamin E), and tocopherol nicotinate, and N-acetylcysteine, probucol.

In some cases, the pharmaceutical composition may comprise additional elements which may include but are not limited to blood flow improving agents such as aspirin, cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, and shimotsu-to extract.

In some cases, the pharmaceutical composition may comprise additional elements which may include but are not limited to bile acid derivatives, which are optionally farnesoid X receptor (FXR) ligand, such as ursodeoxycholic acid, chenodeoxycholic acid, obeticholic acid, GW4064, bile powder, deoxycholic acid, cholic acid, bile extract, bear bile, oriental bezoar, and dehydrocholic acid. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin.

C. Administration and Dosage

Compositions comprising EPAs useful for the disclosure include commercially available compositions of EPAs, such as Epadel®, Lovaza™, Omacor™, Lotriga™, or Vascepa™ noted above or developing composition such as Epanova™ (Omthera, Astrazeneca) or MAT9001 (Matinas Biopharma). Compositions comprising EPAs may be administered in tablet, capsule, powder or any other solid oral dosage form, as a liquid, as a soft gel capsule or other capsule form, or other appropriate and convenient dosage forms for administration to a patient in need thereof. Compositions can also include pharmaceutically acceptable excipients known to those of ordinary skill in the art including surfactants, oils, co-solvents or combinations of such excipients, together with stabilizers, emulsifiers, preservatives, solubilizers and/or other non-active pharmaceutical ingredients known to those of skill in the art relative to the preparation of pharmaceutical compositions.

The dose and dosage period of the EPAs used in the self-emulsifying composition of the present disclosure is a dose and period sufficient for realizing the intended action, which may be adequately adjusted depending on the administration route, frequency of administration per day, seriousness of the symptoms, body weight, age, and other factors.

A composition of the present disclosure may be administered to the patient orally, endorectally, or transvaginally. However, oral administration is preferable in the case of the patient who can take the drug orally, and the composition may be administered in the form of a jelly preparation in the case of patients undergoing dialysis or patients with aphagia by jelling the composition with gelatin or the like.

Doses of the aforementioned compositions as the active ingredient can be suitably decided depending on the purpose of administration, i.e., therapeutic or preventive treatment, nature of a disease to be treated or prevented, conditions, body weight, age, sexuality and the like of a patient. The practically desirable method and sequence for administration varies depending on the purpose of administration, i. e., therapeutic or preventive treatment, nature of a disease to be treated or prevented, conditions, body weight, age, sexuality and the like of a patient. The optimum method and sequence for administration of the compounds described in detail herein under preset given conditions may be suitably selected by those skilled in the art with the aid of the routine technique and the information contained in the present specification and field of invention.

In the case of oral administration, the composition may be administered at a dose in terms of the EPAs of 0.05 to 10 g/day, 0.1 to 5 g/day, 0.2 to 4 g/day, 0.3 to 3 g/day, 0.4 to 2 g/day, 0.5 to 1 g/day, preferably 0.2 to 4 g/day, 0.3 to 3.6 g/day, 0.6 to 2.7 g/day, 0.9 to 1.8 g/day, more preferably 0.3 to 3.0 g/day, 0.5 to 2.5 g/day, 1.0 to 2.0 g/day and most preferably 0.6 to 2.7 g/day, 0.9 to 1.8 g/day in 1 to 3 divided doses. In the case of oral administration, the composition may be administered at a dose in terms of the EPAs of 0.1 g/day, 0.3 g/day, 0.5 g g/day, 0.6 g/day, 0.9 g/day, 1.0 g/day, 1.2 g/day, 1.5 g/day, 1.8 g/day, 2.0 g/day, 2.1 g/day, 2.4 g/day, 2.5 g/day, 2.7 g/day, 3.0 g/day, 3.3 g/day, 3.5 g/day, 3.6 g/day, 3.9 g/day, 4.0 g/day, 4.2 g/day, 4.5 g/day, 4.8 g/day, 5.0 g/day, 5.1 g/day, 5.4 g/day, 5.5 g/day, 5.7 g/day, 6.0 g/day, 6.3 g/day, 6.5 g/day, 6.6 g/day, 6.9 g/day, 7.0 g/day, 7.2 g/day, 7.5 g/day, 7.8 g/day, 8.0 g/day, 8.1 g/day, 8.4 g/day, 8.5 g/day, 8.7 g/day, 9.0 g/day, 9.3 g/day, 9.5 g/day, 9.6 g/day, 9.9 g/day and 10.0 g/day in 1 to 3 divided doses. However, the entire dose may be administered at once or in several divided doses. While meal affects absorption of the EPAs, and the administration of the EPAs is preferably conducted during the meal or after the meal, and more preferably immediately after the meal (within 30 minutes after the meal), the self-emulsifying composition of the present disclosure has excellent absorption under fasting, and therefore, it exhibits the intended effects even when administered at a timing other than during, after, or immediately after the meal, for example, before or immediately before the meal or before going to the bed; to patients with reduced absorption ability of the intestinal tract (for example, elderly, patients of intestinal disease, patients after intestinal surgery, terminal cancer patients, or patients taking a lipase inhibitor); or used at a reduced dose.

The compositions of EPAs are administered according to the disclosure to a subject or patient to provide the patient with a dosage of about 0.3-10 g per day of EPAs, alternatively 0.5-8 g per day, alternatively 0.6-6 g per day, alternatively 1-4 g per day, alternatively 0.9-3.6 g per day or specifically about 1800 mg per day or about 2700 mg per day of EPAs.

The composition to be administered can contain other fatty acids, especially any omega-3 unsaturated fatty acid, especially DHAs. The ratio of EPAs/DHAs in the composition, the content of EPAs and DHAs in the total fatty acids and administration amount of EPAs and DHAs are not limited but the ratio is preferably 0.8 or more, more preferably 1.0 or more, still more preferably 1.2 or more. The composition is preferably highly purified; for example, the proportion of EPAs+DHAs in the fatty acids and their derivatives is preferably 40%, 45%, 50%, 55%, 60%, 65%, 70%, 75%, 80%, 85% by weight or more, more preferably 90% by weight or more, and still more preferably 96.5% by weight or more. The daily amount in terms of EPAs+DHAs is typically 0.3 to 10.0 g/day, preferably 0.5 to 6.0 g/day, and still more preferably 1.0 to 4.0 g/day, alternatively 0.9-3.6 g per day or specifically about 1800 mg per day or about 2700 mg per day of EPAs+DHAs. The low content of other long chain saturated fatty acids is preferred, and among the long chain unsaturated fatty acids, the content of omega-6 fatty acids, and in particular, the content of arachidonic acid in total of the fatty acids and their derivatives is preferably as low as less than 2%, 1%, 0.5%, 0.2%, 0.1% by weight, and more preferably less than 0.05% by weight. For example, soft capsule (Lovaza™, Omacor™ and Lotriga™) containing about 46% by weight of EPA-E and about 38% by weight of DHA-E is commercially available in the U.S. and other countries as a therapeutic agent for hypertriglyceridemia and soft capsule (Vascepa™) containing at least 96% by weight of EPA-E is commercially available in the U.S as a therapeutic agent for hypertriglyceridemia and soft capsule (Epanova™) containing about 50-60% by weight of EPA and about 15-25% by weight of DHA and MTA9001 containing EPAs and DHAs are developed in the U.S. as a therapeutic agent for hypertriglyceridemia.

Patients treated for NASH can be administered EPAs according to the disclosure for 3, 6 or 9 months, or for 1 year, 2 years, 3 years, 4 years, 5 years or more and can be administered EPAs in one, two or three dosage per day, or other multiple doses per day including 1 to about 10, 1 to 8, 1 to 6, 1 to 4 or 1 to 2 dosage units per day as appropriate for patient therapy. The term "dose unit" and "dosage unit" herein refer to a portion of a pharmaceutical composition that contains an amount of EPAs for a single administration to a subject.

When orally administered at such dose, the administration period may be adequately determined depending on the target disease and degree of symptoms. For example, in the case of administration for NASH, the administration period is not particularly limited as long as improvements of biochemical markers related to NASH, improvement in the pathological conditions or therapeutic effects, and suppression of the progress in metabolic syndrome, cardio or cerebrovascular event, or ulcer and gangrene of extremities and peripheries are realized. However, administration period is determined to realize the improvements in the concentration of plasma lipid marker (total cholesterol (hereinafter abbreviated as Cho), TG, postprandial TG, low-density lipoprotein Cho, high-density lipoprotein Cho, very-low-density lipoprotein Cho, non-high-density lipoprotein Cho, intermediate-density lipoprotein Cho, very-high-density lipoprotein Cho, free fatty acid, phospholipid, chylomicron, ApoB, lipoprotein (a), remnant-like lipoprotein Cho, small dense low-density lipoprotein Cho, etc.), increase in the skin temperature of extremities and peripheries which can be measured by thermography or the like, increase in the walking distance, increase in the serum CPK or other test value, and improvement of various symptoms such as numbness, coldness, ache, pain at rest, itching, cyanosis, flare, chilblain, neck stiffness, anemia, poor complexion, itching, and crawling. The amelioration or therapeutic effects may be monitored by other biochemical, pathological, or symptomatic parameters related to NASH. The administration is preferably continued as long as abnormality is observed in biochemical index such as serum lipid concentration or pathology. In addition, the composition may be administered every alternate day or 2 or 3 days in a week, or as the case may be, a drug withdrawal period of about 1 day to 3 month, and more preferably about 1 week to 1 month may be included.

If indicated by the physician, oral administration may be started at a dose lower than the recommended daily EPAs dose at the first day, and then, the dose may be gradually increased to the maximum daily dose as the maintenance dose. The dose may be reduced depending on the conditions of the patient. Lower daily dose is preferable in view of reducing the side effects, and administration of once or twice a day is preferable in view of the drug compliance.

The method of the present invention may administer a therapeutically effective amount of a pharmaceutical composition comprising EPAs in combination with a second effective component. The second effective component may be adequately determined depending on the target disease and the seriousness of the symptom. However, the second effective component is preferably a component that does not adversely affect the effects of EPAs, and examples include therapeutic agent for hyperlipidemia, antihypertensives, antidiabetics, antioxidants, blood flow improving agents, farnesoid X receptor (FXR) ligands and bile acid derivatives. The more preferable second effective component is agent for hyperlipidemia, antihypertensives, antidiabetics and farnesoid X receptor (FXR) ligands.

Of the preferable examples of the second effective component, exemplary therapeutic agents for hyperlipidemia include polyenephosphatidylcholine, unsaponifiable soybean oil (soy sterol), gamma-oryzanol, riboflavin butyrate, dextran sulfate sodium sulfur 18, pantethine, niceritorol and elastase; statins such as lovastatin, pravastatin, simvastatin, atorvastatin, fluvastatin, pitavastatin, rosuvastatin, and cerivastatin; fibrates such as simfibrate, clofibrate, clinofibrate, bezafibrate, and fenofibrate; lipolytic enzyme inhibitors such as orlistat and cetilistat; resins such as colestyramine and colestimide; and ezetimibe. The preferable agents for hyperlipidemia are statins such as lovastatin, pravastatin, simvastatin, atorvastatin, fluvastatin, pitavastatin, rosuvastatin, and cerivastatin; fibrates such as simfibrate, clofibrate, clinofibrate and bezafibrate; proprotein convertase subtilisin/kexin type 9 (PCSK9) antibody such as Evolocumab (Amgen, AMG145), SAR236553/Regn727 (sanofi and Regeneron), RN316 (Pfizer) and LGT209 (Novartis); and ezetimibe. The more preferable agents for hyperlipidemia are statins such as pravastatin, simvastatin, atorvastatin, fluvastatin, pitavastatin, rosuvastatin, and cerivastatin.

Exemplary antihypertensives include angiotensin II receptor blockers such as irbesartan, olmesartan medoxomil, candesartan cilexetil, telmisartan, valsartan, and losartan potassium; angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine; [alpha] receptor blocker such as tolazoline, and phentolamine; [beta] receptor blockers such as atenolol, metoprolol, acebutolol, propranolol, pindolol, carvedilol, and labetalol hydrochloride; a receptors stimulant such as clonidine and methyldopa; and diuretics such as eplerenone, hydrochlorothiazide, and furosemide. The preferable antihypertensives are angiotensin II receptor blockers such as irbesartan, olmesartan medoxomil, candesartan cilexetil, telmisartan, valsartan, and losartan potassium, angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate and calcium antagonists such as azelnidipine, amlodipine besylate, cilnidipine, nicardipine hydrochloride, nifedipine and manidipine. The more preferable antihypertensives are angiotensin II receptor blockers such as irbesartan, olmesartan medoxomil, candesartan cilexetil, telmisartan, valsartan, and losartan potassium, angiotensin-converting enzyme inhibitors such as imidapril hydrochloride, enalapril maleate, captopril, and lisinopril hydrate and calcium antagonists such as azelnidipine, amlodipine besylate, and cilnidipine.

Exemplary antidiabetics include [alpha]-glucosidase inhibitors such as acarbose, voglibose, and miglitol; sulfonyl urea hypoglycemics such as gliclazide, glibenclamide, glimepiride, and tolbutamide; fast-acting insulin secretagogues such as nateglinide and mitiglinide; biguanide hypoglycemics such as metformin hydrochloride and buformin hydrochloride; dipeptidyl phosphatase 4 inhibitors such as sitagliptin, vildagliptin, alogliptin, linagliptin and saxagliptin; thiazolidine reagents such as pioglitazone hydrochloride and rosiglitazone maleate; glucagon-like peptide 1 derivative reagents such as exenatide, lixisenatide and liraglutide; PPARα/γ dual agonists such as AR-H039242, GW-409544, BVT-142, CLX-0940, GW-1536, GW-1929, GW-2433, KRP-297, L-796449, LR-90, LY-578, LY-4655608, LSN-862, LY-510929, LY-929, DRF4158, MK-0767, SB 219994, muraglitazar, tesaglitzar, reglitazar and farglitazar; PPARα/δ dual agonists such as GFT505 and TIPP401; and SGLT2 inhibitors such as canagliflozin, dapagliflozin, Luseogliflozin, tofogliflozin, empagliflozin, ipragliflozin, BI44847, LX-4211, DSP-3235/GSK1614235 and ISIS388626. The preferable antidiabetics are [alpha]-glucosidase inhibitors such as acarbose and voglibose, sulfonyl urea hypoglycemics such as glibenclamide, glimepiride and tolbutamide, fast-acting insulin secretagogues such as nateglinide and mitiglinide, biguanide hypoglycemics such as metformin hydrochloride and buformin hydrochloride, dipeptidyl phosphatase 4 inhibitors such as sitagliptin, vildagliptin, alogliptin, linagliptin and saxagliptin, thiazolidine reagents such as pioglitazone hydrochloride and rosiglitazone maleate, glucagon-like peptide 1 derivative reagents such as exenatide, lixisenatide and liraglutide, PPARα/γ dual agonists such as muraglitazar, tesaglitzar, reglitazar and farglitazar, PPARα/δ dual agonists such as GFT505, and SGLT2 inhibitors such as canagliflozin, dapagliflozin, luseogliflozin, tofogliflozin, empagliflozin and ipragliflozin. The more preferable antidiabetics are sulfonyl urea hypoglycemics such as glibenclamide, glimepiride and tolbutamide, biguanide hypoglycemics such as metformin hydrochloride and buformin hydrochloride, dipeptidyl phosphatase 4 inhibitors such as sitagliptin, vildagliptin, alogliptin, linagliptin and saxagliptin, thiazolidine reagents such as pioglitazone hydrochloride and rosiglitazone maleate, glucagon-like peptide 1 derivative reagents such as exenatide, lixisenatide and liraglutide, PPARα/γ dual agonists such as muraglitazar, tesaglitzar, reglitazar and farglitazar, and SGLT2 inhibitors such as canagliflozin, dapagliflozin, Luseogliflozin, tofogliflozin, empagliflozin and ipragliflozin. The most preferable antidiabetics are dipeptidyl phosphatase 4 inhibitors such as sitagliptin, vildagliptin, alogliptin, linagliptin and saxagliptin and thiazolidine reagents such as pioglitazone hydrochloride and rosiglitazone maleate.

The dose of the second effective component is not particularly limited since such dose depends on the conditions and body type of the individual patient. However, exemplary such daily dose of the second effective component is equal or less than the recommended daily dose of mono-therapy. In the case of lovastatin is less than the recommended daily dose of 10 mg/day, preferably at least 0.2 mg and up to 8 mg, more preferably at least 0.4 mg and up to 6 mg, and still more preferably at least 1 mg and up to 4 mg; in the case of pravastatin sodium salt, less than the recommended daily dose of 40 mg/day, preferably at least 1 mg and up to 30 mg, more preferably at least 2 mg and up to 25 mg, and still more preferably at least 4 mg and up to 20 mg; in the case of simvastatin, less than the recommended daily dose of 1 day 5 mg, preferably at least 0.1 mg and up to 4 mg, more preferably at least 0.2 mg and up to 2 mg, and still more preferably at least 0.4 mg and up to 1 mg; in the case of atorvastatin calcium hydrate, less than the recommended daily dose of 20 mg/day, preferably at least 0.4 mg and up to 16 mg, more preferably at least 0.8 mg and up to 12 mg, and still more preferably at least 2 mg and up to 10 mg; in the case of fluvastatin sodium salt, less than the recommended daily dose of 20 mg/day, preferably at least 0.4 mg and up to 16 mg, more preferably at least 0.8 mg and up to 12 mg, and still more preferably at least 1.5 mg and up to 8 mg; in the case of pitavastatin calcium salt, less than the recommended daily dose of 1 day 1 mg, preferably at least 0.02 mg and up to 0.8 mg, more preferably at least 0.04 mg and up to 0.6 mg, and still more preferably at least 0.1 mg and up to 0.4 mg; in the case of rosuvastatin calcium salt, less than the recommended daily dose of 2.5 mg, preferably at least 0.05 mg and up to 2 mg, more preferably at least 0.1 mg and up to 1.5 mg, and still more preferably at least 0.2 mg and up to 1 mg and in the case of bezafibrate, less than the recommended daily dose of 800 mg, preferably at least 50 mg and up to 600 mg, more preferably at least 100 mg and up to 500 mg, and still more preferably at least 200 mg and up to 400 mg.

In the case of irbesartan, less than the recommended daily dose of 50 mg/day, preferably at least 1 mg and up to 40 mg, more preferably at least 2 mg and up to 30 mg, and still more preferably at least 5 mg and up to 20 mg; in the case of olmesartan medoxomil, less than the recommended daily dose of 10 mg/day, preferably at least 0.2 mg and up to 8 mg, more preferably at least 0.5 mg and up to 6 mg, and still more preferably at least 1 mg and up to 4 mg; in the case of candesartan cilexetil, less than the recommended daily dose of 4 mg/day, preferably at least 0.1 mg and up to 3 mg, more preferably at least 0.2 mg and up to 2 mg, and still more preferably at least 0.4 mg and up to 1 mg; in the case of telmisartan, less than the recommended daily dose of 20 mg/day, preferably at least 0.5 mg and up to 15 mg, more preferably at least 1 mg and up to 10 mg, and still more preferably at least 2 mg and up to 5 mg; in the case of valsartan, less than the recommended daily dose of 40 mg/day, preferably at least 1 mg and up to 30 mg, more preferably at least 2 mg and up to 20 mg, and still more preferably at least 4 mg and up to 10 mg; and in the case of losartan potassium salt is less than the recommended daily dose of 50 mg/day, preferably at least 1 mg and up to 40 mg, more preferably at least 2 mg and up to 30 mg, and still more preferably at least 4 mg and up to 20 mg.

In the case of pioglitazone hydrochloride, the daily dose is equal or less than the recommended daily dose of 60 mg/day, preferably at least 5 mg and up to 50 mg, more preferably at least 10 mg and up to 40 mg, and still more preferably at least 20 mg and up to 30 mg; in the case of rosiglitazone maleate, the daily dose is equal or less than the recommended daily dose of 16 mg/day, preferably at least 1 mg and up to 12 mg, more preferably at least 2 mg and up to 10 mg, and still more preferably at least 4 mg and up to 8 mg; in the case of nateglinide, less than the recommended daily dose of 500 mg/day, preferably at least 10 mg and up to 400 mg, more preferably at least 20 mg and up to 350 mg, and still more preferably at least 50 mg and up to 300 mg; in the case of metformin hydrochloride, the daily dose is equal or less than the recommended daily dose of 2000 mg/day, preferably at least 40 mg and up to 1500 mg, more preferably at least 80 mg and up to 1200 mg, and still more preferably at least 200 mg and up to 1000 mg; in the case of buformin hydrochloride, less than the recommended daily dose of 400 mg/day, preferably at least 10 mg and up to 300 mg, more preferably at least 20 mg and up to 250 mg, and still more preferably at least 50 mg and up to 200 mg; in the case of ipragliflozin, the daily dose is equal or less than the recommended daily dose of 100 mg/day, preferably at least 5 mg and up to 90 mg, more preferably at least 10 mg and up to 75 mg, and still more preferably at least 25 mg and up to 50 mg and in the case of luseogliflozin, the daily dose is equal or less than the recommended daily dose of 5 mg/day, preferably at least 0.5 mg and up to 4 mg, more preferably at least 1 mg and up to 3 mg, and still more preferably at least 1.5 mg and up to 2.5 mg.

Exemplary antioxidants include vitamins such as ascorbic acid (vitamin C), tocopherol (vitamin E), and tocopherol nicotinate, and N-acetylcysteine, probucol.

Exemplary blood flow improving agents include aspirin, cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, and shimotsu-to extract.

Exemplary bile acid derivatives include ursodeoxycholic acid, chenodeoxycholic acid, bile powder, deoxycholic acid, cholic acid, bile extract, bear bile, oriental bezoar, and dehydrocholic acid. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin. Exemplary antioxidants include vitamins such as ascorbic acid (vitamin C), tocopherol (vitamin E), and tocopherol nicotinate, and N-acetylcysteine, probucol. The preferable antioxidant is tocopherol (vitamin E).

Exemplary blood flow improving agents include aspirin, cilostazol, ticlopidine hydrochloride, clopidogrel, prasugrel, edoxaban tosilate hydrate, rivaroxaban, dabigatran etexilatealprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, and shimotsu-to extract. The preferable blood flow improving agents are aspirin, clopidogrel, prasugrel, edoxaban tosilate hydrate, rivaroxaban and dabigatran etexilate.

Exemplary bile acid derivatives, which are optionally FXR ligand, include ursodeoxycholic acid, chenodeoxycholic acid, obeticholic acid, GW4064, bile powder, deoxycholic acid, cholic acid, bile extract, bear bile, oriental bezoar, and dehydrocholic acid. The preferable bile acid derivatives are ursodeoxycholic acid, chenodeoxycholic acid, obeticholic acid, GW4064, bile powder, deoxycholic acid, and cholic acid. The more preferable bile acid derivative is FXR ligand such as chenodeoxycholic acid, obeticholic acid, and GW4064. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin. In the case of tocopherol (vitamin E), the daily dose is equal or less than 1600 IU/day, preferably at least 100 IU and up to 1200 IU, more preferably at least 200 IU and up to 1000 IU, and still more preferably at least 400 IU and up to 800 IU or the daily dose is equal or less than 600 mg/day, preferably at least 50 mg and up to 500 mg, more preferably at least 100 mg and up to 400 mg, and still more preferably at least 200 mg and up to 300 mg and in the case of ascorbic acid (vitamin C) or vitamin Bs, the daily dose is equal or less than 2000 mg/day, preferably at least 40 mg and up to 1500 mg, more preferably at least 80 mg and up to 1200 mg, and still more preferably at least 200 mg and up to 1000 mg. In the case of ursodeoxycholic acid, the daily dose is equal or less than 30 mg/day, preferably at least 1 mg and up to 25 mg, more preferably at least 2 mg and up to 20 mg, and still more preferably at least 5 mg and up to 15 mg and in the case of obeticholic acid, the daily dose is equal or less than 50 mg/day, preferably at least 1 mg and up to 40 mg, more preferably at least 2 mg and up to 30 mg, and still more preferably at least 5 mg and up to 25 mg.

The preferable combinations are comprising at least EPAs and lovastatin, EPAs and pravastatin, EPAs and simvastatin, EPAs and atorvastatin, EPAs and fluvastatin, EPAs and pitavastatin, EPAs and rosuvastatin, EPAs and cerivastatin, EPAs and simfibrate, EPAs and clofibrate, EPAs and clinofibrate, EPAs and bezafibrate, EPAs and ezetimibe, EPAs and AMG145, EPAs and SAR236553/Regn727, EPAs and RN316, EPAs and LGT209, EPAs and irbesartan, EPAs and olmesartan medoxomil, EPAs and candesartan cilexetil, EPAs and telmisartan, EPAs and valsartan, EPAs and losartan potassium, EPAs and alacepril, EPAs and imidapril hydrochloride, EPAs and enalapril maleate, EPAs and captopril, EPAs and quinapril hydrochloride, EPAs and cilazapril hydrate, EPAs and temocapril hydrochloride, EPAs and delapril hydrochloride, EPAs and trandolapril, EPAs and benazepril hydrochloride, EPAs and perindopril, EPAs and lisinopril hydrate, EPAs and azelnidipine, EPAs and amlodipine besylate, EPAs and cilnidipine, EPAs and nicardipine hydrochloride, EPAs and nifedipine, EPAs and manidipine, EPAs and acarbose, EPAs and voglibose, EPAs and glibenclamide, EPAs and glimepiride, EPAs and tolbutamide, EPAs and nateglinide, EPAs and mitiglinide, EPAs and metformin hydrochloride, EPAs and buformin hydrochloride, EPAs and sitagliptin, EPAs and vildagliptin, EPAs and alogliptin, EPAs and linagliptin, EPAs and saxagliptin, EPAs and pioglitazone hydrochloride, EPAs and rosiglitazone maleate, EPAs and exenatide, EPAs and lixisenatide and EPAs and liraglutide, EPAs and muraglitazar, EPAs and tesaglitzar, EPAs and reglitazar, EPAs and farglitazar, EPAs and GFT505, EPAs and canagliflozin, EPAs and dapagliflozin, EPAs and Luseogliflozin, EPAs and tofogliflozin, EPAs and empagliflozin, EPAs and ipragliflozin, EPAs and tocopherol (vitamin E), EPAs and aspirin, EPAs and clopidogrel, EPAs and prasugrel, EPAs and edoxaban tosilate hydrate, EPAs and rivaroxaban, EPAs and dabigatran etexilate, EPAs and ursodeoxycholic acid, EPAs and chenodeoxycholic acid, EPAs and obeticholic acid, EPAs and GW4064, EPAs and bile powder, EPAs and deoxycholic acid, and EPAs and cholic acid. The more preferable combinations are comprising at least EPAs and pravastatin, EPAs and simvastatin, EPAs and atorvastatin, EPAs and fluvastatin, EPAs and pitavastatin, EPAs and rosuvastatin, EPAs and ezetimibe, EPAs and irbesartan, EPAs and olmesartan medoxomil, EPAs and candesartan cilexetil, EPAs and telmisartan, EPAs and valsartan, EPAs and losartan potassium, EPAs and sitagliptin, EPAs and vildagliptin, EPAs and alogliptin, EPAs and linagliptin, EPAs and saxagliptin, EPAs and pioglitazone hydrochloride, EPAs and rosiglitazone maleate, EPAs and exenatide, EPAs and lixisenatide and EPAs and liraglutide, EPAs and canagliflozin, EPAs and dapagliflozin, EPAs and Luseogliflozin, EPAs and tofogliflozin, EPAs and empagliflozin, EPAs and ipragliflozin. EPAs and tocopherol (vitamin E), EPAs and chenodeoxycholic acid, EPAs and obeticholic acid, EPAs and GW4064. The most preferable combinations are comprising at least EPAs and atorvastatin, EPAs and fluvastatin, EPAs and pitavastatin, EPAs and rosuvastatin, EPAs and irbesartan, EPAs and olmesartan medoxomil, EPAs and candesartan cilexetil, EPAs and telmisartan, EPAs and valsartan, EPAs and losartan potassium, EPAs and sitagliptin, EPAs and vildagliptin, EPAs and alogliptin, EPAs and linagliptin, EPAs and saxagliptin, EPAs and pioglitazone hydrochloride, EPAs and rosiglitazone maleate, EPAs and tocopherol (vitamin E), EPAs and chenodeoxycholic acid, EPAs and obeticholic acid. The preferable combinations are EPAs, at least one member selected from the group consisting of above mentioned agents for hyperlipidemia and at least one member selected from the group consisting of above mentioned antihypertensives. The preferable combinations are EPAs, at least one member selected from the group consisting of above mentioned agents for hyperlipidemia and at least one member selected from the group consisting of above mentioned anti-diabetic agents. The preferable combinations are EPAs, at least one member selected from the group consisting of above mentioned agents for hyperlipidemia and tocopherol (vitamin E). The preferable combinations are EPAs, at least one member selected from the group consisting of above mentioned agents for hyperlipidemia and at least one member selected from the group consisting of blood flow improving agents. The preferable combinations are EPAs, at least one member selected from the group consisting of above mentioned agents for hyperlipidemia and at least one member selected from the group consisting of above mentioned bile acid derivatives (including FXR ligands).

The preferable combinations are EPAs, at least one member selected from the group consisting of above mentioned antihypertensives and at least one member selected from the group consisting of above mentioned anti-diabetic agents. The preferable combinations are EPAs, at least one member selected from the group consisting of above mentioned antihypertensives and tocopherol (vitamin E). The preferable combinations are EPAs, at least one member selected from the group consisting of above mentioned antihypertensives and at least one member selected from the group consisting of blood flow improving agents. The preferable combinations are EPAs, at least one member selected from the group consisting of above mentioned antihypertensives and at least one member selected from the group consisting of above mentioned bile acid derivatives (including FXR ligands).

The preferable combinations are EPAs, at least one member selected from the group consisting of above mentioned anti-diabetic agents and tocopherol (vitamin E). The preferable combinations are EPAs, at least one member selected from the group consisting of above mentioned anti-diabetic agents and at least one member selected from the group consisting of blood flow improving agents. The preferable combinations are EPAs, at least one member selected from the group consisting of above mentioned anti-diabetic agents and at least one member selected from the group consisting of above mentioned bile acid derivatives (including FXR ligands). The preferable combinations are EPAs, tocopherol (vitamin E) and at least one member selected from the group consisting of blood flow improving agents. The preferable combinations are EPAs, tocopherol (vitamin E) and at least one member selected from the group consisting of above mentioned bile acid derivatives (including FXR ligands). The preferable combinations are EPAs, at least one member selected from the group consisting of blood flow improving agents and at least one member selected from the group consisting of above mentioned bile acid derivatives (including FXR ligands).

The preferable combinations are EPAs, at least one member selected from the group consisting of above mentioned agents for hyperlipidemia, at least one member selected from the group consisting of above mentioned antihypertensives, at least one member selected from the group consisting of above mentioned anti-diabetic agents and tocopherol (vitamin E). The preferable combinations are EPAs, at least one member selected from the group consisting of above mentioned agents for hyperlipidemia, at least one member selected from the group consisting of above mentioned antihypertensives, at least one member selected from the group consisting of above mentioned anti-diabetic agents and at least one member selected from the group consisting of above mentioned bile acid derivatives (including FXR ligands). The preferable combinations are EPAs, at least one member selected from the group consisting of above mentioned agents for hyperlipidemia, at least one member selected from the group consisting of above mentioned antihypertensives, tocopherol (vitamin E) and at least one member selected from the group consisting of above mentioned bile acid derivatives (including FXR ligands). The preferable combinations are EPAs, at least one member selected from the group consisting of above mentioned agents for hyperlipidemia, at least one member selected from the group consisting of above mentioned anti-diabetic agents, tocopherol (vitamin E) and at least one member selected from the group consisting of above mentioned bile acid derivatives (including FXR ligands). The preferable combinations are EPAs, at least one member selected from the group consisting of above mentioned agents for hyperlipidemia, at least one member selected from the group consisting of above mentioned anti-diabetic agents, tocopherol (vitamin E) and at least one member selected from the group consisting of above mentioned bile acid derivatives (including FXR ligands). The preferable combinations are EPAs, at least one member selected from the group consisting of above mentioned antihypertensives, at least one member selected from the group consisting of above mentioned anti-diabetic agents, tocopherol (vitamin E) and at least one member selected from the group consisting of above mentioned bile acid derivatives (including FXR ligands).

The preferable combinations are EPAs, at least one member selected from the group consisting of above mentioned agents for hyperlipidemia, at least one member selected from the group consisting of above mentioned antihypertensives, at least one member selected from the group consisting of above mentioned anti-diabetic agents, tocopherol (vitamin E) and at least one member selected from the group consisting of above mentioned bile acid derivatives (including FXR ligands).

The combination use of EPAs (first ingredient) and the second effective component such as agent for hyperlipidemia, antihypertensives, antidiabetics and farnesoid X receptor (FXR) ligands realizes safety and remarkable effectiveness of the level which are not observed by single administration of the corresponding agents. The combination use of EPAs (first ingredient) and the second effective component is expected to exhibit synergetic prophylactic/ameliorative or therapeutic effects for the NASH. The combination use of EPAs (first ingredient) and the second effective component is capable of reducing dose of agents and side effects of the agents. So it can also be administered to the patients who could not receive the treatment or the patients who had to stop the treatment because of the side effects of the second effective components.

D. Treatment Effects

The compositions of the present disclosure can be used as a therapeutic agent for various diseases of animals, and in particular, mammals, for example, therapeutic agent for NASH and related disorders. The compositions of the present disclosure are particularly expected to exhibit amelioration or therapeutic effects in NASH subjects without diabetes, or with pre-diabetes or mild diabetes, or without biliary tract disease, or in the early stages of the disease. NASH subjects may improve or maintain a variety of symptoms, which may include but are not limited to, increase in blood lipid, expression of insulin resistance, increase in blood pressure, abnormal liver function tests, abnormal liver enzyme activity, elevated glucose levels, liver dysfunction, hyperlipidemia, or any abnormal criteria as found in FIG. 5. In some cases, the pharmaceutical composition may aid in maintaining a function, level or activity present in a subject.

In some cases, the compositions may lower fasting glucose levels by methods as provided by the disclosure. In some cases, the composition may lower glucose levels as determined to be above normal, as would be found in pre-diabetic and mildly diabetic subjects. In some cases, the composition may lower high glucose levels in subjects not considered to have diabetes. In some cases, the pharmaceutical composition may aid in maintaining a glucose level present in a subject.

In some cases, the composition may lower GGT levels lower than the thresholds as provided by the disclosure. In some cases, the composition may lower GGT levels as determined to be above normal, as would be found in NASH subjects having biliary disease or be at risk for the disease. In some cases, the composition may lower GGT levels in subjects not considered to have biliary disease. In some cases, the pharmaceutical composition may aid in maintaining a GGT level present in a subject.

In some cases, the composition may lower sFas, M30 or NASH risk score levels lower than the thresholds as provided by the disclosure. In some cases, the composition may lower sFas, M30 or NASH risk score levels as determined to be above normal, as would be found in NASH subjects having hepatocyte apoptosis or be at risk for the indication. In some cases, the composition may lower sFas, M30 or NASH risk score levels in subjects not considered to have hepatocyte apoptosis. In some cases, the pharmaceutical composition may aid in maintaining a sFas, M30 or NASH risk score levels present in a subject. Further, in some cases a patient's EPA/AA ratio as compared to a baseline EPA/AA ratio may improve by equal to or greater than 0.1, 0.2, 0.3 or 0.4.

The compositions of the present disclosure can reduce burden of the patients by reducing the dose and daily frequency of the administration, and hence, by improving the drug compliance. This also results in the higher effects of amelioration or treatment.

IV. EXAMPLES

Example 1: Pre-Clinical Experience

In animal and in vitro model studies, EPA-E (ethyl all-cis-5,8,11,14,17-eicosapentaenoate) has been shown to lower lipids in rats, hamsters and rabbits; have anti-aggregation effects on platelets from rats, rabbits and humans; and to preserve the elasticity of arteries in rabbits. In other studies, polyunsaturated fatty acids (PUFAs) have been shown to ameliorate hepatic steatosis in ob/ob mice through down-regulation of hepatic nuclear sterol regulatory element binding protein-1c (SREBP-1c). In a similar manner, EPA-E following repeat oral administration at ≥0.1 mg/g suppressed fat accumulation in a mouse diet-induced hepatic steatosis model by suppressing hepatic SREBP-1c levels as well as monounsaturated fatty acid (MUFA) synthesis by stearoyl-Coenzyme A desaturase 1 (SCD1). In a galactosamine-induced steatohepatitis mouse model, EPA-E after oral administration at 1000 mg/kg retarded progression of steatohepatitis by suppressing triglyceride (TG) accumulation. EPA-E following repeat oral administration at 1000 mg/kg inhibited fibrosis by suppressing inflammation and oxidative stress in a methionine-choline deficient diet rat model of nonalcoholic steatohepatitis.

In safety pharmacology studies, at oral doses up to 3000 mg/kg, EPA-E had no effect on the central nervous, autonomic nervous, respiratory and cardiovascular systems except for a reduction in gastric fluid levels in pylorus-ligated rats after a 3000 mg/kg oral dose. The effects of the metabolites and impurities of EPA-E as well as oxidized EPA-E on the above systems were not marked and do not appear to significantly contribute to general pharmacological effects of EPA-E.

Pharmacokinetics and Product Metabolism in Animals Summary

EPADEL is a product containing ethyl all-cis-5,8,11,14, 17-eicosapentaenoate (EPA-E), one of the n-3 essential fatty acids. The preclinical absorption, distribution, metabolism and excretion (ADME) characteristics of EPA-E have been determined primarily in rats.

Oral administration of a single dose of radioactive $^{14}$C-EPA-E at the dose of 30-1000 mg/kg in rats showed that EPA-E was well-absorbed, mainly through the lymphatic route. After administration of $^{14}$C-EPA-E into the ligated intestine of rats, the residual radioactivity in the intestine at 24 hours was only 4.6% of the administered dose. Radioactivity transferred to the plasma and lymph was mainly detected in the triglyceride (TG) fraction in the early phase after dosing, while distribution to the free fatty acid (FFA) fraction was slight at all timepoints. The radioactivity was widely distributed in the body tissues; relatively high levels were observed especially in the brown fat, adrenal, liver and pancreas. Within the tissues, the radioactivity was mainly distributed in the TG and/or phospholipid (PL) fractions. $^{14}$C-EPA-E was hydrolyzed rapidly in the small intestine homogenates, lymph, plasma and liver homogenates of the rat. Orally administered EPA-E was primarily incorporated in adrenal gland lipids as cholesterol esters of the fatty acids eicosapentaenoic acid (EPA), docosapentaenoic acid (DPA) and docosahexaenoic acid (DHA).

The uptake of $^{14}$C-EPA-E-derived radioactivity in rats described above is compatible with the absorption process of essential fatty acids in animals and humans described below. In addition, esterases are also distributed in most of the organs in humans). Therefore, the absorption and distribution profiles after oral dosing of EPA-E should be qualitatively similar in humans and dogs as observed in rats.

The digestion and absorption of essential fatty acids, mainly in the form of TG, are known to involve several processes.

- The fatty acids are rapidly hydrolyzed from the TG to FFA by lipase in the intestine.
- The FFAs are taken up by the enterocytes where they are re-esterified into TG and enter the blood circulation, mainly through the lymphatic route as chylomicrons.
- In the tissues, the TG of the chylomicrons is hydrolyzed again by lipoprotein lipase to FFA and taken up by the tissues.

Consequently, when EPA-E is administered orally to humans, it would appear that it is well absorbed, even though the unchanged ethyl ester form is not detected, and the free form (EPA) is only detected at a very low level, in the blood. Due to this absorption mechanism of essential fatty acids, the administered EPA-E exists as a blood-constituent fatty acid in the total lipids. In fact, according to the approval package document of Lovaza®, the free form of EPA is undetectable in the circulation (<1 µM) following an oral dose of 4 g of Omacor® (a mixture of the ethyl esters of EPA and DHA) Following oral administration of EPA-E, EPA, DPA and DHA were isolated and identified as metabolites in tissues and plasma. EPA, DPA and DHA were incorporated into TG and PL. Radioactivity was primarily excreted in expired air (44%) after single oral administration at 30 mg/kg EPA-E with minimal excretion in bile and urine (~3%) and approximately 20% excreted in feces. Thus, the respiratory route (as $^{14}$CO2) was considered to be the major elimination pathway of $^{14}$C-EPA-E. Excretion of radioactivity in dogs after single oral administration at 30 mg/kg was low with 1.0% excreted in the urine and 19.2% recovered in the feces after 1 week.

Renal excretion was the elimination route for several minor highly polar metabolites (<0.4%), but EPA-E, EPA, DPA or DHA were not detected in the urine. In feces, EPA-E and EPA, evidently derived from the unabsorbed drug, were detected; however, no DPA or DHA was detected in the feces.

In metabolism studies conducted in vitro, when $^{14}$C-EPA-CoA was incubated with the rat liver mitochondrial fraction, 17.1% of the radioactivity added to the incubation mixture was detected as $^{14}$CO2 and the formation of carbon chain-shortened products was observed. Incubation of $^{14}$CEPA-CoA with a rat peroxisome fraction also resulted in the formation of carbon chain-shortened products. These results show that EPA, after being taken up by the rat tissues, is finally almost entirely oxidized to CO2 by mitochondrial and peroxisomal β-oxidation.

After oral administration of $^{14}$C-EPA-E to the rat, EPA, DPA and DHA were detected as metabolites in the total lipid fraction of the plasma and tissues (liver, fat, heart and brain). However, no unchanged EPA-E was found in the plasma or any of the tissues. In the total lipid fraction of the liver, the radioactivity originated mainly from EPA, DPA and DHA. Thus, it is considered that EPA, DPA and DHA are the predominant metabolites of $^{14}$C-EPA-E in tissues, as constituent fatty acids of the total lipid fraction. When $^{14}$C-EPA.K was incubated with the microsomal fraction, formation of DPA and DHA was detected. These results show that EPA taken up by the rat tissues is elongated to DPA and DHA in the microsomes.

Plasma protein binding in rats and dogs was >86% and >96%, respectively. Previous studies have shown that EPA is unlikely to inhibit CYP450 at free concentrations observed in humans.

Example 2: Clinical Trial Data

Study Design

This example provides the protocol used for an ongoing phase II clinical trial, double blind, placebo-controlled study to investigate the safety, efficacy, and pharmacokinetic profile of two doses of EPA-E in subjects with NASH. Up to 70 subjects were enrolled into each treatment arm, for a total of 210 subjects to be enrolled. Block randomization using an interactive voice response system (IVRS) was used to assign patients in a 1:1:1 ratio to two active doses and placebo. Patients were stratified at randomization by presence or absence of diabetes. Patients with diabetes comprised no more than 25% of the total number of patients enrolled. Subjects were treated with 600 mg EPA-E, 900 mg EPA-E or placebo three times a day for one year.

Study arm 1: 600 mg EPA-E (3 capsules), TID
Study arm 2: 900 mg EPA-E (3 capsules), TID
Study arm 3: placebo (3 capsules), TID Subjects were required to have a liver biopsy with proven NASH in the 6 month period prior to screening. The Pharmacokinetic profile for EPA-E was evaluated in a subgroup of subjects in specified sites. Subjects were approached prior to providing informed consent to determine if they will participate in the PK group subset. Approximately 36 subjects participated in the PK subset evaluation (12 from each treatment arm, to include 6 males and 6 females).

A study schematic is provided in FIG. 6. Overall study duration plan was 2 years.

The Investigational Drugs

In order to support the trial, EPA-E capsules and matching placebo capsules were prepared. EPA-E capsule is an oval soft gelatin capsule containing 300 mg of EPA-E as an active ingredient. Placebo capsule is an oval soft gelatin capsule containing olive oil as an inactive ingredient. These capsules are unidentifiable as EPA-E capsules or placebo capsules.

Subjects were administered orally 3 capsules 3 times daily, immediately after meals.

Eligibility Criteria

Subjects with a histological diagnosis of NASH are eligible.

Inclusion Criteria

Inclusion criteria were designed to ensure that subjects with biopsy proven NASH are included, and to avoid situations where potential harm may occur to subjects in conjunction with participation in the study.

Subjects were potentially included into the study if they met all the following criteria:

1. Diagnosis of definite NASH by the central reading pathologists:
   Liver biopsy slides will be submitted for evaluation by the central pathologists according to one of the following criteria:
   a. Previous liver biopsies must have been obtained within 6 months prior to informed consent and should be judged by the local pathologist as showing NAS ≥4 with a minimum score of 1 each for steatosis and lobular inflammation plus EITHER ballooning OR at least 1a sinusoidal fibrosis AND a finding of possible or definite steatohepatitis
  b. For liver biopsies performed after informed consent is obtained, all slides will be submitted for reading by the central pathologists in conformity with the independent pathology review charter (IPRC)
 2. Patients of either gender greater than 18 years of age
 3. Patients with diabetes that have been on stable doses of anti-diabetic agents since at least 6 months prior to liver biopsy may be enrolled
 4. Females must be of non-child bearing potential (surgically sterilized or at least two years post-menopausal) or if of child-bearing potential, must have a negative pregnancy test at screening and agree to use an effective form of contraception during the study and for at least 30 days following the last dose of study medication
 5. Normal ECG or clinically non-significant findings at the Screening and Baseline visits
 6. No significant concomitant medical illness, without any clinically significant physical exam findings and without any clinically significant laboratory findings, as determined by the principal investigator
 7. Signed an informed consent form indicating that they understand the purpose of and procedures required for the study and are willing to participate in the study and comply with the study procedures and restrictions Exclusion Criteria Exclusion criteria have been designed to exclude subjects from the study if they will not be evaluable for the primary endpoint, if they have disease states that would interfere with analysis of study endpoints, or would put subjects at risk of serious adverse events associated with their participation.

Potential subjects will be excluded from participating in the study if they meet any of the following exclusion criteria:
 1. Inability or unwillingness to have a liver biopsy
 2. Diagnosis of cirrhosis by central pathology reviewers
 3. Previous bariatric surgery or biliary diversion (i.e. gastric bypass), esophageal banding and gastric banding
 4. Serum ALT >300 U/L
 5. Subject has used drugs associated with steatohepatitis within 6 months prior to screening (corticosteroids, high dose estrogens, methotrexate, amiodarone, anti-HIV drugs, tamoxifen and diltiazem)
 6. Use of the following anti-NASH agents for more than a 2 week period in the 3 months prior to liver biopsy or the 3 months prior to screening:
  a. Vitamin E >60 IU per day
  b. Omega-3-acid ethyl esters or omega-3-PUFA-containing supplements >200 mg per day
  c. Thiazoledinediones (e.g. pioglitazone)
 7. Patients on a non-stable dose of the following anti-NASH agents within 6 months of the liver biopsy or within 6 months of the screening visit: HMG-CoA reductase inhibitors (statins), fibrates, probucol, ezetimibe, ursodiol (UDCA), taurine, betaine, N-acetylcysteine, s-adenosylmethionine (SAM-e), milk thistle, anti-TNF therapies, or probiotics
 8. Greater than a 10% decrease in weight within 8 weeks of baseline visit
 9. Alcohol consumption >30 g/day, currently or for more than 3 consecutive months within 5 years of screening
 10. Blood alcohol level greater than 0.02% at screening and/or baseline
 11. Evidence of active substance abuse, including prescription and recreational drugs
 12. Other liver disease (hepatitis C, hepatitis B, Wilson's, autoimmune, α-1-antitrypsin and hemochromatosis) or known HIV infection
 13. Pregnant or lactating at the screening visit
 14. Renal insufficiency (creatinine >2 mg/dL), symptomatic coronary, peripheral or neurovascular disease, symptomatic heart failure (NYHA 2-4) or advanced respiratory disease requiring oxygen therapy
 15. History of cerebral or retinal hemorrhage or other bleeding diathesis
 16. QTc>450 msec for males and >470 for females as corrected by the Fridericia formula
 17. Inability to provide written informed consent
 18. Received any investigational agent or participation in any clinical study of an investigational agent or investigational therapy within 3 months prior to the screening visit.
 19. Any condition in the opinion of the Principal Investigator that would contraindicate the patient's participation Prohibited and Concomitant Medications All prescription and over-the-counter medications taken by subjects during the 30 days before screening up to the start of treatment were recorded. The following medications were prohibited during participation in the study:
  Omega-3-acid ethyl esters and omega-3-PUFA containing supplements >200 mg per day
  Vitamin E >60 IU per day
  Thiazolidinediones (e.g. pioglitazone)

The following medications were allowed during the study according to the specified restrictions:
  Subjects could continue prescription or over-the-counter medications or herbal remedies (HMG-CoA reductase inhibitors [statins], fibrates, probucol, ezetimibe, ursodiol [UDCA], taurine, betaine, N-acetylcysteine, s-adenosylmethionine [SAM-e], milk thistle, anti-TNF therapies, or probiotics) ONLY if they have been on a stable dose for at least 6 months prior to screening
  Subjects could continue the following anti-diabetic medications if they have been taking stable doses since at least 6 months prior to liver biopsy: biguanides (metformin), insulin, sulfonylureas, alpha-glucosidase inhibitors (acarbose), and phenylalanine derivatives (nateglinide)
  Any subjects receiving anti-platelet therapy or anti-thrombotic agents (e.g. warfarin, ASA, and clopidogrel) after study commencement should be monitored closely during the study Preliminary Results A) A sub-population of NASH patients were counted and classified as responders or non responders as shown in FIG. 1. Preliminary data indicated higher efficacy of the pharmaceutical composition in patients who were determined not to have diabetes or showed mild diabetes as compared to diabetic patients in Study arm 1 (600 mg EPA-E, TID). The efficacy of Study arm 2 (900 mg EPA-E, TID) was also equivalent to that of Study arm 1.

The same sub-population of patients was further characterized. HbA1c levels were measured for patients, whose HbA1c=<6.4, as shown in FIG. 2. Preliminary data indicates higher efficacy of the pharmaceutical composition in patients with HbA1c levels=<6.4 in all cases, and especially who would be classified as non-diabetic (including pre-diabetic) based on guidelines as set by the ADA and as described herein in Study arm 1. The efficacy of Study arm 2 was also equivalent to that of Study arm 1.

Diabetes in the same sub population of patients was alternatively measured using a test for fasting glucose. Glucose levels were measured for patients, whose glucose levels were =<125 mg/dL and, as shown in FIG. 3. Preliminary data indicates higher efficacy of the pharmaceutical composition in patients with =<125 mg/dL and who would be classified as non-diabetic (including pre-diabetic) or diabetic based on guidelines as set by the ADA and as described herein in Study arm 1. The efficacy of Study arm 2 was also equivalent to that of Study arm 1.

The chart in FIG. 4 indicates that taken together, non-diabetic (including pre-diabetic) or diabetic, as measured by both fasting glucose=<125 mg/dL and HbA1c=<6.4, indicated a higher response to rate to the EPA-E in Study arm 1. The efficacy of Study arm 2 was also equivalent to that of Study arm 1.

B) A second sub-population of NASH patients were counted and classified as responders or non responders as shown in FIG. 7. Preliminary data indicates higher efficacy of the pharmaceutical composition in patients who were determined not to have biliary tract disease markers associated with the disease in both Study arm 1 (600 mg EPA-E, TID) and Study arm 2 (900 mg EPA-E, TID).

γ-Glutamyl Transferase (GGT) v. Preliminary Endpoint achievement rate is reflected in FIG. 8. Preliminary data indicates higher efficacy of the pharmaceutical composition in patients with GGT levels=<60 IU/L in both Study arm 1 and 2.

The same sub-population of patients was further characterized. NASH response (change of NAS score) was measured for patients, whose GGT levels=<33 IU/L, as shown in the table of FIG. 9. Preliminary data indicates higher efficacy of the pharmaceutical composition in patients with GGT levels=<33 IU/L, and who would be classified as not having biliary duct disease in both Study arm 1 and 2.

Alternatively, improvement of serum EPA/AA ratio on Day 365 of patients with γ-Glutamyl Transferase (GGT) levels ≤33 IU/L was also measured, as shown in the table of FIG. 10. Preliminary data indicates higher efficacy of the pharmaceutical composition in patients with ≤33 IU/L and who would be classified as not biliary duct disease in Study arm 2.

The table in FIG. 11 provides corresponding reference values for parameters of liver function in patients with γ-Glutamyl Transferase (GGT) levels ≤33 IU/L and patients with γ-Glutamyl Transferase (GGT) levels ≥33 IU/L. Serum direct bilirubin levels were also assays in the sub group of patients with γ-Glutamyl Transferase (GGT) levels ≥33 IU/L. All patients were observed within reference (normal) value for direct bilirubin levels. The range of serum direct bilirubin of patients with serum GGT levels ≤33 IU/L was between 0.03 and 0.17.

Figure 12:
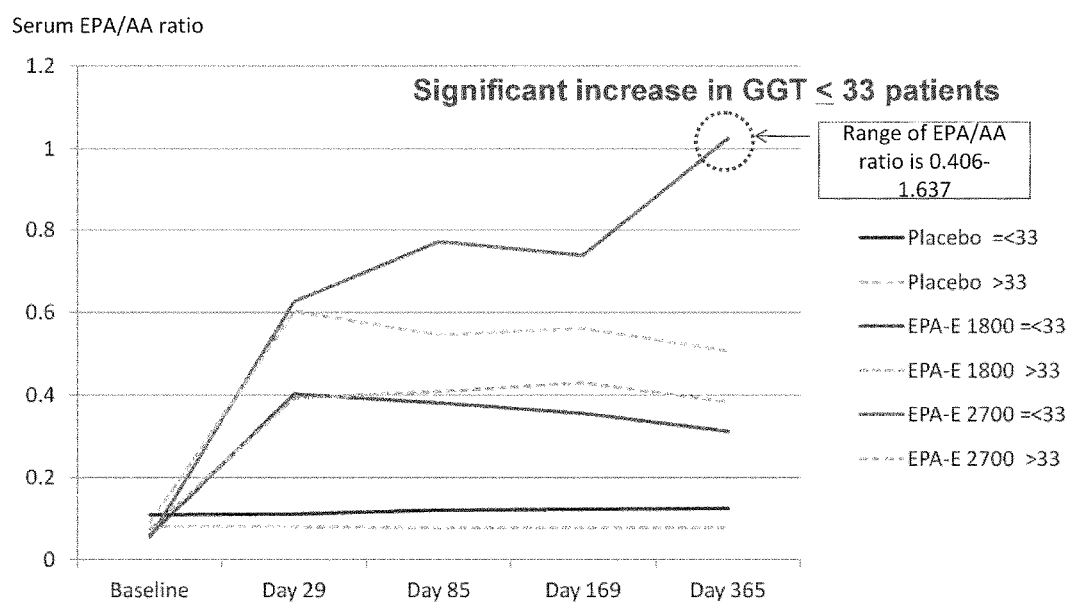
FIG. 12 is a chart representing serum EPA/AA ratios for various administered dosages of EPA-E over time.

FIG. 12 is a chart representing serum EPA/AA ratios for various administered dosages of EPA-E over time. The chart indicates a significant increase in EPA/AA ratio in patients with γ-Glutamyl Transferase (GGT) levels ≤33 IU/L in Study arm 2. The range of the improvement in this ratio on Day 365 of patients with serum GGT levels ≤33 IU/L was observed between 0.0406 and 1.637 for administered 2700 mg/day dose of EPA-E.

Figure 13:
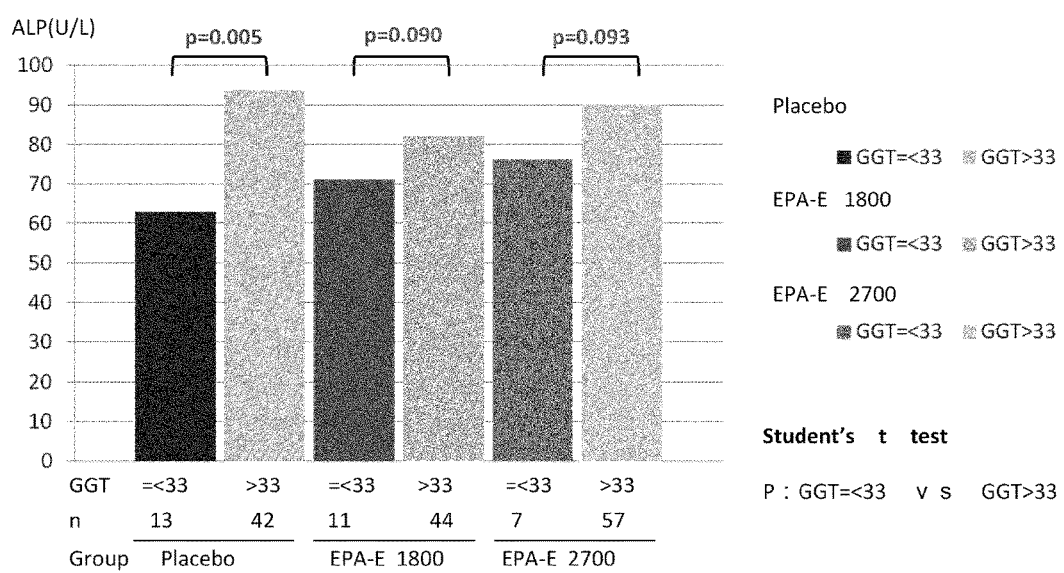
FIG. 13 is a chart representing serum ALP of patients with γ-Glutamyl Transferase (GGT) levels ≤33 IU/L.

ALP levels were also assays in the sub group of patients with γ-Glutamyl Transferase (GGT) levels ≤33 IU/L and patients with γ-Glutamyl Transferase (GGT) levels ≥33 IU/L. Some patients in GGT>=33 IU/L and placebo group showed ALP value above reference (normal) value as shown in FIG. 13.

C) A third sub-population of NASH patients were counted and classified as responders or non responders as shown in FIG. 14. Preliminary data indicates higher efficacy of the pharmaceutical composition in patients who were determined to have serum levels of sFas equal to or less 9.5 ng/mL associated with NASH (1800 mg EPA-E, TID).

sFas level v. proportion of responders is reflected in FIG. 15. Preliminary data indicates higher efficacy of the pharmaceutical composition in patients who were determined to have serum levels of sFas equal to or less 10.0 ng/mL, especially equal to or less 9.5 ng/mL associated with NASH (1800 mg EPA-E, TID).

The same sub-population of patients was further characterized. NASH response (change of NAS score) was measured for patients, determined to have serum levels of sFas equal to or less 9.5 ng/mL, as shown in the table of FIG. 16. Preliminary data indicates higher efficacy of the pharmaceutical composition in patients with determined to have serum levels of sFas equal to or less 9.5 ng/mL, and who would be classified as not having non or early stage hepatocyte apoptosis in Study arm 1 (1800 mg EPA-E, TID).

A sub-population of NASH patients were counted and classified as responders or non responders as shown in FIG. 17. Preliminary data indicates higher efficacy of the pharmaceutical composition in patients who were determined to have serum levels of M30 equal to or less 1500 U/L, especially equal to or less 900 U/L, more especially equal to or less 500 U/L associated with NASH (1800 mg EPA-E, TID).

sFas and M30 levels v. Proportion of responders are reflected in FIG. 18. Preliminary data indicates higher efficacy of the pharmaceutical composition in patients who were determined to have serum levels of sFas equal to or less 10.0 ng/mL, especially equal to or less 9.7 ng/mL, more especially equal to or less 9.5 ng/mL and/or M30 equal to or less 1500 U/L, especially equal to or less 600 U/L, more especially equal to or less 500 U/L associated with NASH (1800 mg EPA-E, TID and 2700 mg EPA-E, TID).

A sub-population of NASH patients were counted and classified as responders or non responders as shown in FIG. 19. Preliminary data indicates higher efficacy of the pharmaceutical composition in patients who were determined to NASH risk score equal to or less than 4.0, especially equal to or less than 3.0 associated with NASH (1800 mg EPA-E, TID).

FIG. 20 provides for reference values for parameters of hepatocyte apoptosis in patients with sFas ≤9.5 ng/mL and reference values as determined by Tamimi T I., et. al., J. Hepatol., 54, 1224-1229, 2011. Preliminary data indicates M30 levels in patients with sFas ≤9.5 ng/mL were lower than those in patients with sFas >9.5 ng/mL and were almost same level as reference value of NASH patients in Tamimi article.

Figure 21:
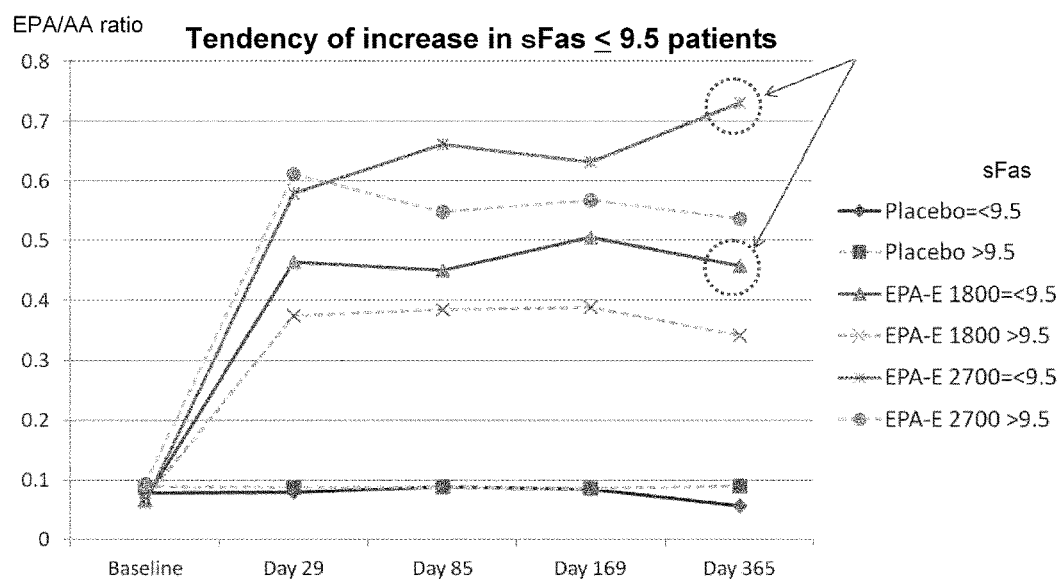
FIG. 21 is a chart representing serum EPA/AA ratios for various administered dosages of EPA-E over time.

Alternatively, improvement of serum EPA/AA ratio on Day 365 of patients with serum levels of sFas equal to or less 9.5 ng/mL associated with the disease was also measured, as shown in the chart of FIG. 21. Preliminary data indicates EPA/AA ratios in patients with sFas≤9.5 ng/mL, who were higher efficacy of the pharmaceutical composition and would be classified as having non or early hepatocyte apoptosis, were higher than those in patients with sFas >9.5 ng/mL.

The table in FIG. 22 provides corresponding EPA/AA ratio results for patients with sFas equal to or less 9.5 ng/mL and who would be classified as having non or early hepatocyte apoptosis. Preliminary data indicates EPA/AA ratios in patients with sFas≤9.5 ng/mL were higher than those in patients with sFas >9.5 ng/mL.

Example 3: Self-Emulsifying Formulation 0.5 g of soybean lecithin, 1.0 g of polyoxyethylene (60) hydrogenated castor oil, 0.4 g of propylene glycol, and 3.1 g of EPA-E were weighed, and mixed while heating to a temperature of about 70° C. to prepare a self-emulsifying composition. After substituting with nitrogen, the self-emulsifying composition was hermetically sealed and stored at room temperature until the evaluation. Formulation of the self-emulsifying composition is shown below:

| Ingredients | Formulation (% by weight) |
| --- | --- |
| EPA-E | 62.0 |
| Soybean lecithin | 10.0 |
| Polyoxyethylene (60) hydrogenated castor oil | 20.0 |
| Propylene glycol | 8.0 |
| Total | 100.0 |

Example 4: Self-Emulsifying Formulation 0.5 g of soybean lecithin, 1.0 g of polyoxyethylene (50) hydrogenated castor oil, 0.4 g of propylene glycol, and 3.1 g of EPA-E were weighed, and a self-emulsifying composition was prepared and stored by repeating the procedure of Example 3. Formulation of the self-emulsifying composition is shown below:

| Ingredients | Formulation (% by weight) |
| --- | --- |
| EPA-E | 62.0 |
| Soybean lecithin | 10.0 |
| Polyoxyethylene (60) hydrogenated castor oil | 20.0 |
| Propylene glycol | 8.0 |
| Total | 100.0 |

Example 5: Self-Emulsifying Formulation 0.5 g of soybean lecithin. 0.9 g of polyoxyethylene castor oil, 0.6 g of propylene glycol, and 3.0 g of EPA-E were weighed, and a self-emulsifying composition was prepared and stored by repeating the procedure of Example 1. Formulation of the self-emulsifying composition is shown below:

| Ingredients | Formulation (% by weight) |
| --- | --- |
| EPA-E | 60.0 |
| Soybean lecithin | 10.0 |
| Polyoxyethylene castor oil | 18.0 |
| Propylene glycol | 12.0 |
| Total | 100.0 |

Example 6: Self-Emulsifying Formulation 0.6 g of soybean lecithin, 0.6 g of polyoxyethylene (60) hydrogenated castor oil, 0.5 g of propylene glycol, and 3.3 g of EPA-E were weighed, and a self-emulsifying composition was prepared and stored by repeating the procedure of Example 1. Formulation of the self-emulsifying composition is shown below:

| Ingredients | Formulation (% by weight) |
| --- | --- |
| EPA-E | 66.0 |
| Soybean lecithin | 12.0 |
| Polyoxyethylene (60) hydrogenated castor oil | 12.0 |
| Propylene glycol | 10.0 |
| Total | 100.0 |

Example 7: Self-Emulsifying Formulation 0.5 g of soybean lecithin, 0.5 g of polyoxyethylene (50) hydrogenated castor oil, 0.5 g of propylene glycol, and 3.5 g of EPA-E were weighed, and a self-emulsifying composition was prepared and stored by repeating the procedure of Example 3. Formulation of the self-emulsifying composition is shown below:

| Ingredients | Formulation (% by weight) |
| --- | --- |
| EPA-E | 70.0 |
| Soybean lecithin | 10.0 |
| Polyoxyethylene (50) hydrogenated castor oil | 10.0 |
| Propylene glycol | 10.0 |
| Total | 100.0 |

Example 8: Self-Emulsifying Formulation 0.3 g of soybean lecithin, 0.3 g of polyoxyethylene (20) sorbitan monooleate, 0.9 g of polyoxyethylene (60) hydrogenated castor oil, 0.4 g of propylene glycol, and 3.1 g of EPA-E were weighed, and a self-emulsifying composition was prepared and stored by repeating the procedure of Example 3. Formulation of the self-emulsifying composition is shown below:

| Ingredients | Formulation (% by weight) |
| --- | --- |
| EPA-E | 62.0 |
| Soybean lecithin | 6.0 |
| Polyoxyethylene (20) sorbitan monooleate | 6.0 |
| Polyoxyethylene (60) hydrogenated castor oil | 18.0 |
| Propylene glycol | 8.0 |
| Total | 100.0 |

Example 9: Self-Emulsifying Formulation 0.22 g of soybean lecithin, 0.36 g of polyoxyethylene (20) sorbitan monooleate, 0.36 g of polyoxyethylene 35 castor oil, 1.2 g of purified water and 4.0 g of EPA-E were weighed, and a self-emulsifying composition was prepared and stored by repeating the procedure of Example 3. Formulation of the self-emulsifying composition is shown below:

| Ingredients | Formulation (% by weight) |
|---|---|
| EPA-E | 80.0 |
| Soybean lecithin | 4.4 |
| Polyoxyethylene (20) sorbitan monooleate | 7.2 |
| Polyoxyethylene 35 castor oil | 7.2 |
| Purified water | 1.2 |
| Total | 100.0 |

What is claimed is:

1. A method for treating a fatty liver disease or disorder in a subject in need thereof,
wherein the subject before the treating has one or more criteria of:
a serum level of soluble Fas (sFas) equal to or less than 10.0 ng/mL,
a serum level of cytokeratin-18 fragment M30 (M30) equal to or less than 1500 U/L, or
a non-alcoholic steatohepatitis (NASH) risk score equal to or less than 3, wherein the NASH risk score=−6.4894+0.0078×M30 (U/L)+0.4668×sFas (ng/mL),
comprising administering to the subject a therapeutically effective amount of a pharmaceutical composition comprising ethyl eicosapentanoate (EPA-E), eicosapentaenoic acid (EPA), or a pharmaceutically acceptable amide, salt, ester, or phospholipid thereof.

2. The method of claim 1, wherein the subject is non-diabetic, pre-diabetic, or mildly diabetic.

3. The method of claim 1, wherein the subject receives no treatment for diabetes or no anti-diabetic agent.

4. The method of claim 1, wherein the fatty liver disease or disorder is non-alcoholic fatty liver disease (NAFLD).

5. The method of claim 1, wherein the fatty liver disease or disorder is NASH.

6. The method of claim 1, wherein the fatty liver disease is characterized by the baseline pretreatment level in the subject of at least one criteria selected from the group consisting of alanine aminotransferase (ALT) in a range of 10 to 300 U/L, aspartate aminotransferase (AST) in a range of 10 to 250 U/L, high density lipoprotein cholesterol (HDL-C) in a range of 25 to 55 mg/dl, low density lipoprotein cholesterol (LDL-C) in a range of 100 to 200 mg/dl, triglycerides (TG) in a range of 100 to 1000 mg/dl, total cholesterol (TC) in a range of 170 to 300 mg/dl, High TG and low HDL-C, TG/HDL-C ratio in a range of 3.75 to 10, non-HDL-C in a range of 100 to 250 mg/dl, free fatty acid in a range of 400 to 1000µ Eq/L, homeostasis model assessment of insulin resistance (HOMA-IR) in a range of 1.5 to 5, glycated hemoglobin (HbA1c) in a range of 5.7 to 10%, fasting plasma glucose in a range of 100 to 200 mg/dl, impaired glucose tolerance, and metabolic syndrome.

7. The method of claim 1, wherein the pharmaceutical composition comprises the EPA-E.

8. The method of claim 7, wherein a therapeutically effective amount of the EPA-E administered to the subject is an amount from about 1800 to about 2700 mg per day.

9. The method of claim 7, wherein a therapeutically effective amount of the EPA-E administered to the subject is at least 1800 mg per day.

10. The method of claim 7, wherein a therapeutically effective amount of the EPA-E administered to the subject is at least 2700 mg per day.

11. The method of claim 1, wherein the pharmaceutical composition is a self-emulsifying composition comprising 50 to 95% by weight of the EPA-E, EPA or a pharmaceutically acceptable amide, salt, ester or phospholipid thereof.

12. The method of claim 1, wherein the pharmaceutical composition is a self-emulsifying composition comprising at least 60% by weight of the EPA-E, EPA, or a pharmaceutically acceptable amide, salt, ester, or phospholipid thereof.

13. The method of claim 1, wherein the pharmaceutical composition comprises at least 5% by weight of an emulsifier.

14. The method of claim 13, wherein the emulsifier has a hydrophilic lipophilic balance of at least 10.

15. The method of claim 13, wherein the emulsifier is at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, sorbitan fatty acid ester, and glycerin fatty acid ester.

16. The method of claim 13, wherein the emulsifier is at least one member selected from the group consisting of polyoxyethylene (20) hydrogenated castor oil, polyoxyethylene (40) hydrogenated castor oil, polyoxyethylene (50) hydrogenated castor oil, polyoxyethylene (60) hydrogenated castor oil, and polyoxyethylene (100) hydrogenated castor oil.

17. The method of claim 13, wherein the emulsifier is at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate.

18. The method of claim 13, wherein the pharmaceutical composition comprises ethanol content up to 4% by weight.

19. The method of claim 13, wherein the pharmaceutical composition further comprises a lecithin.

20. The method of claim 19, wherein the lecithin is at least one member selected from the group consisting of soybean lecithin, enzymatically decomposed soybean lecithin, hydrogenated soybean lecithin, and egg yolk lecithin.

21. The method of claim 1, wherein the pharmaceutical composition further comprises a polyhydric alcohol.

22. The method of claim 21, wherein the polyhydric alcohol is propylene glycol or glycerin.

23. The method of claim 1, wherein the subject before the treating has the NASH risk score equal to or less than 3.

24. The method of claim 1, wherein the subject before the treating has the serum level of sFas equal to or less than 10.0 ng/mL.

25. The method of claim 1, wherein the subject before the treating has the serum level of M30 equal to or less than 1500 U/L.

26. The method of claim 1, wherein the subject before the treating has the serum level of sFas equal to or less than 10.0 ng/mL and the serum level of M30 equal to or less than 1500 U/L.

27. The method of claim 1, wherein the subject before the treating has the serum level of sFas equal to or less than 10.0 ng/mL and the NASH risk score equal to or less than 3.

28. The method of claim 1, wherein the subject before the treating has the serum level of M30 equal to or less than 1500 U/L and the NASH risk score equal to or less than 3.

29. The method of claim 1, wherein the subject before the treating has the serum level of sFas equal to or less than 10.0 ng/mL, the serum level of M30 equal to or less than 1500 U/L, and the NASH risk score equal to or less than 3.

* * * * *